(12) United States Patent
Eves et al.

(10) Patent No.: US 11,931,512 B2
(45) Date of Patent: Mar. 19, 2024

(54) ORO-NASAL PATIENT INTERFACE

(71) Applicant: RESMED PTY LTD, Bella Vista (AU)

(72) Inventors: Matthew Eves, Sydney (AU); Andrew James Bate, Sydney (AU); Sebastien Deubel, Sydney (AU); Paul Derrick Watson, Sydney (AU); Matthew Robin Wells, Sydney (AU); Beng Hai Tan, Singapore (SG); Chee Keong Ong, Singapore (SG); Marvin Sugi Hartono, Singapore (SG); Han Cheng Lin, Singapore (SG)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/641,751

(22) PCT Filed: Sep. 9, 2020

(86) PCT No.: PCT/AU2020/050953
§ 371 (c)(1),
(2) Date: Mar. 9, 2022

(87) PCT Pub. No.: WO2021/046599
PCT Pub. Date: Mar. 18, 2021

(65) Prior Publication Data
US 2022/0323702 A1    Oct. 13, 2022

Related U.S. Application Data

(60) Provisional application No. 63/058,001, filed on Jul. 29, 2020.

(30) Foreign Application Priority Data

Sep. 10, 2019  (AU) ................................ 2019903360

(51) Int. Cl.
*A61M 16/06* (2006.01)

(52) U.S. Cl.
CPC .... *A61M 16/0616* (2014.02); *A61M 16/0683* (2013.01)

(58) Field of Classification Search
CPC ........................................... A61M 16/06–0694
(Continued)

(56) References Cited

U.S. PATENT DOCUMENTS 4,782,832 A   11/1988  Trimble et al.
4,944,310 A    7/1990  Sullivan
(Continued)

FOREIGN PATENT DOCUMENTS

WO    WO 98/004310 A1    2/1998
WO    WO 98/034665 A1    8/1998
(Continued)

OTHER PUBLICATIONS

"Respiratory Physiology", by John B. West, Lippincott Williams & Wilkins, 9th edition published 2012 (8 pages).
(Continued)

Primary Examiner — Elliot S Ruddie
(74) Attorney, Agent, or Firm — Nixon & Vanderhye P.C.

(57) ABSTRACT

A patient interface including a positioning and stabilizing structure that is configured to maintain a first seal-forming structure and a second seal-forming structure in a therapeutically effective position. The positioning and stabilizing structure comprises a frame coupled to the plenum chamber. The frame includes a central portion coupled to the plenum chamber outside of the cavity. The frame also includes a pair of arms that extend away from the central portion in a posterior direction past the second seal-forming structure. The pair of arms are more flexible than the central portion. The positioning and stabilizing structure also includes head-
(Continued)

gear straps coupled to the frame, which configured to provide a tensile force to the first seal-forming structure and to the second seal-forming structure into the patient's face via the frame.

28 Claims, 47 Drawing Sheets

(58) Field of Classification Search
USPC .................................................. 128/207.11
See application file for complete search history.

(56) References Cited

U.S. PATENT DOCUMENTS

| | | | |
|---|---|---|---|
| 5,687,715 | A | 11/1997 | Landis |
| 6,123,071 | A | 9/2000 | Berthon-Jones et al. |
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 9,737,678 | B2 | 8/2017 | Formica et al. |
| 10,188,820 | B2 | 1/2019 | Edwards et al. |
| 11,077,274 | B2 | 8/2021 | Ng et al. |
| 2007/0125385 | A1* | 6/2007 | Ho .................... A61M 16/0683 128/206.26 |
| 2008/0035152 | A1 | 2/2008 | Ho et al. |
| 2009/0044808 | A1 | 2/2009 | Guney et al. |
| 2009/0050156 | A1 | 2/2009 | Ng et al. |
| 2010/0000534 | A1 | 1/2010 | Kooij et al. |
| 2015/0040909 | A1 | 2/2015 | Willard et al. |
| 2015/0040911 | A1 | 2/2015 | Davidson et al. |
| 2015/0075532 | A1 | 3/2015 | Patel |
| 2015/0352308 | A1 | 12/2015 | Cullen et al. |
| 2016/0082214 | A1* | 3/2016 | Barlow ................. A61M 16/06 128/206.24 |
| 2017/0312468 | A1 | 11/2017 | Formica et al. |
| 2018/0177965 | A1* | 6/2018 | Patel ................ A61M 16/0616 |
| 2018/0318539 | A1* | 11/2018 | Scheiner ........... A61M 16/0683 |
| 2019/0091433 | A1 | 3/2019 | Barlow et al. |

FOREIGN PATENT DOCUMENTS

| | | | |
|---|---|---|---|
| WO | WO 2000/078381 A1 | 12/2000 | |
| WO | WO 2004/073778 A1 | 9/2004 | |
| WO | WO 2005/063328 A1 | 7/2005 | |
| WO | WO 2006/074513 A1 | 7/2006 | |
| WO | WO 2006/130903 A1 | 12/2006 | |
| WO | WO 2009/052560 A1 | 4/2009 | |
| WO | WO 2010/135785 A1 | 12/2010 | |
| WO | WO 2012/171072 A1 | 12/2012 | |
| WO | WO 2013/020167 A1 | 2/2013 | |
| WO | 2016/082001 A1 | 6/2016 | |
| WO | WO-2017049359 A1 * | 3/2017 | ........ A61M 16/0066 |
| WO | 2019/183680 A1 | 10/2019 | |

OTHER PUBLICATIONS

International Search Report issued in International Application No. PCT/AU2020/050953 dated Dec. 8, 2020 (15 pages).
Written Opinion of the International Searching Authority issued in International Application No. PCT/AU2020/050953 dated Dec. 2020 (8 pages).
International Search Report issued in International Application No. PCT/AU2021/050826 dated Oct. 26, 2021 (12 pages).
Written Opinion of the International Searching Authority issued in International Application No. PCT/AU2021/050826 dated Oct. 26, 2021 (9 pages).
Written Opinion of the International Preliminary Examining Authority dated Aug. 26, 2022 issued in International Application No. PCT/AU2021/050826 (8 pages).
Office Action dated Oct. 25, 2022 issued in U.S. Appl. No. 17/599,420 citing US 2015/0128954 A1 (14 pages).
Notice of Allowance issued in related U.S. Appl. No. 17/599,420 dated Mar. 1, 2023, citing U.S. 2016/0022944 (Chodkowski), 16 pages.
Extended European Search Report dated Nov. 24, 2022 in related European Application No. 20778814.2, citing US 2017/0246411 (Mashal), WO 2017/124152 (Kooij), and WO 2014/183167 (Barlow) (8 pages).
Extended European Search Report for corresponding Application No. EP 20862176.3, dated Oct. 12, 2023, nine pages.

* cited by examiner

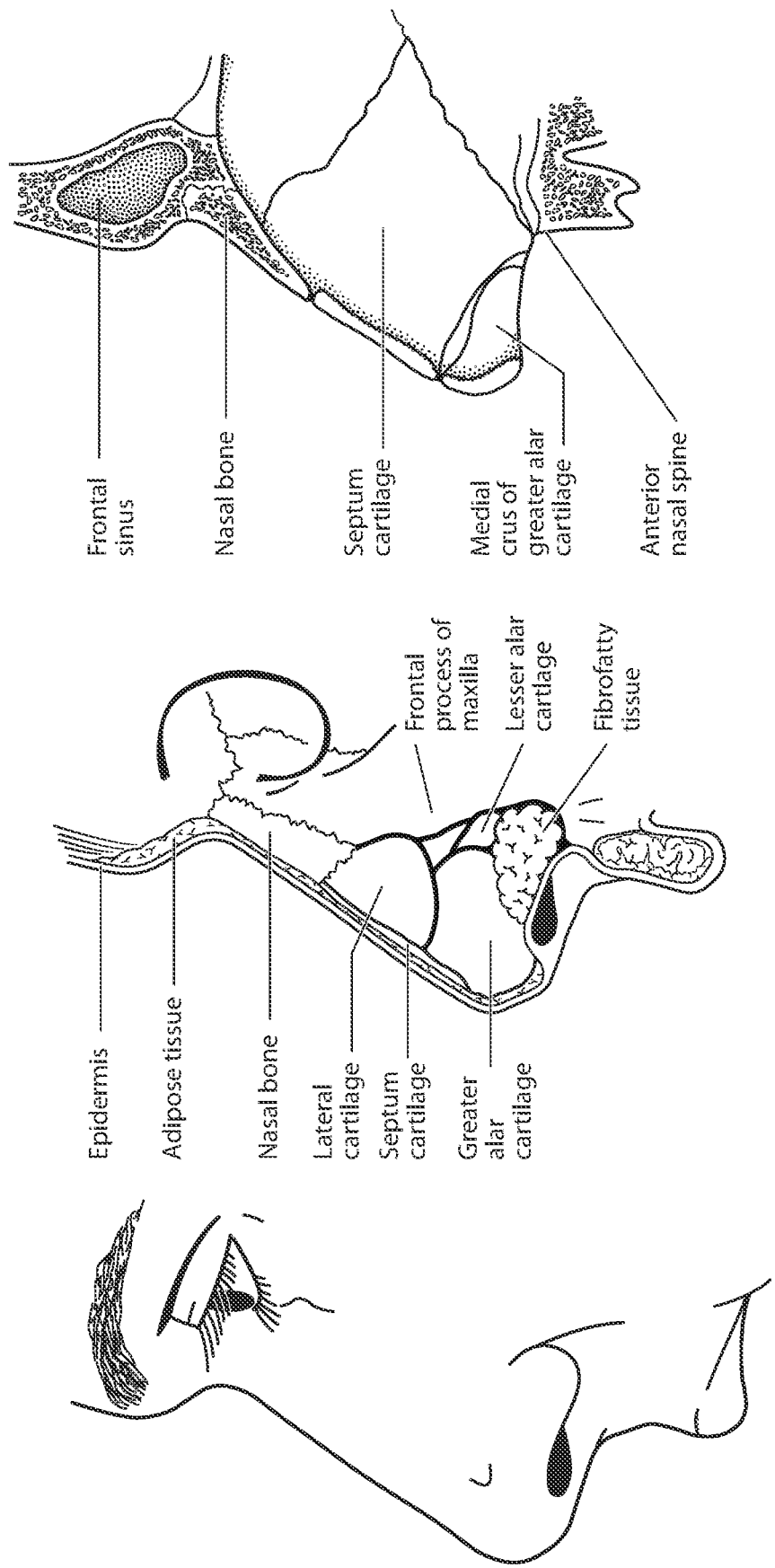

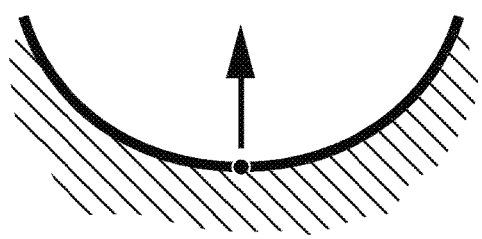
FIG. 3B — Relatively Large Positive Curvature
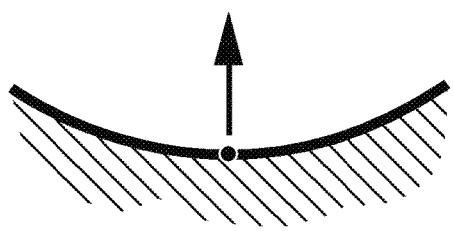
FIG. 3C — Relatively Small Positive Curvature
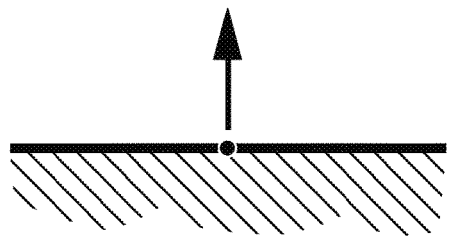
FIG. 3D — Zero Curvature
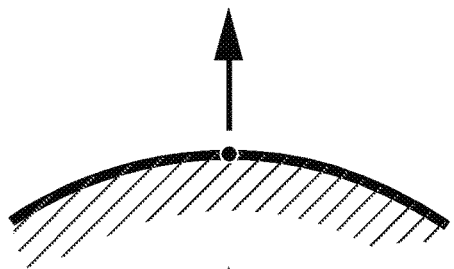
FIG. 3E — Relatively Small Negative Curvature
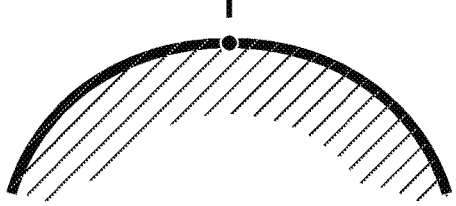
FIG. 3F — Relatively Large Negative Curvature
Copyright 2015 ResMed Limited

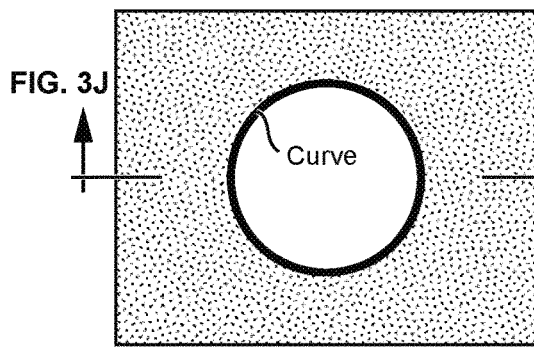
FIG. 3I
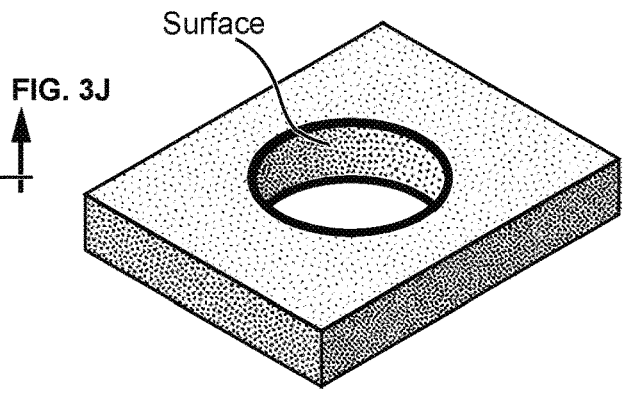
FIG. 3K
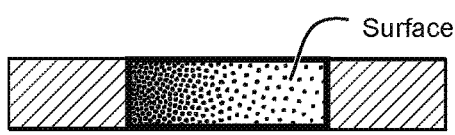
FIG. 3J
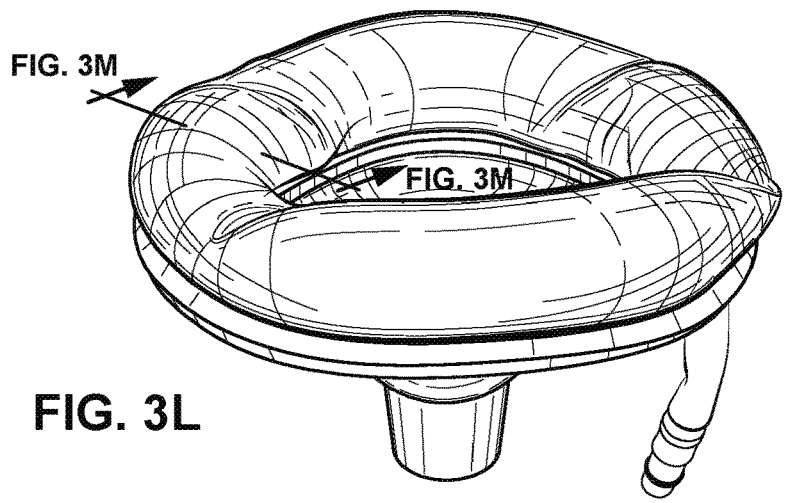
FIG. 3L
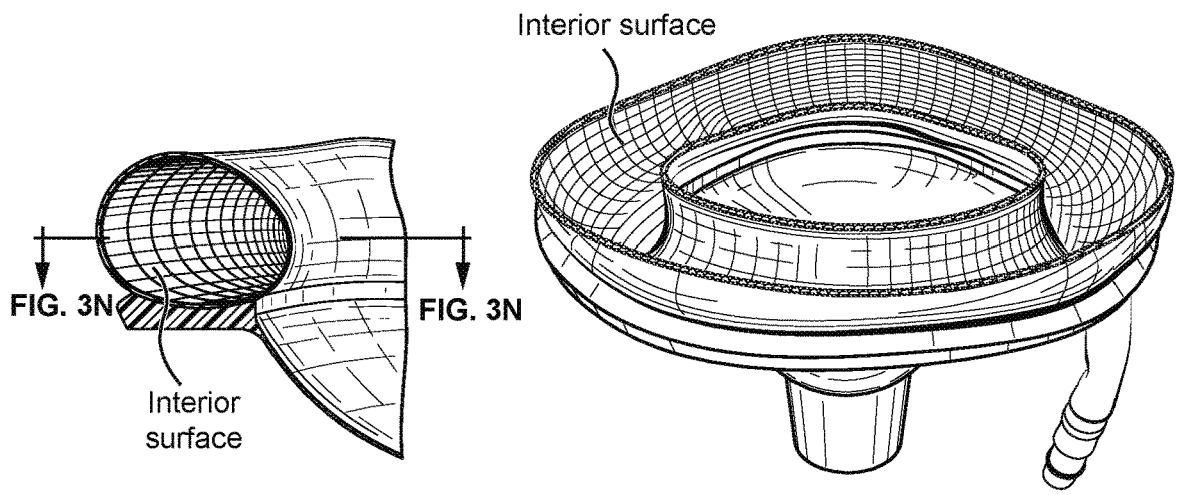
FIG. 3M  FIG. 3N

Left-hand rule
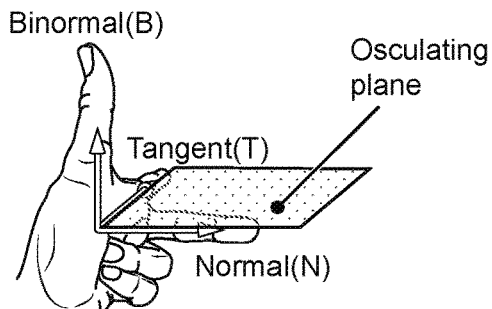
FIG. 3O
Right-hand rule
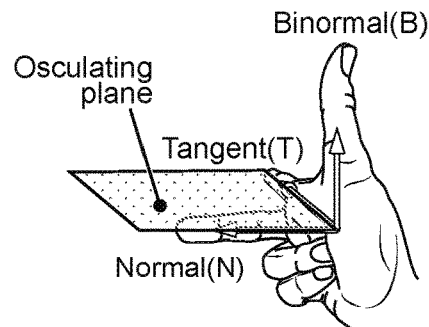
FIG. 3P
Left ear helix
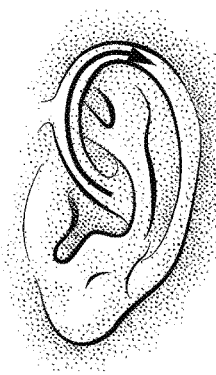
FIG. 3Q
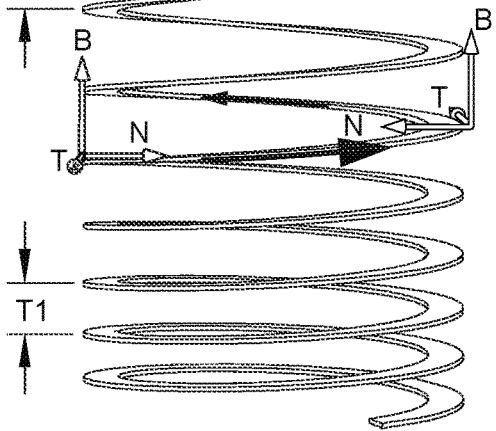
Right-hand helix
Right-hand positive
FIG. 3S
Right ear helix
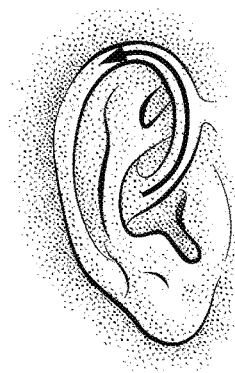
FIG. 3R
FIG. 3T
Copyright 2015 ResMed Limited

ORO-NASAL PATIENT INTERFACE

1 CROSS-REFERENCE TO RELATED APPLICATION

This application is the U.S. national phase of International Application No. PCT/AU2020/050953 filed Sep. 9, 2020 which designated the U.S. and claims priority to U.S. Provisional Patent Application No. 63/058,001 filed Jul. 29, 2020, and Australian Provisional Patent Application No. 2019903360 filed Sep. 10, 2019, the entire contents of each of which are hereby incorporated by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/ or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched gas at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

Another form of therapy system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063, 328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. Humidifiers therefore often have the capacity to heat the flow of air was well as humidifying it.

2.2.3.5 Oxygen Source

Experts in this field have recognized that exercise for respiratory failure patients provides long term benefits that slow the progression of the disease, improve quality of life and extend patient longevity. Most stationary forms of exercise like tread mills and stationary bicycles, however, are too strenuous for these patients. As a result, the need for mobility has long been recognized. Until recently, this mobility has been facilitated by the use of small compressed oxygen tanks or cylinders mounted on a cart with dolly wheels. The disadvantage of these tanks is that they contain a finite amount of oxygen and are heavy, weighing about 50 pounds when mounted.

Oxygen concentrators have been in use for about 50 years to supply oxygen for respiratory therapy. Traditional oxygen concentrators have been bulky and heavy making ordinary ambulatory activities with them difficult and impractical. Recently, companies that manufacture large stationary oxygen concentrators began developing portable oxygen concentrators (POCs). The advantage of POCs is that they can produce a theoretically endless supply of oxygen. In order to make these devices small for mobility, the various systems necessary for the production of oxygen enriched gas are condensed. POCs seek to utilize their produced oxygen as efficiently as possible, in order to minimise weight, size, and power consumption. This may be achieved by delivering the oxygen as series of pulses or "boli", each bolus timed to coincide with the start of inspiration. This therapy mode is known as pulsed or demand (oxygen) delivery (POD), in contrast with traditional continuous flow delivery more suited to stationary oxygen concentrators.

2.2.3.6 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.7 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.8 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH₂O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(*one specimen only, measured using test method specified in ISO 3744 in CPAP mode at 10 cmH₂O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises a patient interface comprising:

a plenum chamber pressurisable to a therapeutic pressure of at least 6 cmH₂O above ambient air pressure, said plenum chamber including a plenum chamber inlet port sized and structured to receive a flow of air at the therapeutic pressure for breathing by a patient;

a first seal-forming structure constructed and arranged to form a seal with a region of the patient's face surrounding an entrance to the patient's mouth such that the flow of air at said therapeutic pressure is delivered to the mouth, the first seal-forming structure constructed and arranged to maintain said therapeutic pressure in the plenum chamber throughout the patient's respiratory cycle in use;

a second seal-forming structure constructed and arranged to form a seal with a region of the patient's face surrounding an entrance to the patient's nose such that the flow of air at said therapeutic pressure is delivered to the nose, the second seal-forming structure constructed and arranged to maintain said therapeutic pressure in the plenum chamber throughout the patient's respiratory cycle in use; and a vent structure to allow a continuous flow of gases exhaled by the patient from an interior of the plenum chamber to vent to ambient, said vent structure being sized and shaped to maintain the therapeutic pressure in the plenum chamber in use;

the patient interface further comprising:

a pair of support portions provided on opposite sides of the interface between the second seal forming structure and an anterior wall of the plenum chamber, wherein the support portions are configured to oppose compression in the anterior-posterior direction.

In embodiments:

a) the support portions are connected to portions of the second seal forming structure which seal, in use, against the patient's lip superior;
b) the support portions are connected to portions of the second seal forming structure which, in use, seal to the patient's lip superior, directly inferior to the lower corners of the patient's nose;
c) the support portions are curved when viewed in cross-section parallel to a sagittal plane;
d) the support portions are curved when viewed in cross-section parallel to a frontal plane;
e) the plenum chamber comprises an oral portion and a nasal portion;
f) each support portion is connected to the oral portion of the plenum chamber adjacent a boundary of a lateral side wall portion of the oral portion and a lateral side wall portion of the nasal portion;
g) each support portion is connected to the oral portion of the shell adjacent a boundary of an anterior wall portion of the oral portion and an anterior wall portion of the nasal portion;
h) the lateral side wall portions of the plenum chamber curve inwardly adjacent the boundary with the nasal portion, wherein each support portion is substantially contiguous with an adjacent lateral side wall portion;
i) the second seal-forming structure comprises at least one nasal aperture configured to deliver a flow of air at said therapeutic pressure to an entrance to the patient's nares, wherein, in use no part of either support portion is directly inferior to the or each nasal aperture;
j) the interface further comprises a positioning and stabilising structure configured to generate a force to hold the seal-forming structure in a therapeutically effective position on the patient's head;
k) the plenum chamber is at least partially formed by a shell and the vent structure is provided to the shell; and/or
l) the support portions are connected to the second seal forming structure and are connected to the anterior wall of the plenum chamber.

Another form of the technology comprises a patient interface comprising:

a plenum chamber pressurisable to a therapeutic pressure of at least 6 cmH$_2$O above ambient air pressure, said plenum chamber including a plenum chamber inlet port sized and structured to receive a flow of air at the therapeutic pressure for breathing by a patient;

a first seal-forming structure connected to an oral portion of the plenum chamber, the first seal-forming structure constructed and arranged to form a seal with a region of the patient's face surrounding an entrance to the patient's mouth such that the flow of air at said therapeutic pressure is delivered to the mouth, the first seal-forming structure constructed and arranged to maintain said therapeutic pressure in the plenum chamber throughout the patient's respiratory cycle in use;

a second seal-forming structure connected to a nasal portion of the plenum chamber, the second seal-forming structure constructed and arranged to form a seal with a region of the patient's face surrounding an entrance to the patient's nose such that the flow of air at said therapeutic pressure is delivered to the nose, the second seal-forming structure constructed and arranged to maintain said therapeutic pressure in the plenum chamber throughout the patient's respiratory cycle in use; and a vent structure to allow a continuous flow of gases exhaled by the patient from an interior of the plenum chamber to vent to ambient, said vent structure being sized and shaped to maintain the therapeutic pressure in the plenum chamber in use;

wherein a first anterior wall portion of the nasal portion of the plenum chamber, adjacent a boundary with the oral portion of the plenum chamber, is more flexible than an immediately adjacent region of the oral portion of the plenum chamber, and a second anterior wall portion of the nasal portion of the plenum chamber, which is immediately adjacent the first anterior wall portion and is on an opposite side of the first anterior wall portion to the boundary with the oral portion of the plenum chamber, is less flexible than the immediately adjacent portions of the anterior wall.

In examples:

a) the first anterior wall portion is thinner than the immediately adjacent portions of the plenum chamber wall;
b) the second anterior wall portion is thicker than the immediately adjacent portions of the plenum chamber wall;
c) the first and second anterior wall portions are made from the same material;
d) the first anterior wall portion extends across substantially an entire width of the nasal portion of the plenum chamber;
e) the second anterior wall portion extends across at least a majority of a width of the nasal portion of the plenum chamber;
f) the first anterior wall portion extends in a superior direction around at least one lateral edge of the second anterior wall portion;
g) the second anterior wall portion extends across substantially an entire width of the nasal portion of the plenum chamber;
h) a central portion of the first anterior wall portion extends further in the superior direction than lateral portions of the first anterior wall portion;
I) an upper boundary of the first anterior wall portion is curved;

j) a lower boundary of the first anterior wall portion is curved;
k) the plenum chamber is at least partially formed by a shell and the vent structure is provided to the shell;
l) the second anterior wall portion includes a band that extends past the first anterior wall portion, and is configured to extend toward the patient, through the plenum chamber;
m) a transition within the plenum chamber between the first anterior wall portion and the second anterior wall portion is a substantially stepped surface;
n) a transition outside of the plenum chamber between the first anterior wall portion and the second anterior wall portion is a substantially smooth surface; and/or
o) the first anterior wall portion extends further superior than at least a portion of the band, in use.

Another form of the technology comprises a patient interface comprising:

a plenum chamber pressurisable to a therapeutic pressure of at least 6 cmH$_2$O above ambient air pressure, said plenum chamber including a plenum chamber inlet port sized and structured to receive a flow of air at the therapeutic pressure for breathing by a patient;

a first seal-forming structure connected to an oral portion of the plenum chamber, the first seal-forming structure constructed and arranged to form a seal with a region of the patient's face surrounding an entrance to the patient's mouth such that the flow of air at said therapeutic pressure is delivered to the mouth, the first seal-forming structure constructed and arranged to maintain said therapeutic pressure in the plenum chamber throughout the patient's respiratory cycle in use;

a second seal-forming structure connected to a nasal portion of the plenum chamber, the second seal-forming structure constructed and arranged to form a seal with a region of the patient's face surrounding an entrance to the patient's nose such that the flow of air at said therapeutic pressure is delivered to the nose, the second seal-forming structure constructed and arranged to maintain said therapeutic pressure in the plenum chamber throughout the patient's respiratory cycle in use; and a vent structure to allow a continuous flow of gases exhaled by the patient from an interior of the plenum chamber to vent to ambient, said vent structure being sized and shaped to maintain the therapeutic pressure in the plenum chamber in use;

wherein posterior surfaces of the lateral portions of the second seal forming structure slope in a superior-anterior direction from a boundary of the first and second seal forming structures.

In examples:
a) the slope of each lateral portion forms an angle of between 20 degrees and 90 degrees with a mid-contact plane of the mask;
b) no part of the patent interface contacts the patient's alar crest point, in use;
c) the interface is configured to prevent occlusion of the patient's nares, or to at least reduce occlusion relative to the interfaces of the prior art; and/or
d) the plenum chamber is at least partially formed by a shell and the vent structure is provided to the shell.

Another form of the technology comprises a patient interface comprising:

a plenum chamber pressurisable to a therapeutic pressure of at least 6 cmH$_2$O above ambient air pressure, said plenum chamber including a plenum chamber inlet port sized and structured to receive a flow of air at the therapeutic pressure for breathing by a patient;

a first seal-forming structure connected to an oral portion of the plenum chamber, the first seal-forming structure constructed and arranged to form a seal with a region of the patient's face surrounding an entrance to the patient's mouth such that the flow of air at said therapeutic pressure is delivered to the mouth, the first seal-forming structure constructed and arranged to maintain said therapeutic pressure in the plenum chamber throughout the patient's respiratory cycle in use;

a second seal-forming structure connected to a nasal portion of the plenum chamber, the second seal-forming structure constructed and arranged to form a seal with a region of the patient's face surrounding an entrance to the patient's nose such that the flow of air at said therapeutic pressure is delivered to the nose, the second seal-forming structure constructed and arranged to maintain said therapeutic pressure in the plenum chamber throughout the patient's respiratory cycle in use; and a vent structure to allow a continuous flow of gases exhaled by the patient from an interior of the plenum chamber to vent to ambient, said vent structure being sized and shaped to maintain the therapeutic pressure in the plenum chamber in use; wherein a boundary between the first seal-forming structure and the second seal-forming structure comprises a ridge.

In examples:
a) the ridge has a radius of curvature of less than 2 mm;
b) the ridge extends across substantially an entire boundary between the first seal forming structure and the second seal forming structure;
c) in use, the ridge engages a patient's face proximate the entrances to the nares where the ala meets the face above the lip superior;
d) the ridge resists creases forming in the first and/or second seal forming structure adjacent the ridge; and/or
e) in use the plenum chamber is at least partially formed by a shell and the vent structure is provided to the shell.

Another form of the technology comprises a patient interface comprising:

a plenum chamber pressurisable to a therapeutic pressure of at least 6 cmH$_2$O above ambient air pressure, said plenum chamber including a plenum chamber inlet port sized and structured to receive a flow of air at the therapeutic pressure for breathing by a patient;

a first seal-forming structure connected to an oral portion of the plenum chamber, the first seal-forming structure constructed and arranged to form a seal with a region of the patient's face surrounding an entrance to the patient's mouth such that the flow of air at said therapeutic pressure is delivered to the mouth, the first seal-forming structure constructed and arranged to maintain said therapeutic pressure in the plenum chamber throughout the patient's respiratory cycle in use;

a second seal-forming structure connected to a nasal portion of the plenum chamber, the second seal-forming structure constructed and arranged to form a seal with a region of the patient's face surrounding an entrance to the patient's nose such that the flow of air at said therapeutic pressure is delivered to the nose, the second seal-forming structure constructed and arranged to maintain said therapeutic pressure in the plenum chamber throughout the patient's respiratory cycle in use; and a vent structure to allow a continuous flow of gases exhaled by the patient from an interior of the plenum chamber to vent to ambient, said vent structure being sized and shaped to maintain the therapeutic pressure in the plenum chamber in use;

wherein, at least a portion of the oral portion of plenum chamber comprises a flexible shell, wherein the flexible shell is formed from a material having a Young's modulus of less than 0.4 GPa.

In examples:
a) the flexible shell is formed from a material having a Young's modulus less than 0.1 GPa, preferably between 0.3-0.7 MPa.
b) at least one component is connected to the flexible shell, wherein the at least one component is stiffer than a portion of the flexible shell adjacent the component;
c) the at least one component comprises one or more of: a vent module; a headgear connector; a headgear connector connected to a rigidizing arm; a rigidizing member; a less flexible shell portion;
d) the at least one component is releasably connectable to the flexible shell;
e) the at least one component is permanently connected to the flexible shell;
f) the at least one component is overmoulded to the flexible shell;
g) the flexible shell comprises stiffening portions having greater thickness than immediately adjacent portions of the flexible shell;
h) the at least one component is configured as stiffening ribs or bands;
i) a central portion of the oral portion of the plenum chamber has a greater stiffness than the remainder of the plenum chamber; and/or
j) the plenum chamber is at least partially formed by a shell and the vent structure is provided to the shell.

Another form of the technology comprises a patient interface comprising:
a plenum chamber including a cavity that is pressurisable to a therapeutic pressure of at least 6 cmH$_2$O above ambient air pressure, said plenum chamber including a plenum chamber inlet port sized and structured to receive a flow of air at the therapeutic pressure for breathing by a patient;
a first seal-forming structure constructed and arranged to form a seal with a region of the patient's face surrounding an entrance to the patient's mouth such that the flow of air at said therapeutic pressure is delivered to the mouth, the first seal-forming structure constructed and arranged to maintain said therapeutic pressure in the plenum chamber throughout the patient's respiratory cycle in use;
a second seal-forming structure constructed and arranged to form a seal with a region of the patient's face surrounding an entrance to the patient's nose such that the flow of air at said therapeutic pressure is delivered to the nose, the second seal-forming structure constructed and arranged to maintain said therapeutic pressure in the plenum chamber throughout the patient's respiratory cycle in use;
a vent structure to allow a continuous flow of gases exhaled by the patient from an interior of the plenum chamber to vent to ambient, said vent structure being sized and shaped to maintain the therapeutic pressure in the plenum chamber in use; and
a positioning and stabilizing structure configured to maintain the first seal-forming structure and the second seal-forming structure in a therapeutically effective position, the positioning and stabilizing structure comprising:
a frame coupled to the plenum chamber, the frame including,
a central portion coupled to the plenum chamber outside of the cavity, and
a pair of arms that extend away from the central portion in a posterior direction past the second seal-forming structure, the pair of arms being more flexible than the central portion; and
headgear straps coupled to the frame, and configured to provide a tensile force to the first seal-forming structure and to the second seal-forming structure into the patient's face via the frame.

In examples:
a) each arm of the pair of arms are more flexible than the frame;
b) the central portion is thicker than the each arm of the pair of arms;
c) the central portion and each arm of the pair of arms are constructed from the same material;
d) each arm of the pair of arms includes a first connection point, the headgear straps are coupled to the first connection point of each arm;
e) the first connection points are loops, and the headgear straps are coupled to the loops so that the straps are perpendicular to an edge of each loop and apply a force vector perpendicular to the edge;
f) the first connection points are loops, and include a region of reduced thickness, a headgear strap may contact the region of reduced thickness;
g) a first magnet is overmolded onto the central portion of the frame, the headgear straps include a second magnet removably coupled to the first magnet;
h) the first magnet includes an outer casing at least partially enclosing a magnetic material, the outer casing includes a planar surface and a lip extending from the planar surface;
i) an overhang is spaced apart from the second magnet and configured to engage the lip when the second magnet is coupled to the magnetic material;
j) the plenum chamber includes a groove, the central portion positioned within the groove;
k) the central portion is removably positionable within the groove;
l) the groove includes a projection, the central portion includes a complimentary slot configured to receive the projection;
m) the slot is tapered and includes a wider opening and a narrower opening, the projection configured to be received through the wider opening before the narrower opening;
n) the projection includes an overhang configured to extend over the slot and retain the frame relative to the plenum chamber;
o) the plenum chamber includes a protrusion disposed adjacent to the groove, the protrusion configured to retain the central portion within the groove;
p) an outer surface of the central portion is flush with an outer surface of the plenum chamber, the outer surface of the central portion and the outer surface of the plenum chamber configured to face away from the patient in use;

q) the central portion includes an annular shape, the plenum chamber inlet port disposed radially within the central portion while the frame is coupled to the plenum chamber;
r) the plenum chamber inlet port is configured to receive an elbow, the elbow configured to be spaced apart from the central portion while received within the plenum chamber inlet port;
s) each arm is formed as a cantilevered structure relative to the central portion;
t) the thickness of each arm decreases from a fixed end toward a free end;
u) the arm includes a scalloped region on an inner surface configured to face the patient's skin;
v) each arm is pivotable relative to the central portion about a pivot point; and/or
w) the pivot point is a living hinge.

Another form of the technology comprises a patient interface comprising:
a plenum chamber including a cavity that is pressurisable to a therapeutic pressure of at least 6 cmH$_2$O above ambient air pressure, said plenum chamber including a plenum chamber inlet port sized and structured to receive a flow of air at the therapeutic pressure for breathing by a patient;
a seal-forming structure constructed and arranged to form a seal with a region of the patient's face such that the flow of air at said therapeutic pressure is delivered to the airways, the seal-forming structure constructed and arranged to maintain said therapeutic pressure in the plenum chamber throughout the patient's respiratory cycle in use; and
a positioning and stabilizing structure configured to maintain the seal-forming structure in a therapeutically effective position.

Another aspect of one form of the present technology is an oro-nasal patient interface that is more compact and less obtrusive to the patient.

Another aspect of one form of the present technology is an oro-nasal patient interface that has a nasal cushion portion that provides an improved fit to the lower corners of the nose.

Another aspect of one form of the present technology is an oro-nasal patient interface that reduces occlusive contact on the nose.

Another aspect of one form of the present technology is an oro-nasal patient interface that can self adjust to accommodate patients with a wide variety of nasolabial angles.

Another aspect of one form of the present technology is an oro-nasal patient interface that has a relatively flexible shell.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is conditioned in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
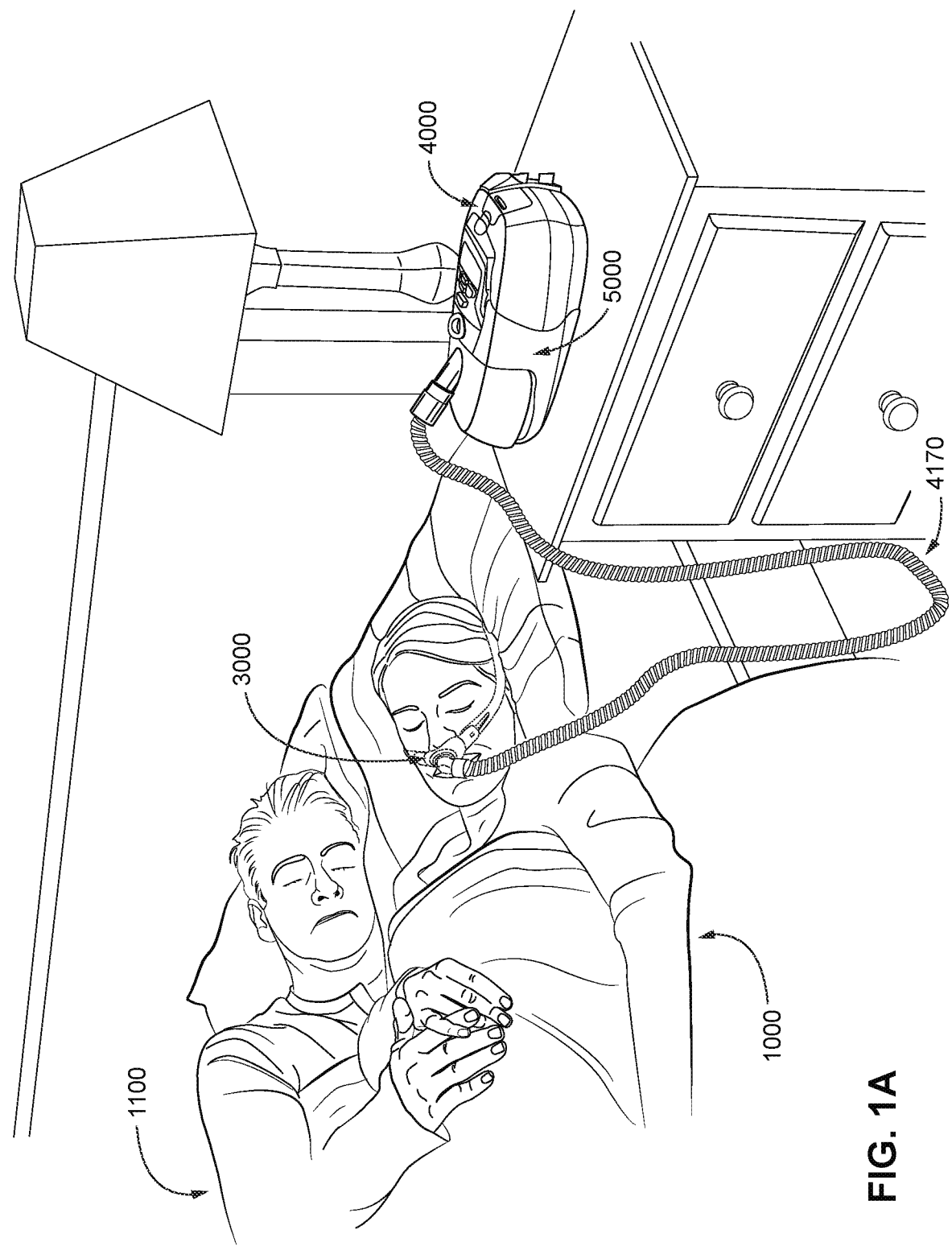
Figure 1B:
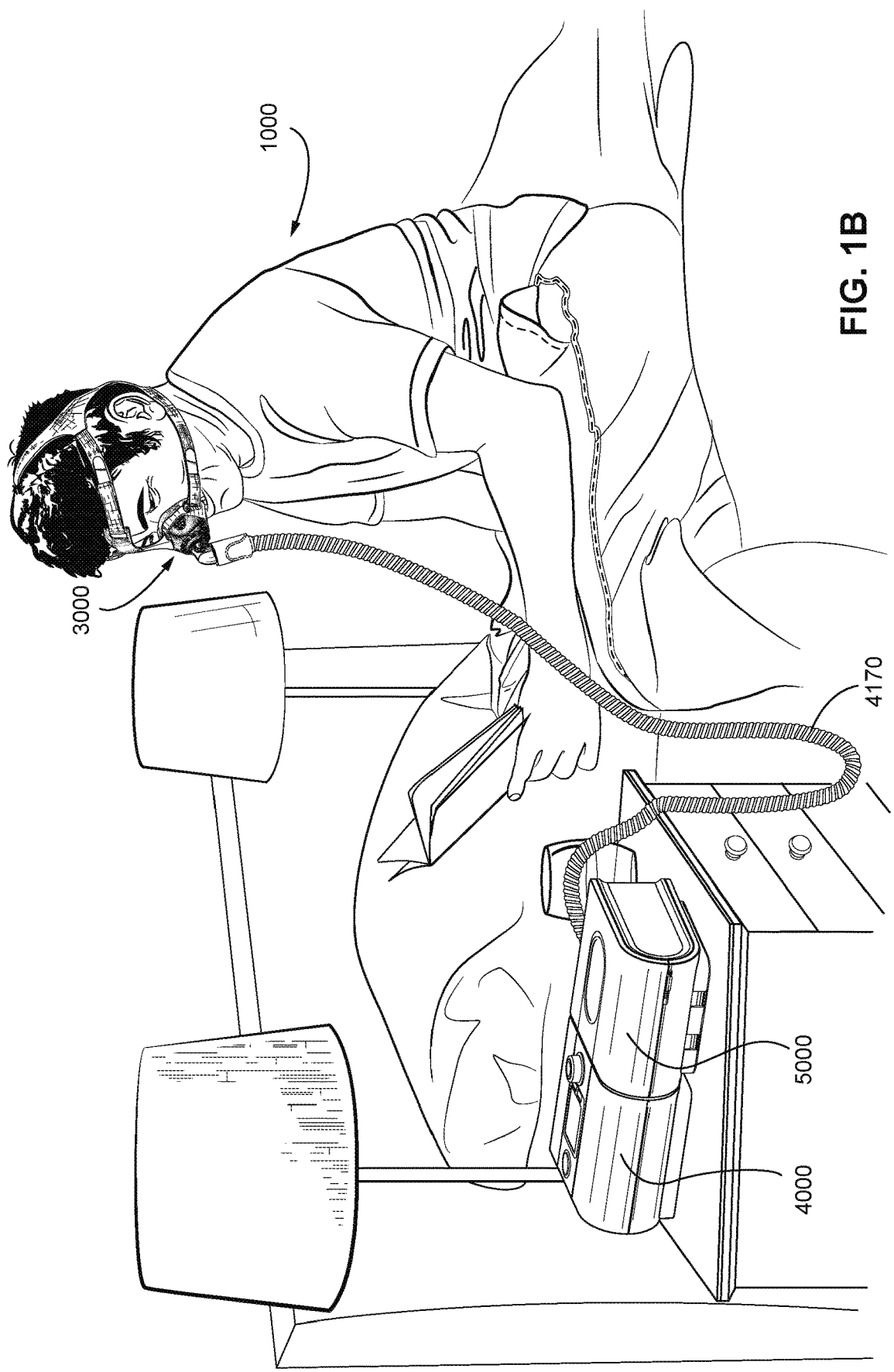
Figure 1C:
Figure 2A:
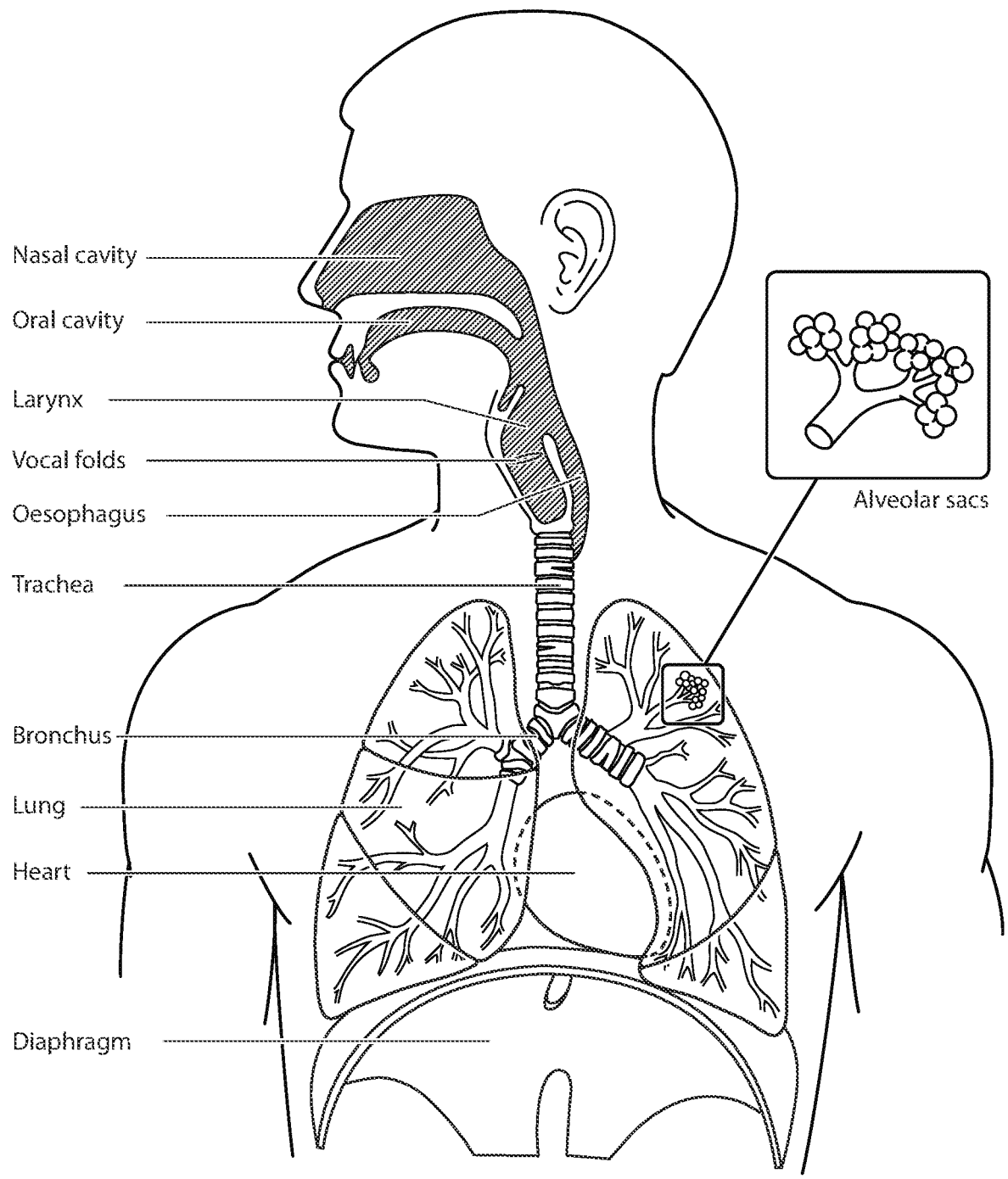
FIG. 2A shows an overview of a human respiratory system including the nasal and oral cavities, the larynx, vocal folds, oesophagus, trachea, bronchus, lung, alveolar sacs, heart and diaphragm.
Figure 2B:
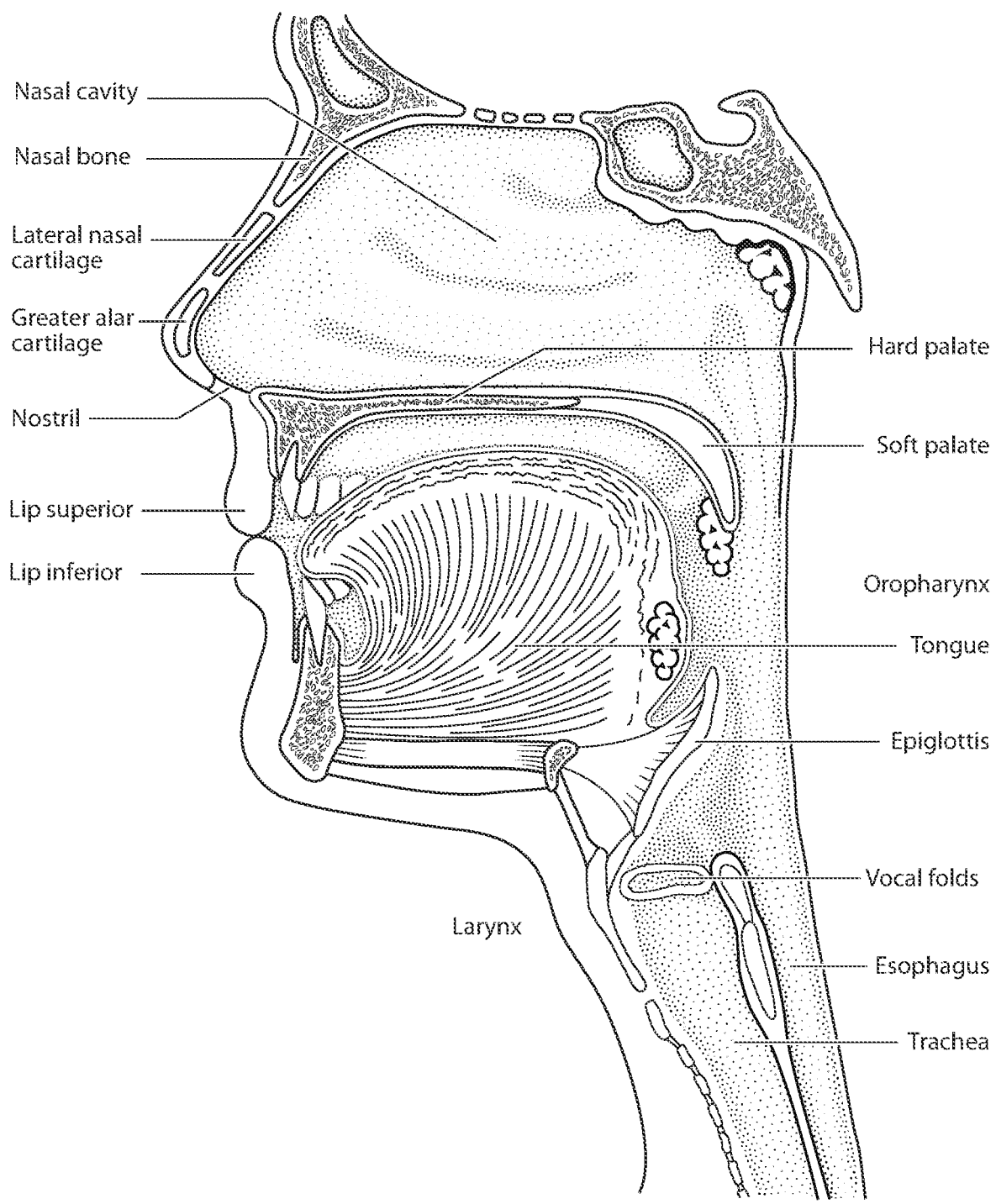
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
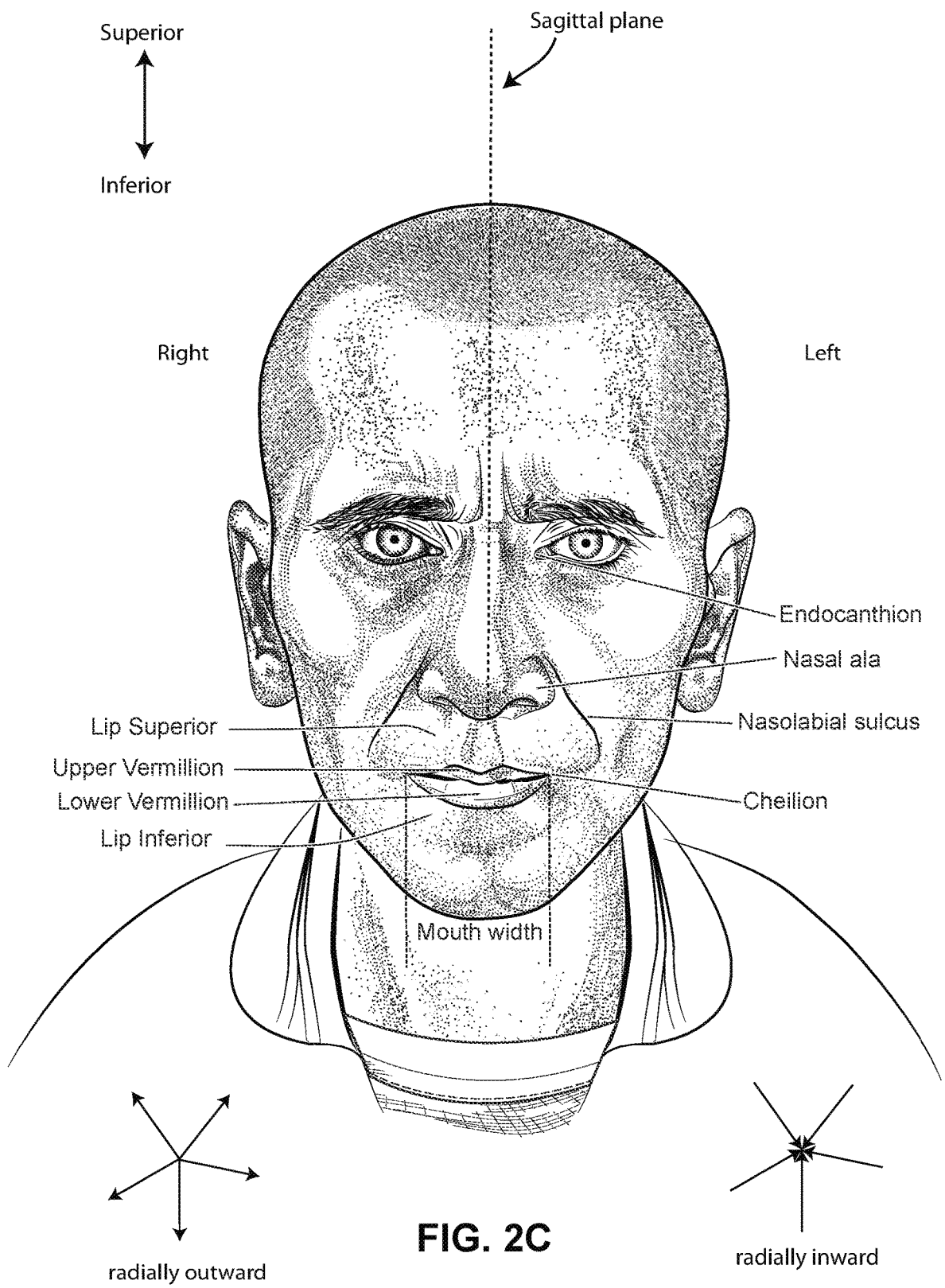
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
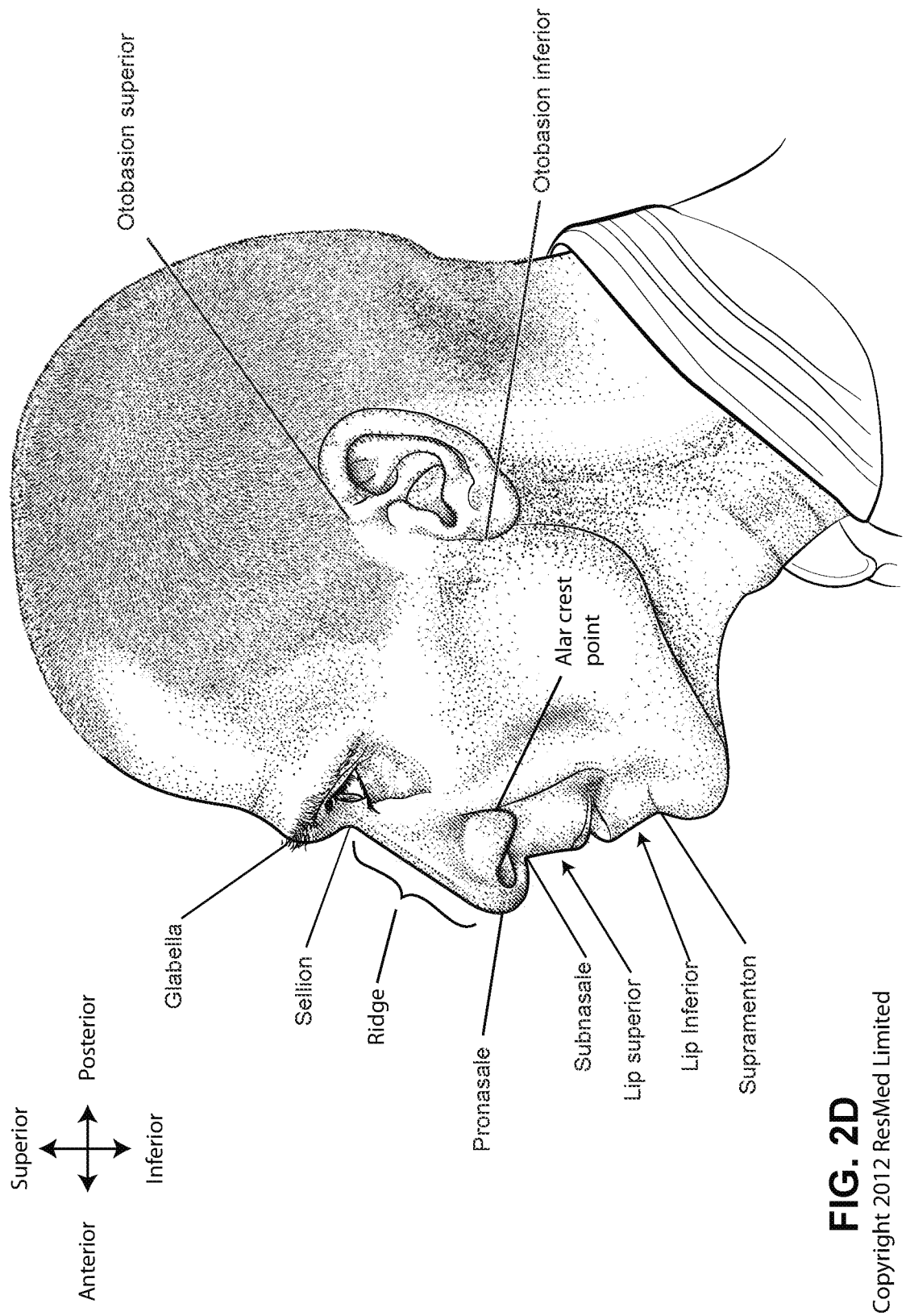
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
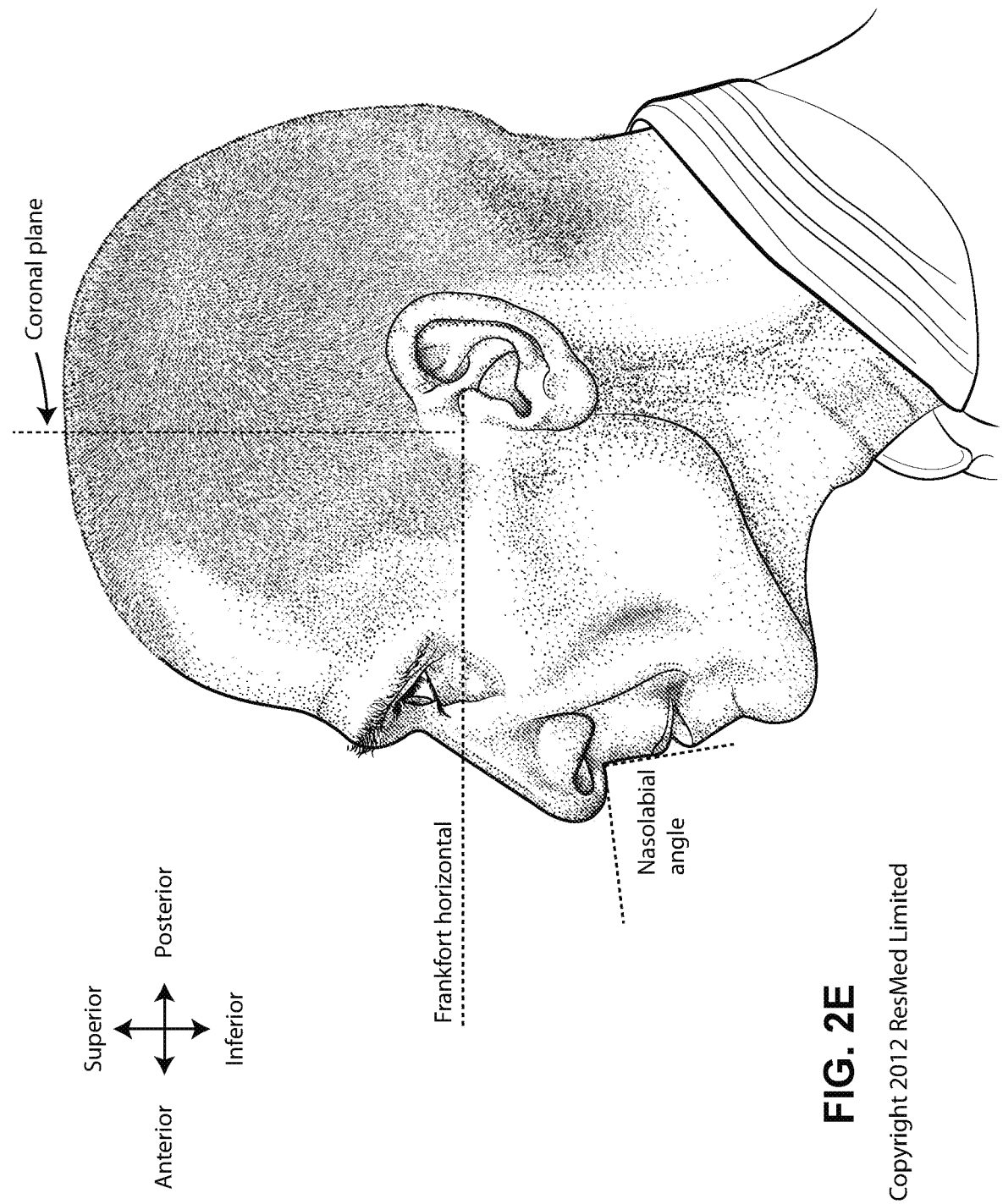

FIG. 2E is a further side view of a head. The approximate locations of the Frankfort horizontal and nasolabial angle are indicated. The coronal plane is also indicated.

Figure 2F:
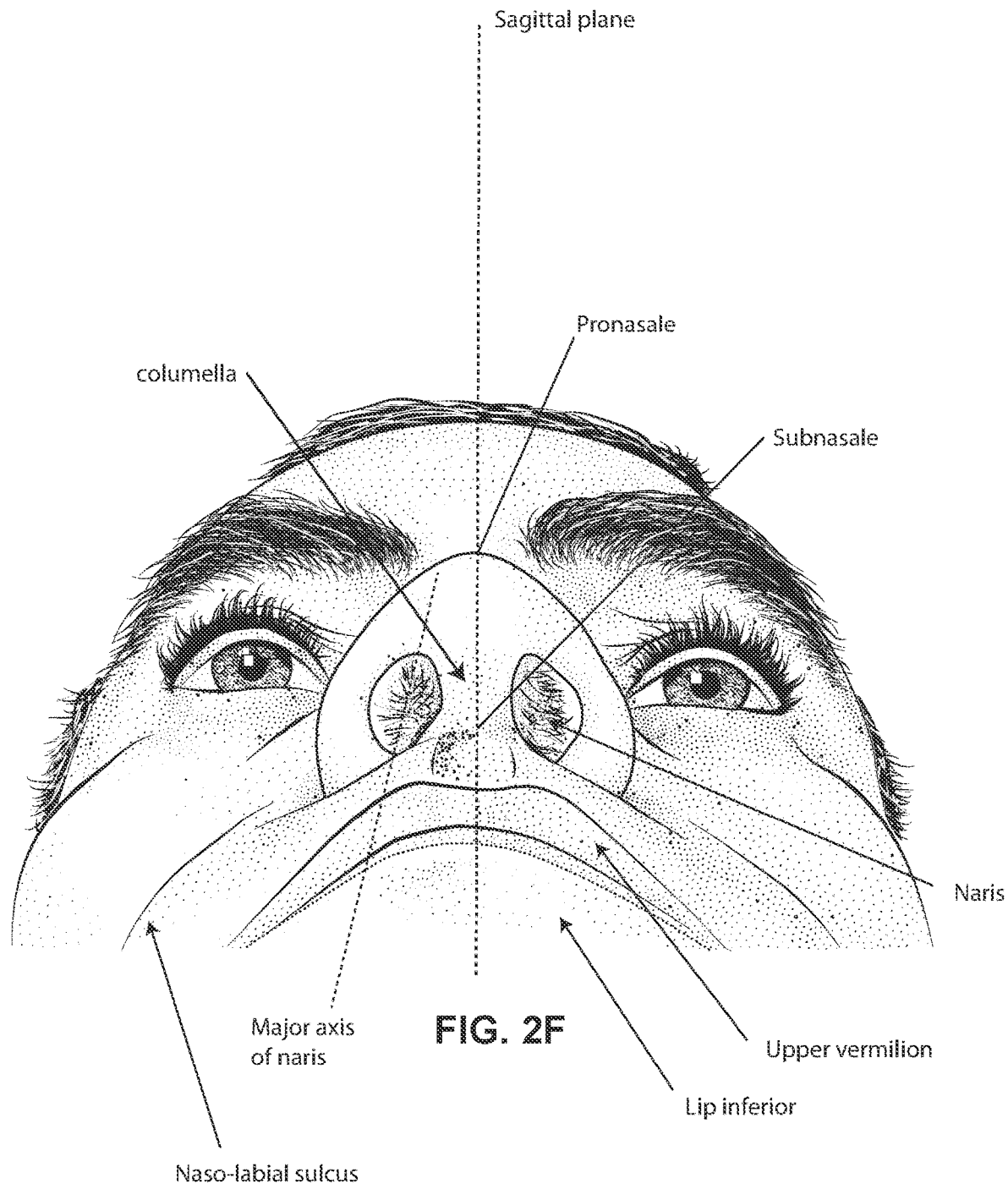

FIG. 2F shows a base view of a nose with several features identified including naso-labial sulcus, lip inferior, upper Vermilion, naris, subnasale, columella, pronasale, the major axis of a naris and the midsagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
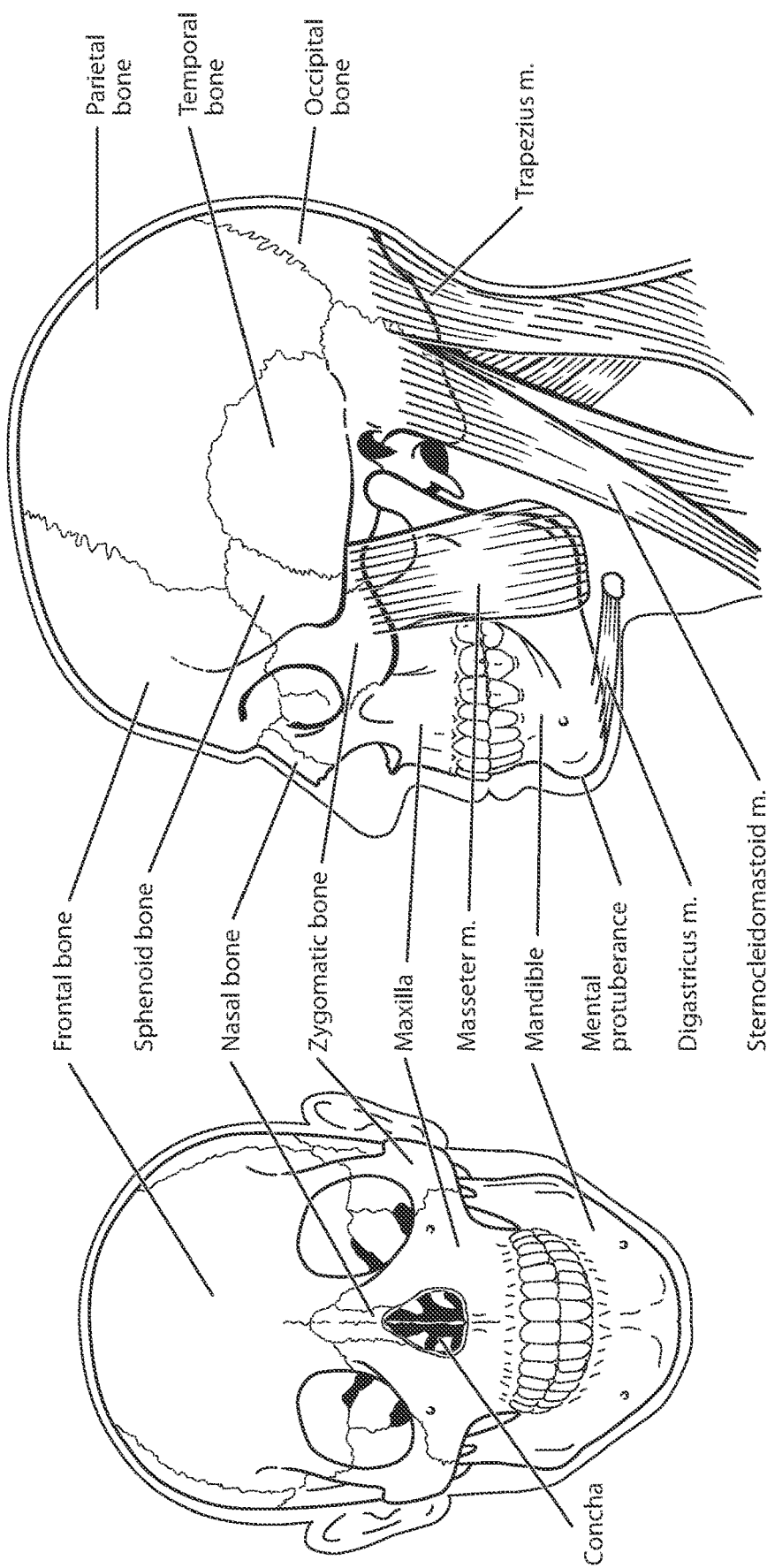

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
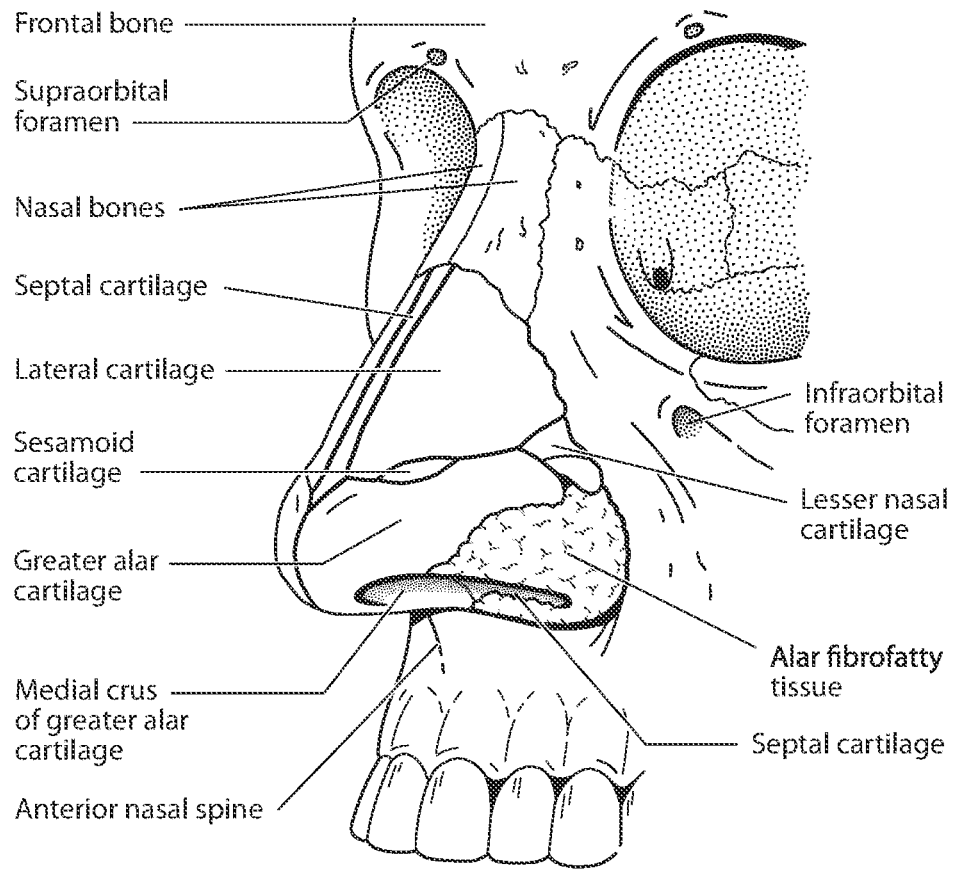

FIG. 2L shows an anterolateral view of a nose.

4.3 Patient Interface

Figure 3A:
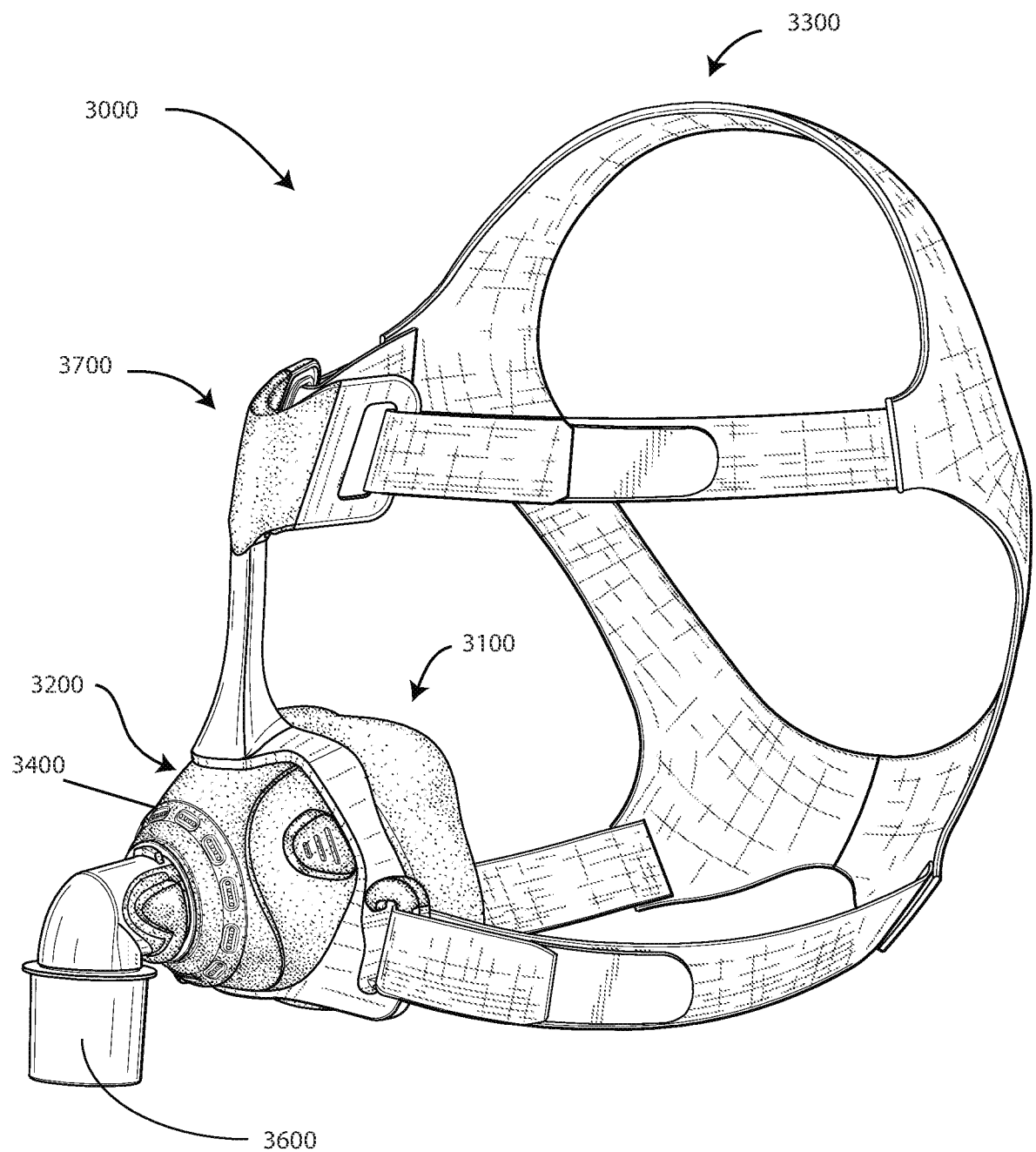

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
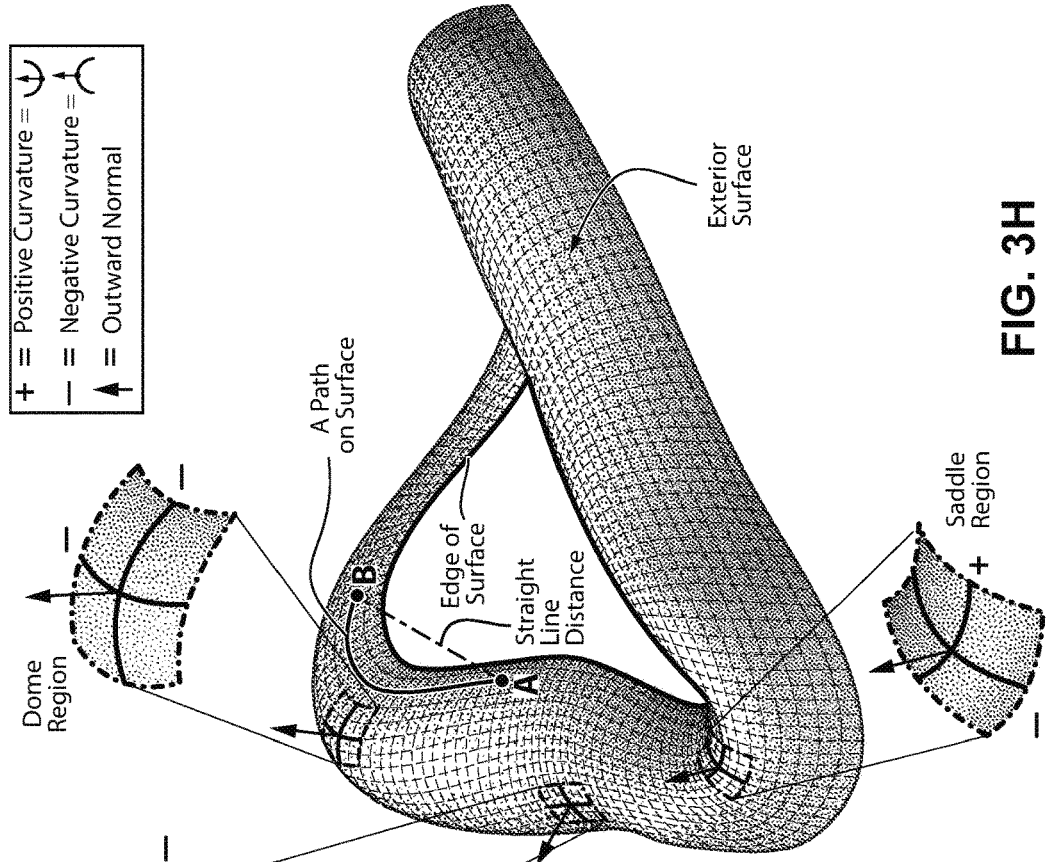
Figure 3G:
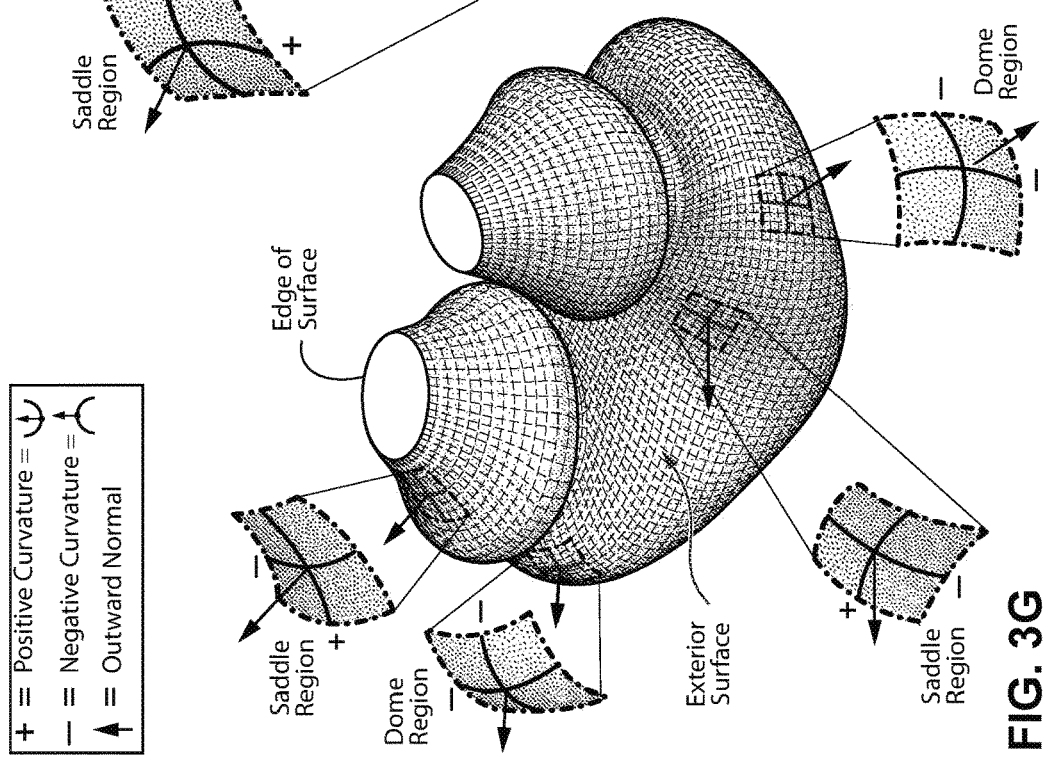

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

Figure 3U:
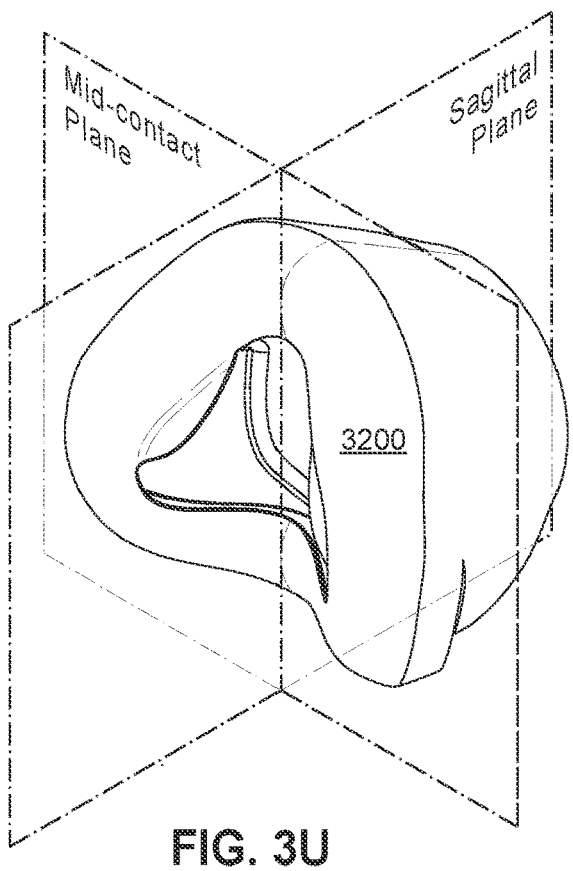

FIG. 3U shows a view of a plenum chamber 3200 showing a sagittal plane and a mid-contact plane.

Figure 3V:
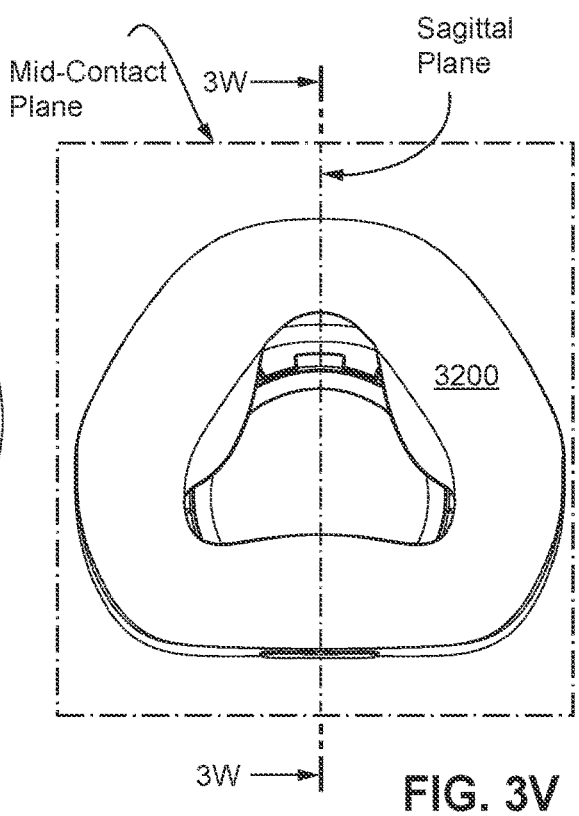

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
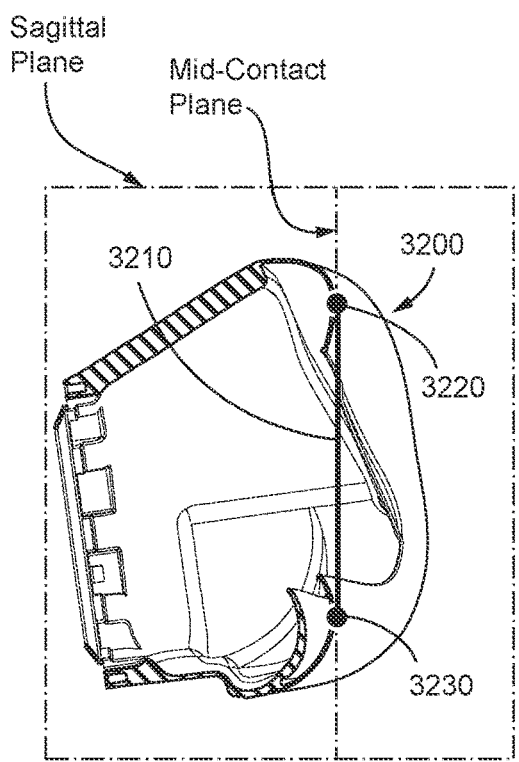

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points. For oro-nasal interfaces configured with plenum chambers having separate oral and nasal portions, for example Ultra Compact Full Face (UCFF) masks, the superior point and inferior points are on the seal forming structure of the oral portion of the mask.

Figure 3X:
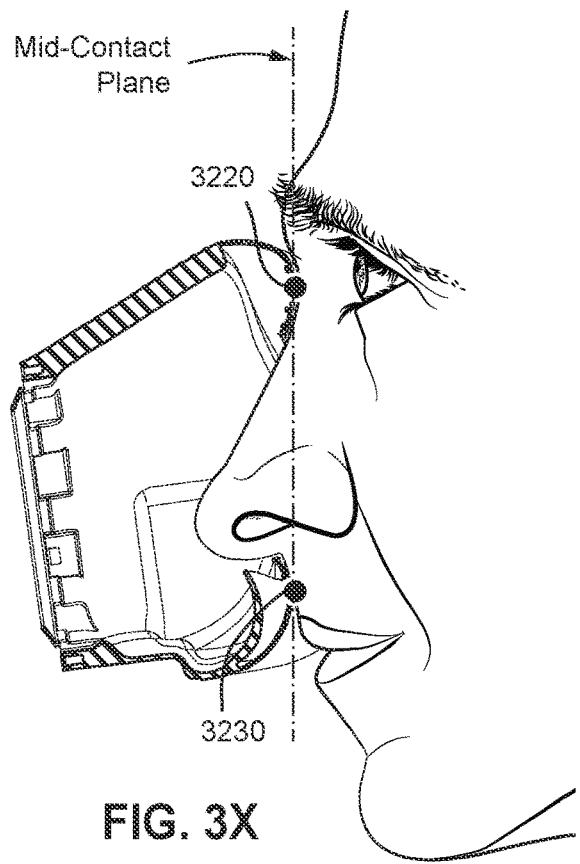

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 RPT Device

Figure 4A:
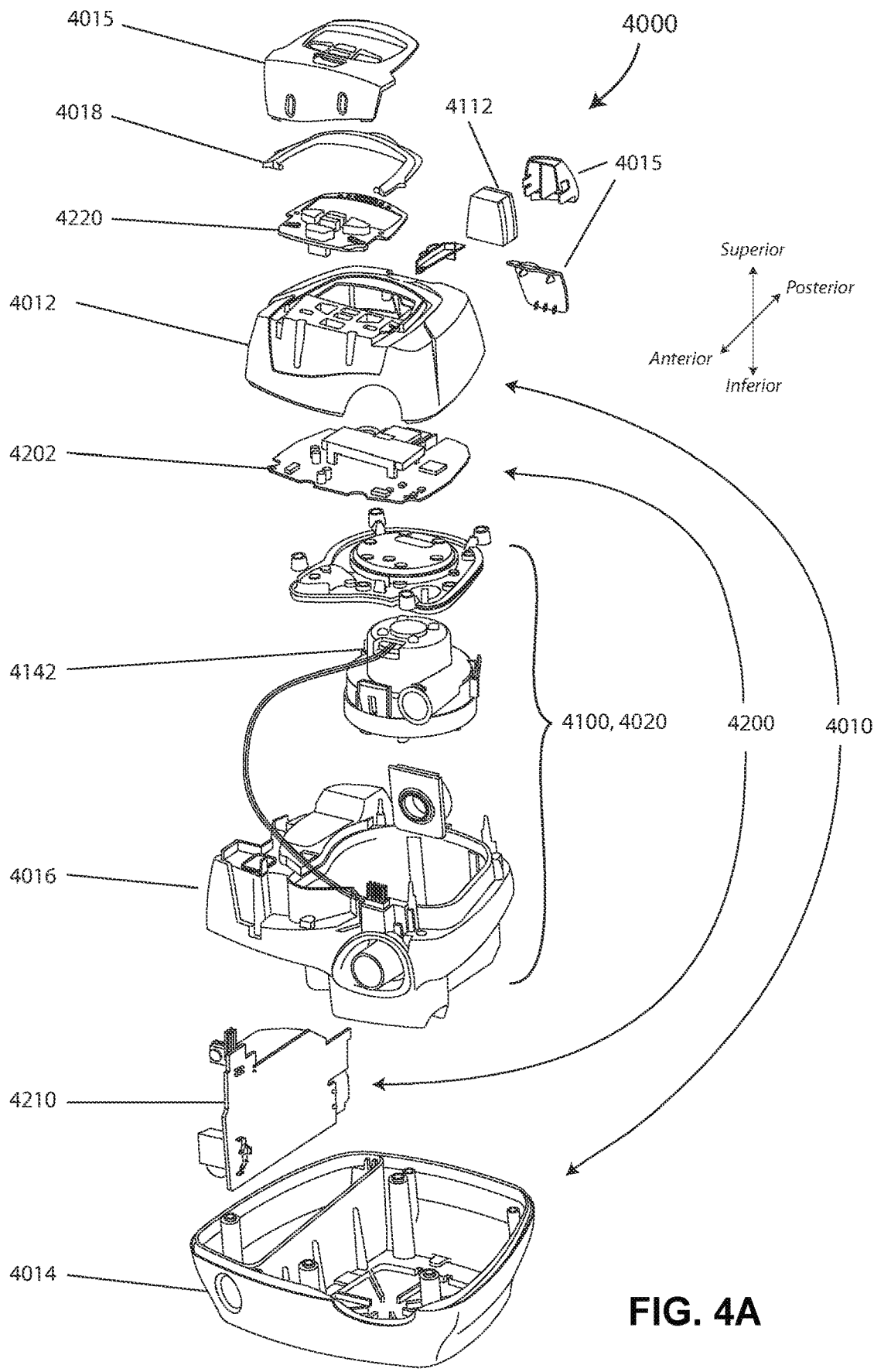

FIG. 4A shows an RPT device in accordance with one form of the present technology.

Figure 4B:
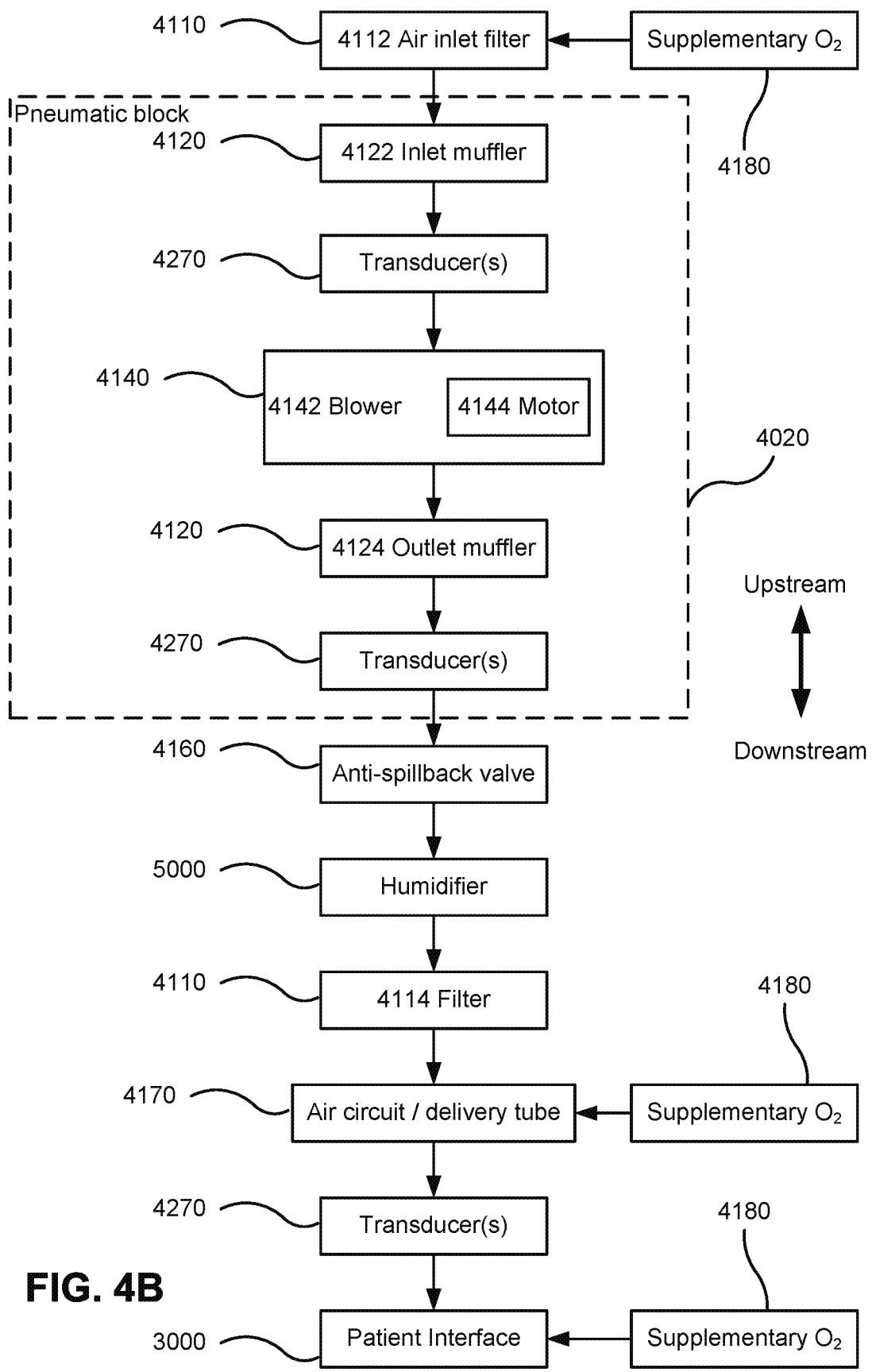

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

Figure 5A:
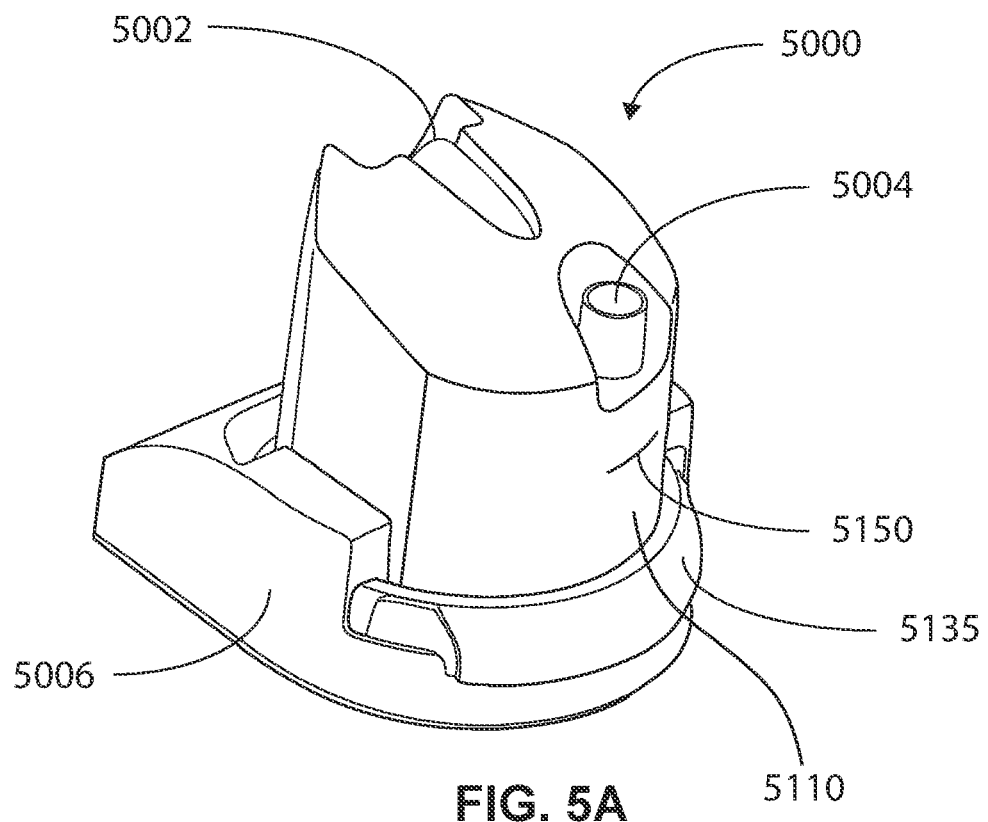

FIG. 5A shows an isometric view of a humidifier in accordance with one form of the present technology.

Figure 5B:
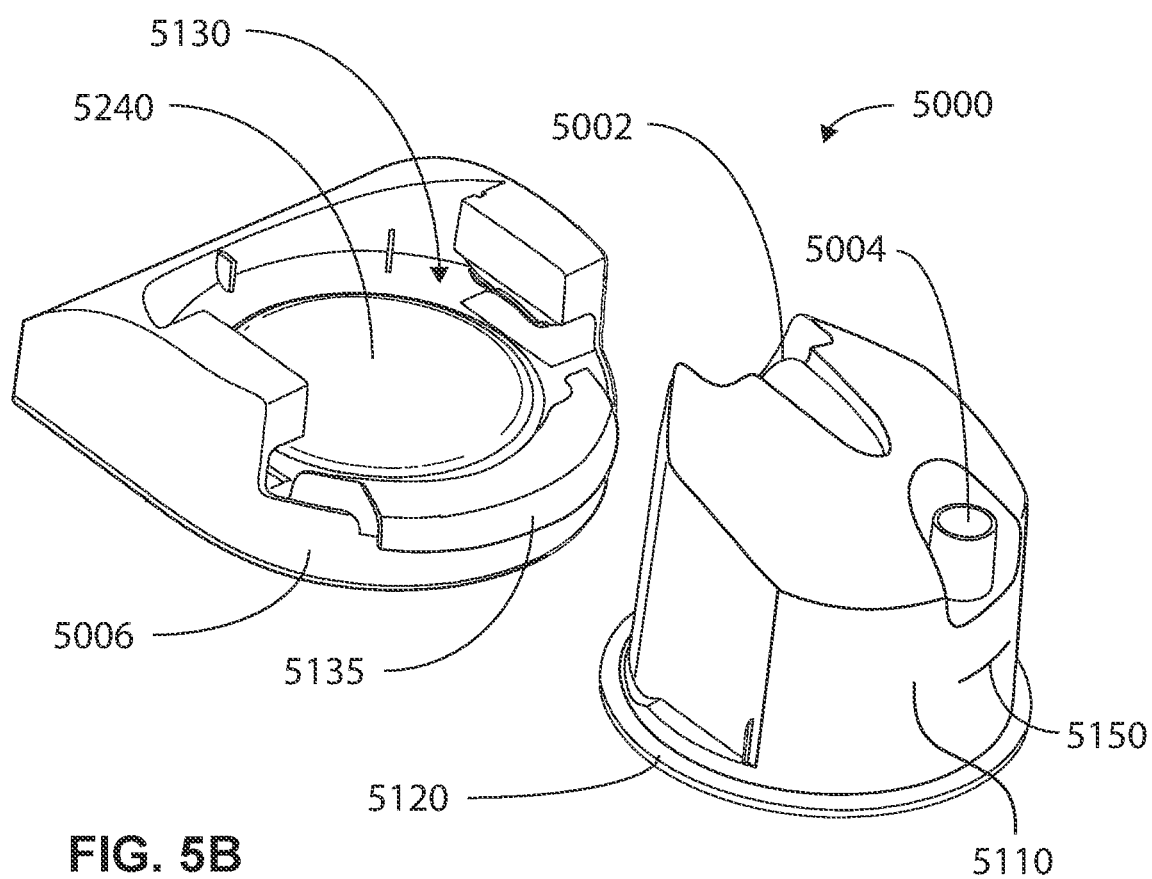

FIG. 5B shows an isometric view of a humidifier in accordance with one form of the present technology, showing a humidifier reservoir 5110 removed from the humidifier reservoir dock 5130.

4.6 Breathing Waveforms

Figure 6:
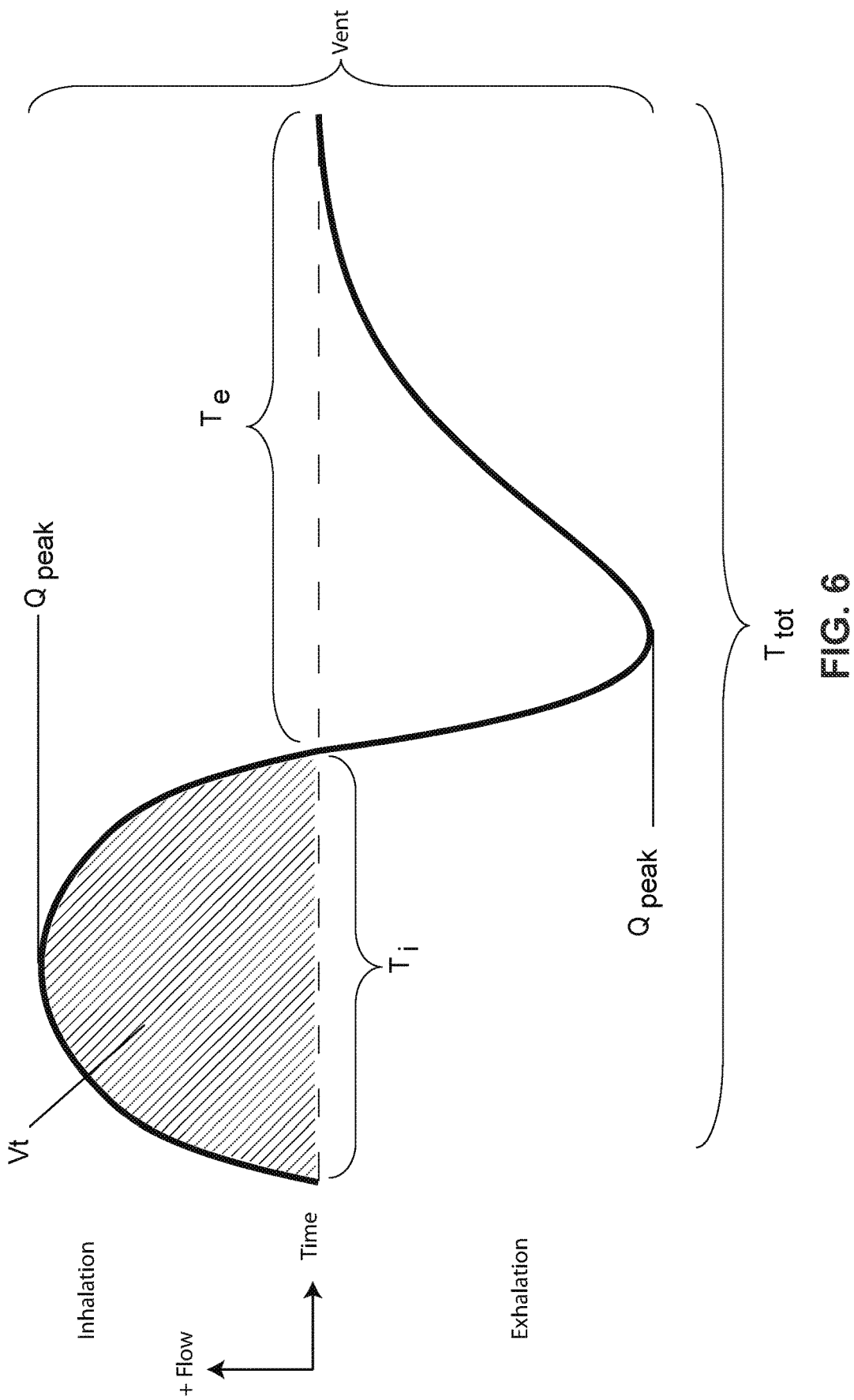

FIG. 6 shows a model typical breath waveform of a person while sleeping.

4.7 Patient Interface Examples of the Present Technology

Figure 7:
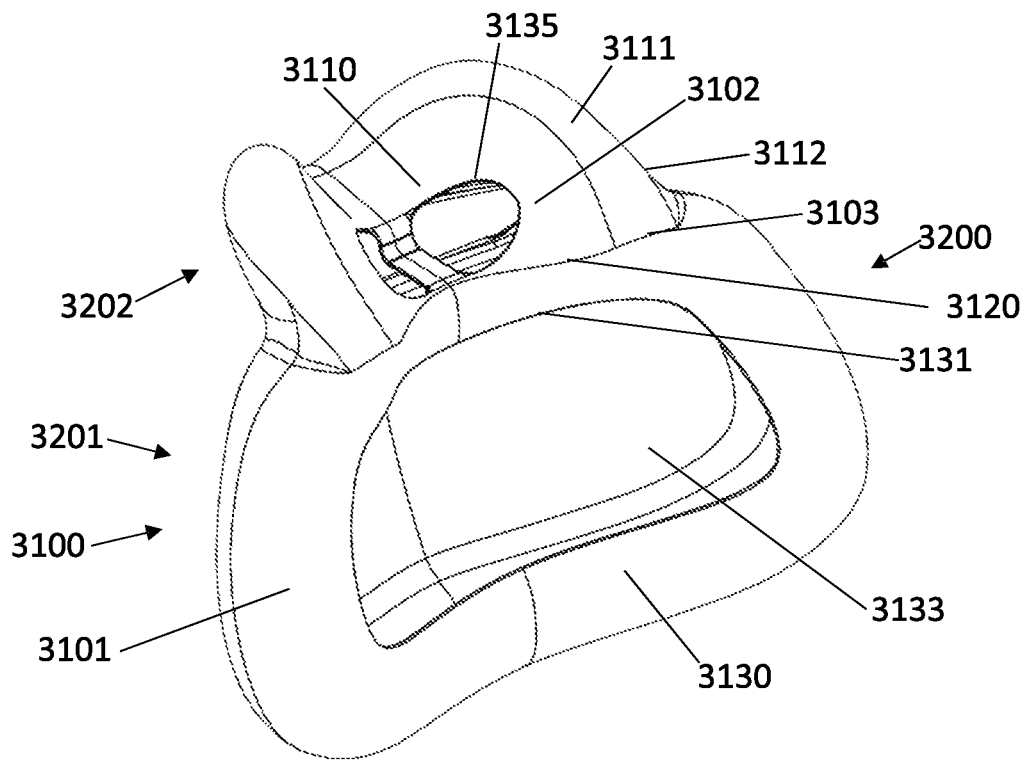

FIG. 7 is a rear perspective view of a plenum chamber in accordance with one form of the present technology, with inlet ports not shown.

Figure 8:
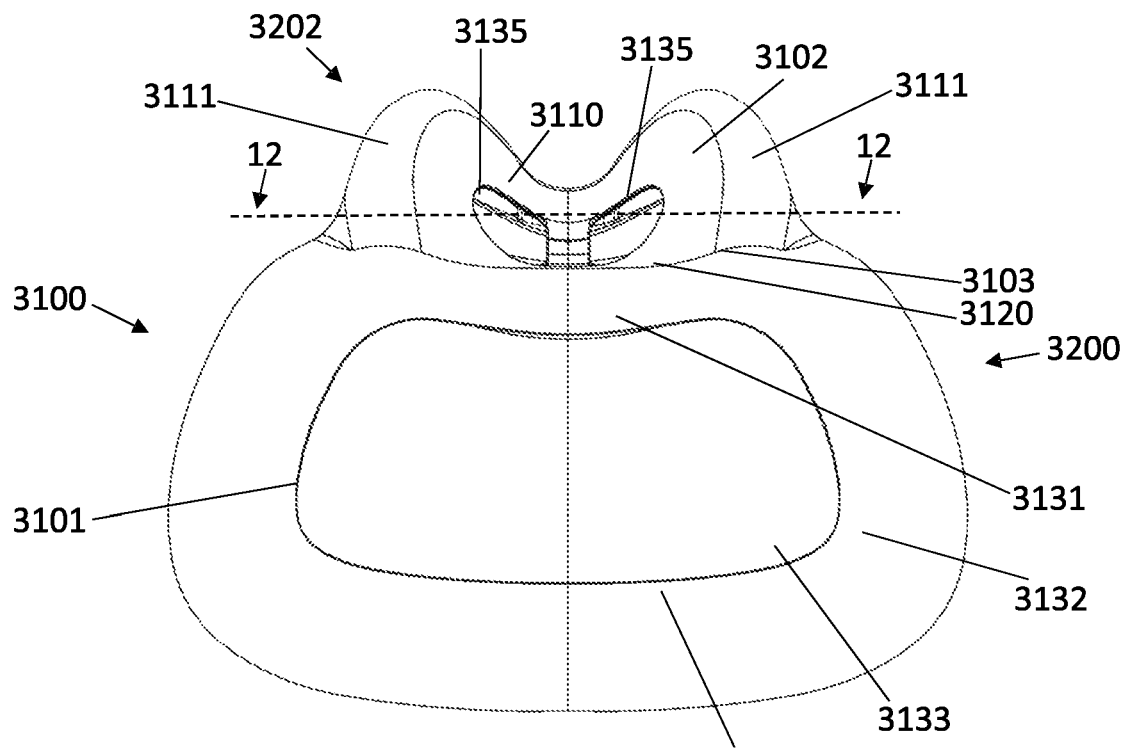

FIG. 8 is a rear view of the plenum chamber of FIG. 7.

Figure 9:
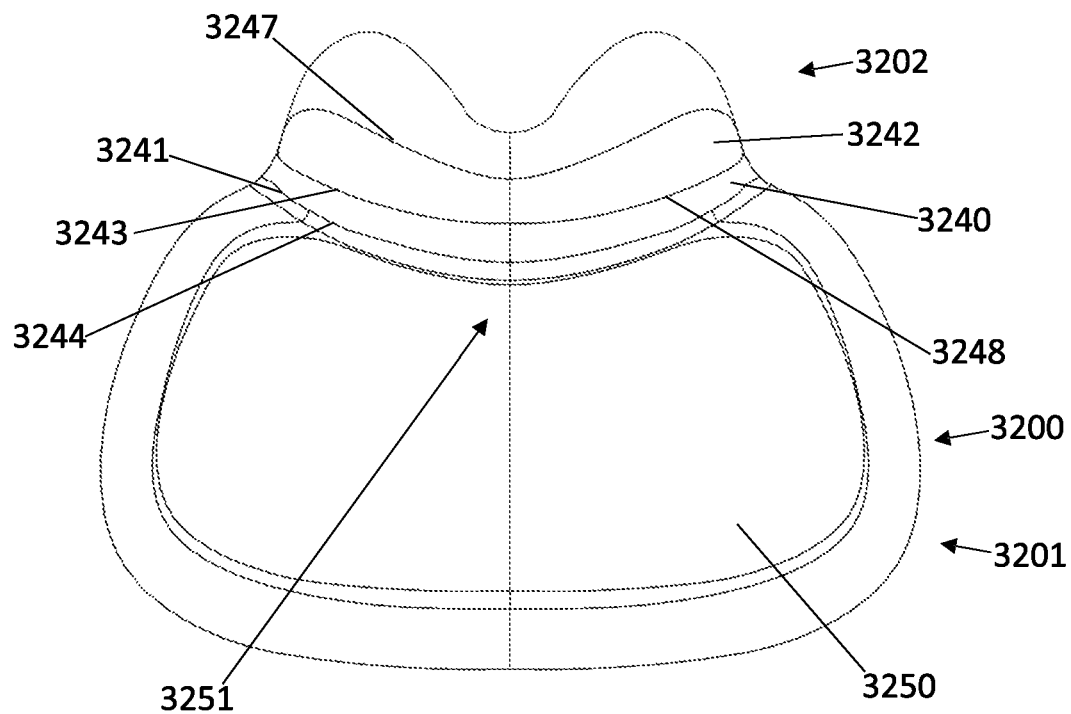

FIG. 9 is a front view of the plenum chamber of FIG. 7.

Figure 10:
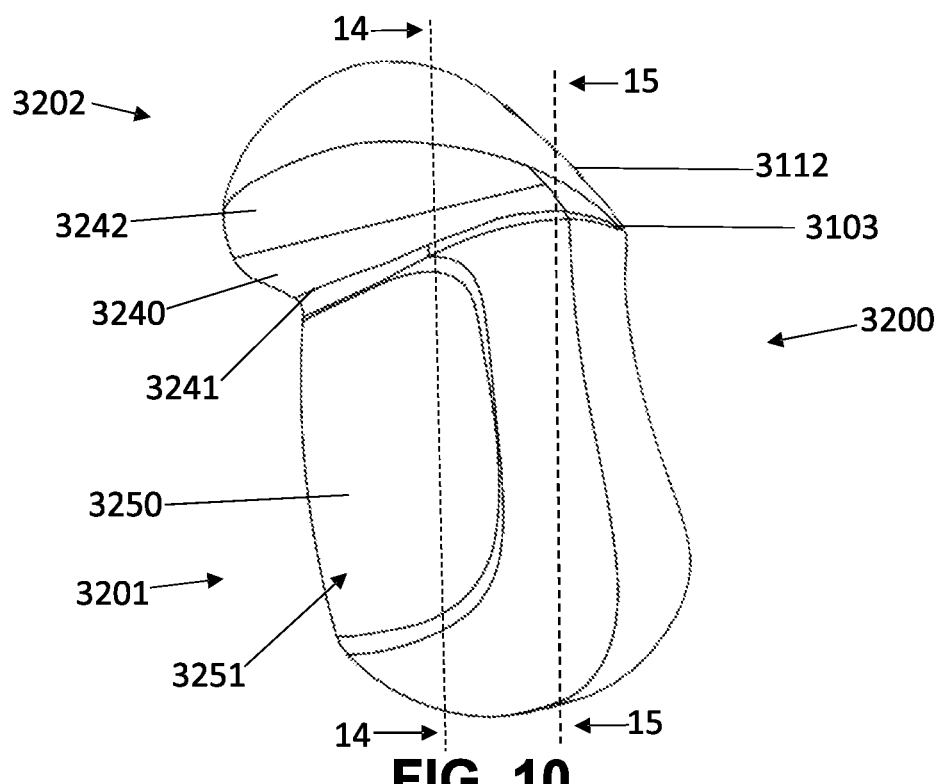

FIG. 10 is a side view of the plenum chamber of FIG. 7.

Figure 11:
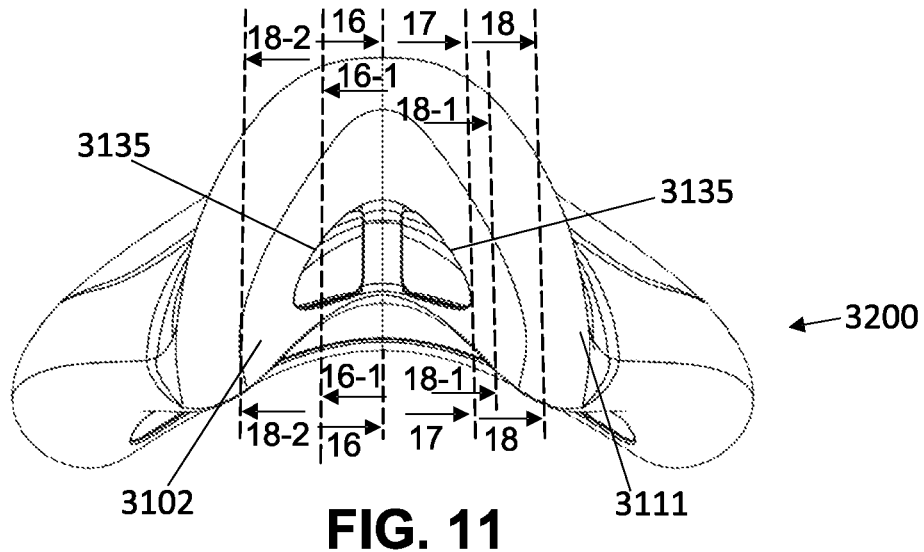

FIG. 11 is a top view of the plenum chamber of FIG. 7.

Figure 12:
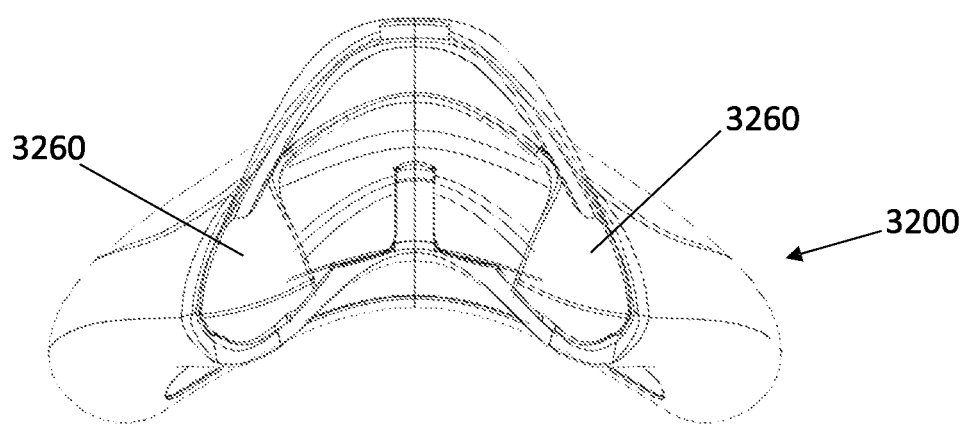

FIG. 12 is a cross-section of the plenum chamber through plane 12-12.

Figure 13:
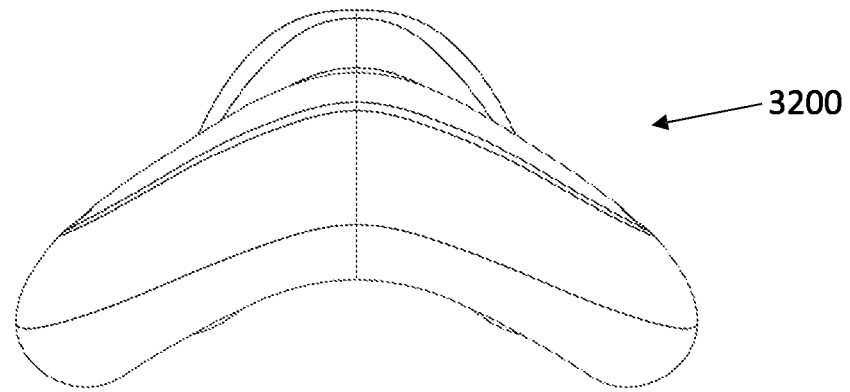

FIG. 13 is a bottom view of the plenum chamber of FIG. 7.

Figure 14:
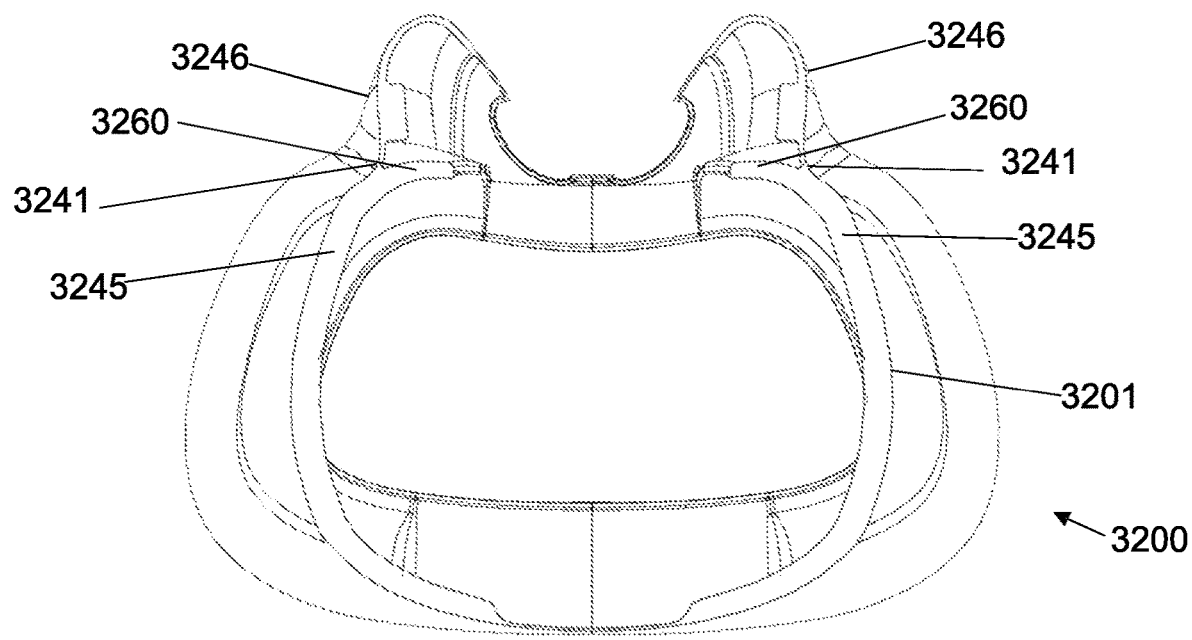

FIG. 14 is a cross-section of the plenum chamber through plane 14-14.

Figure 15:
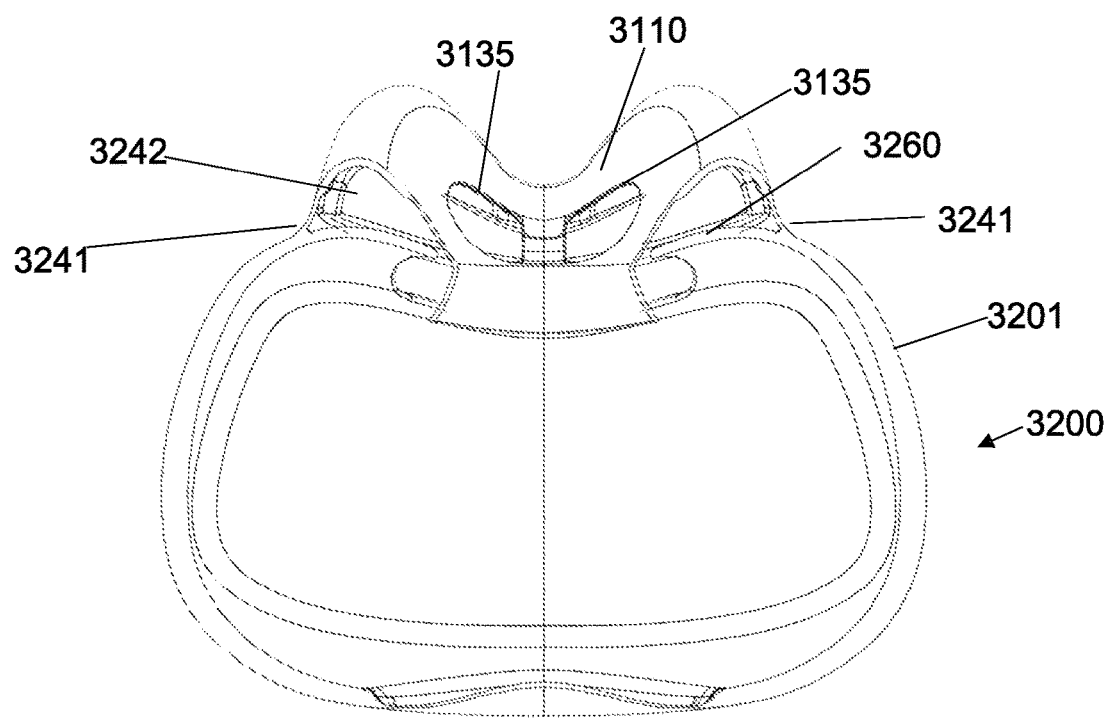

FIG. 15 is a cross-section of the plenum chamber through plane 15-15.

Figure 16:
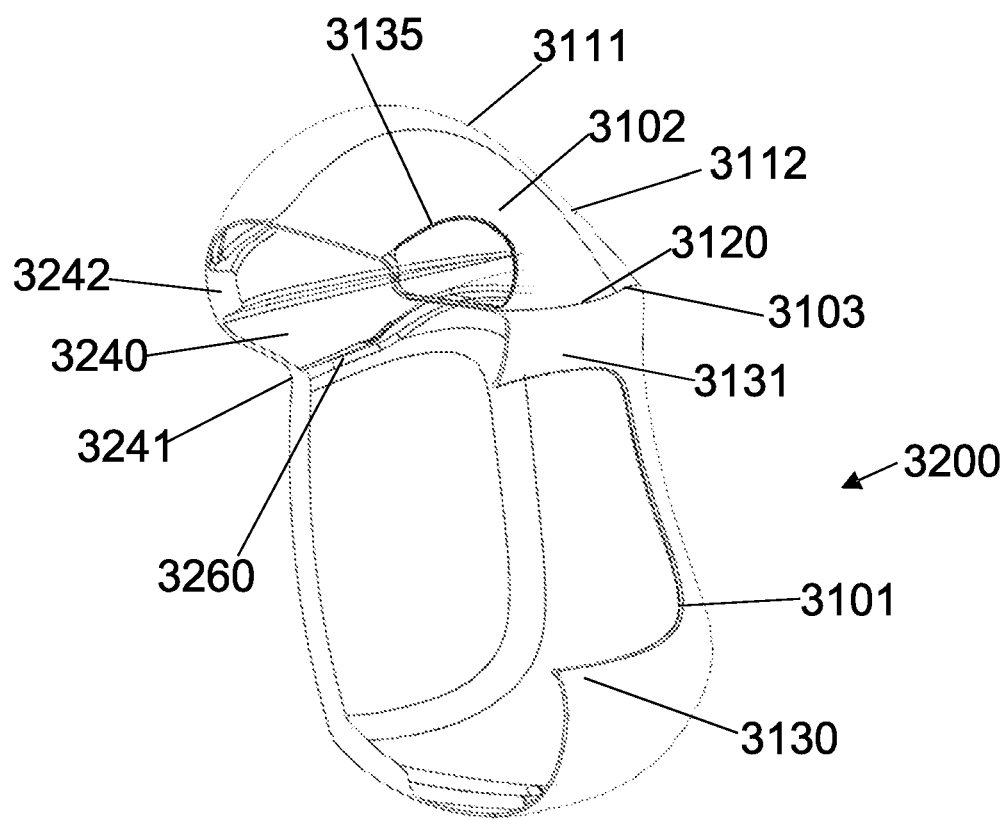

FIG. 16 is a cross-section of the plenum chamber through plane 16-16.

Figures 1, 16:
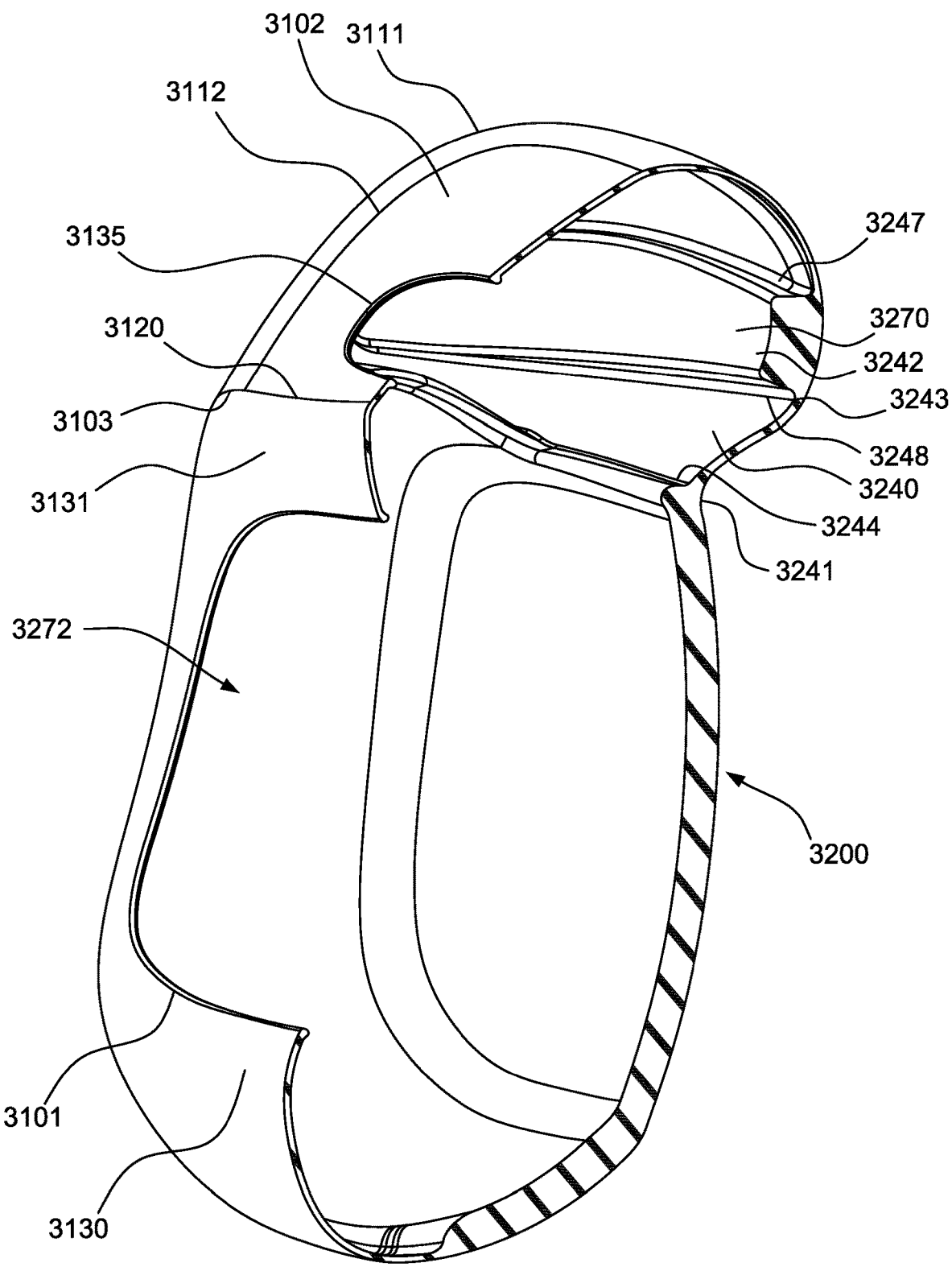

FIG. 16-1 is a cross-section of the plenum chamber through plane 16-1-16-1.

Figures 2, 16:
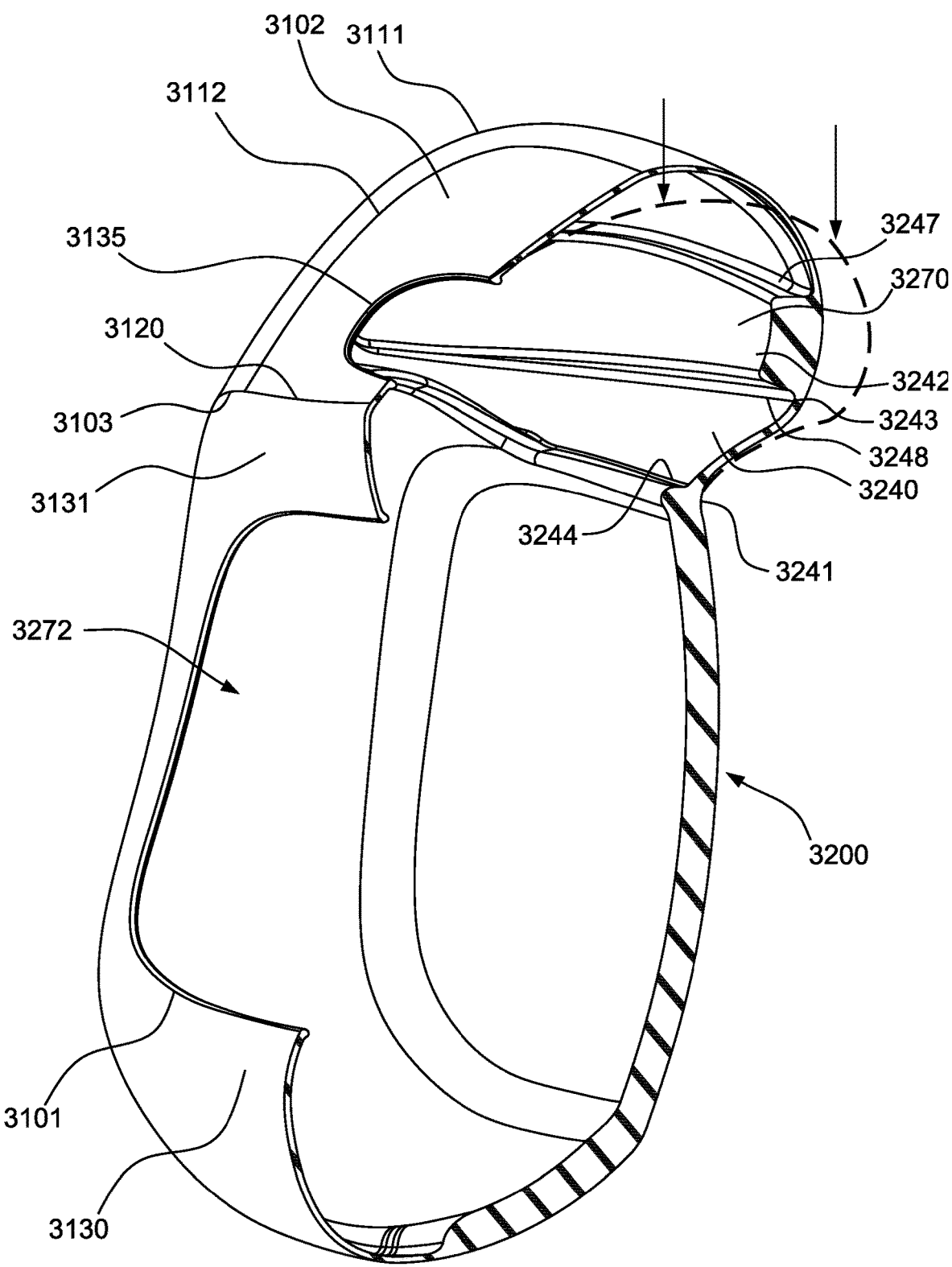

FIG. 16-2 is a cross-section of the plenum chamber of FIG. 16-1, illustrating the plenum chamber in a deformed position.

Figure 17:
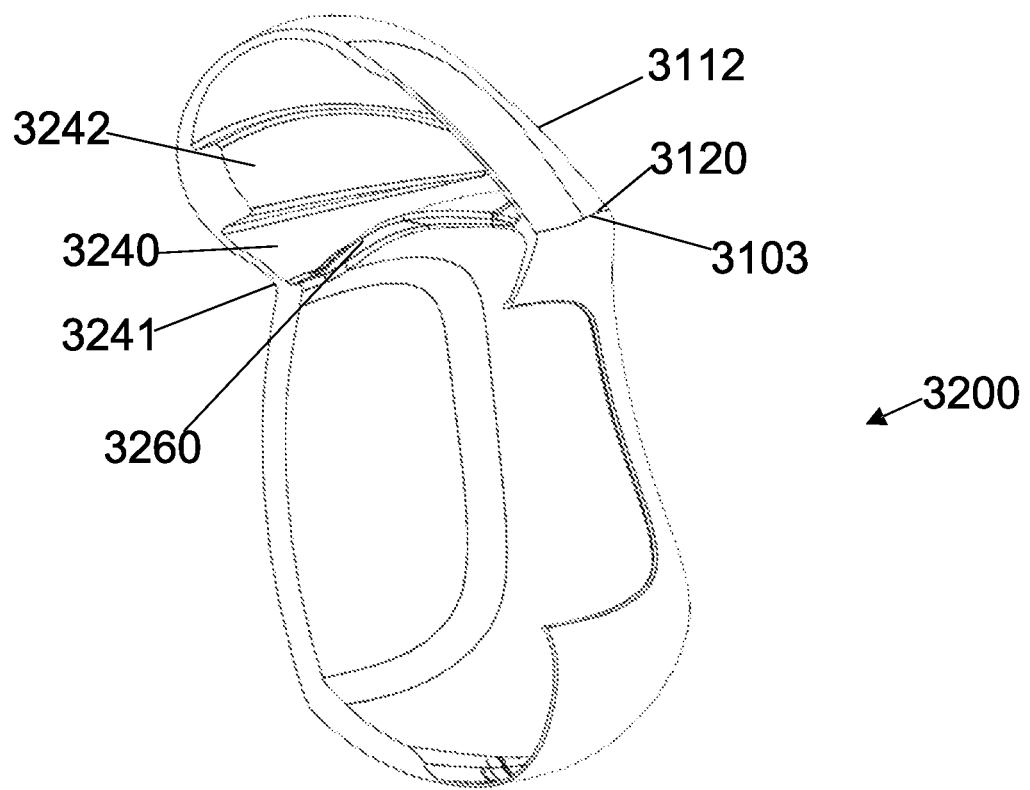

FIG. 17 is a cross-section of the plenum chamber through plane 17-17.

Figure 18:
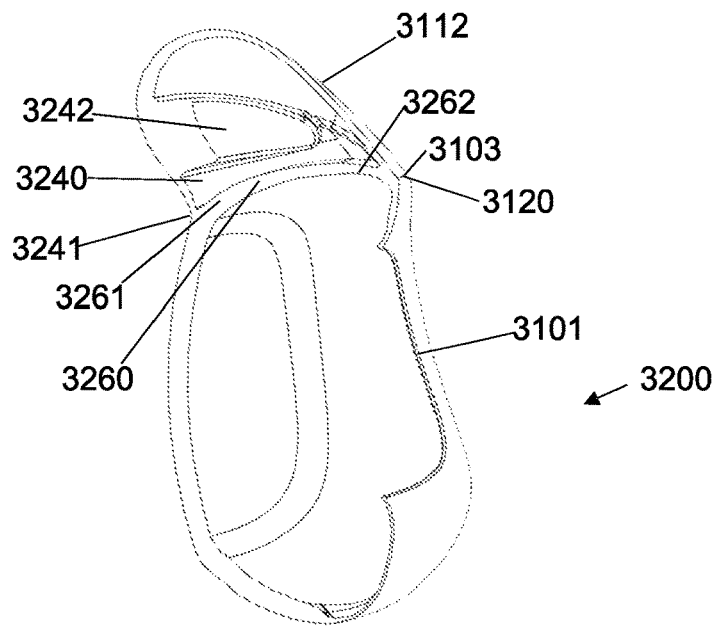
Figures 1, 18:
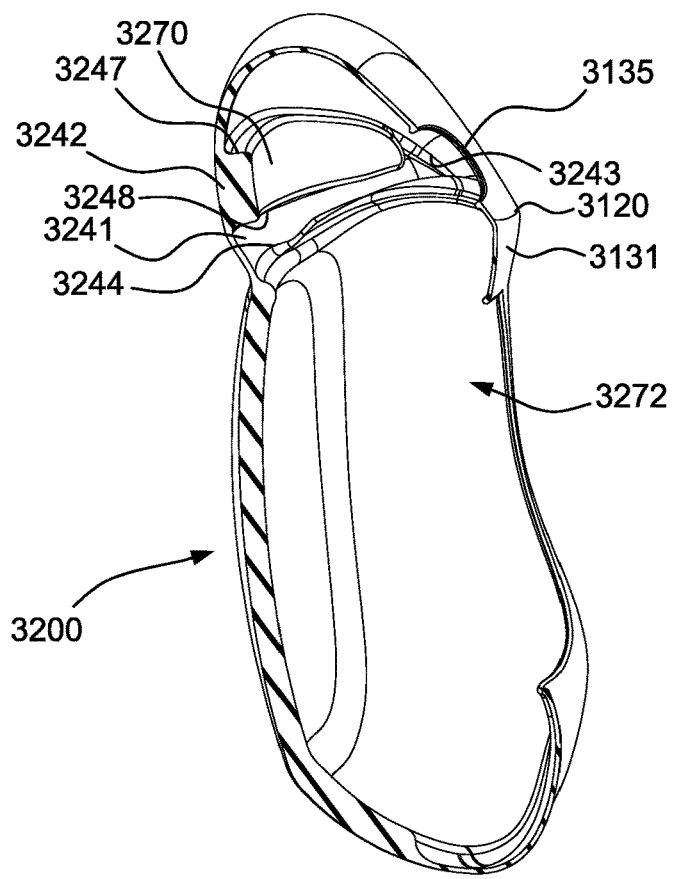
Figures 2, 18:
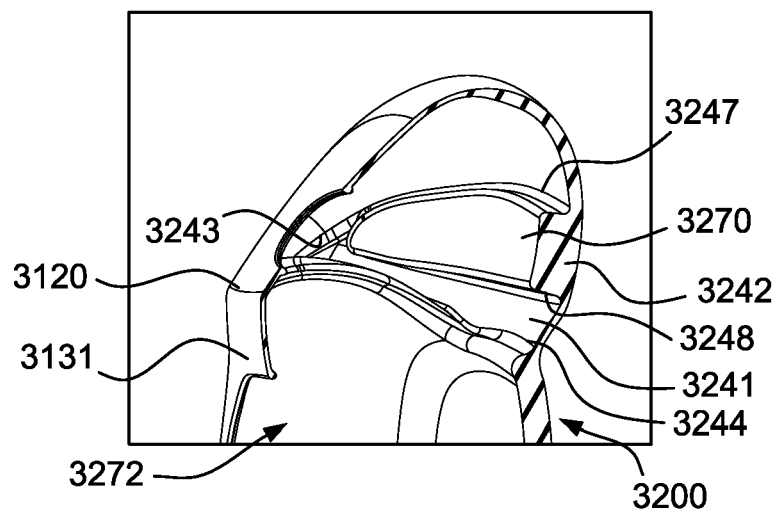

FIG. 18 is a cross-section of the plenum chamber through plane 18-18.

FIG. 18-1 is a cross-section of the plenum chamber through plane 18-1-18-1.

FIG. 18-2 is a cross-section of the plenum chamber through plane 18-2-18-2.

Figure 19:
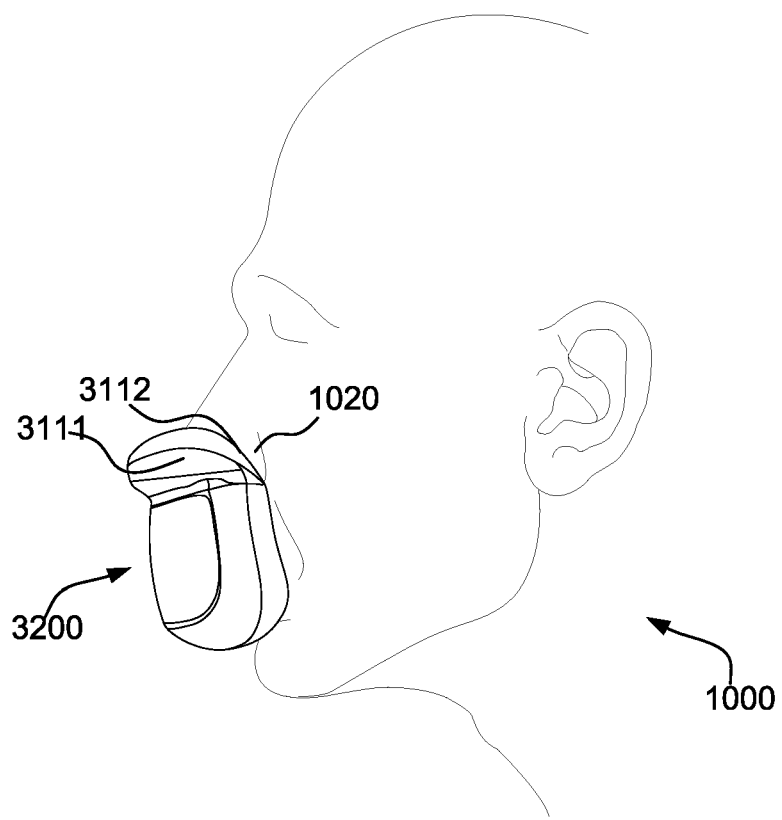

FIG. 19 shows a side view of the plenum chamber in an in-use position on a patient's face, with the plenum chamber shown in outline for clarity.

Figure 20:
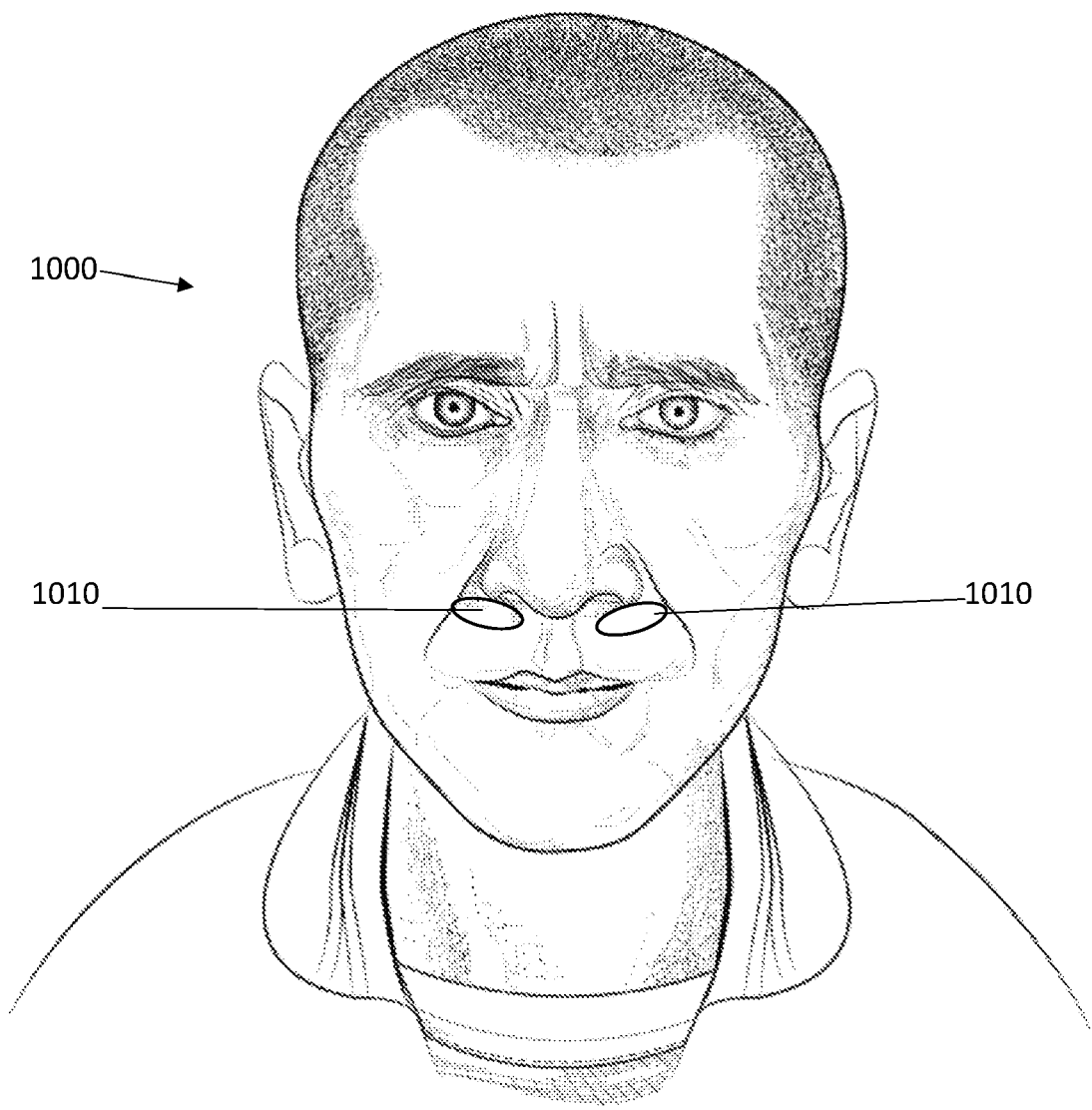

FIG. 20 shows a patient's face with particular areas of engagement by a seal forming structure indicated.

Figure 21:
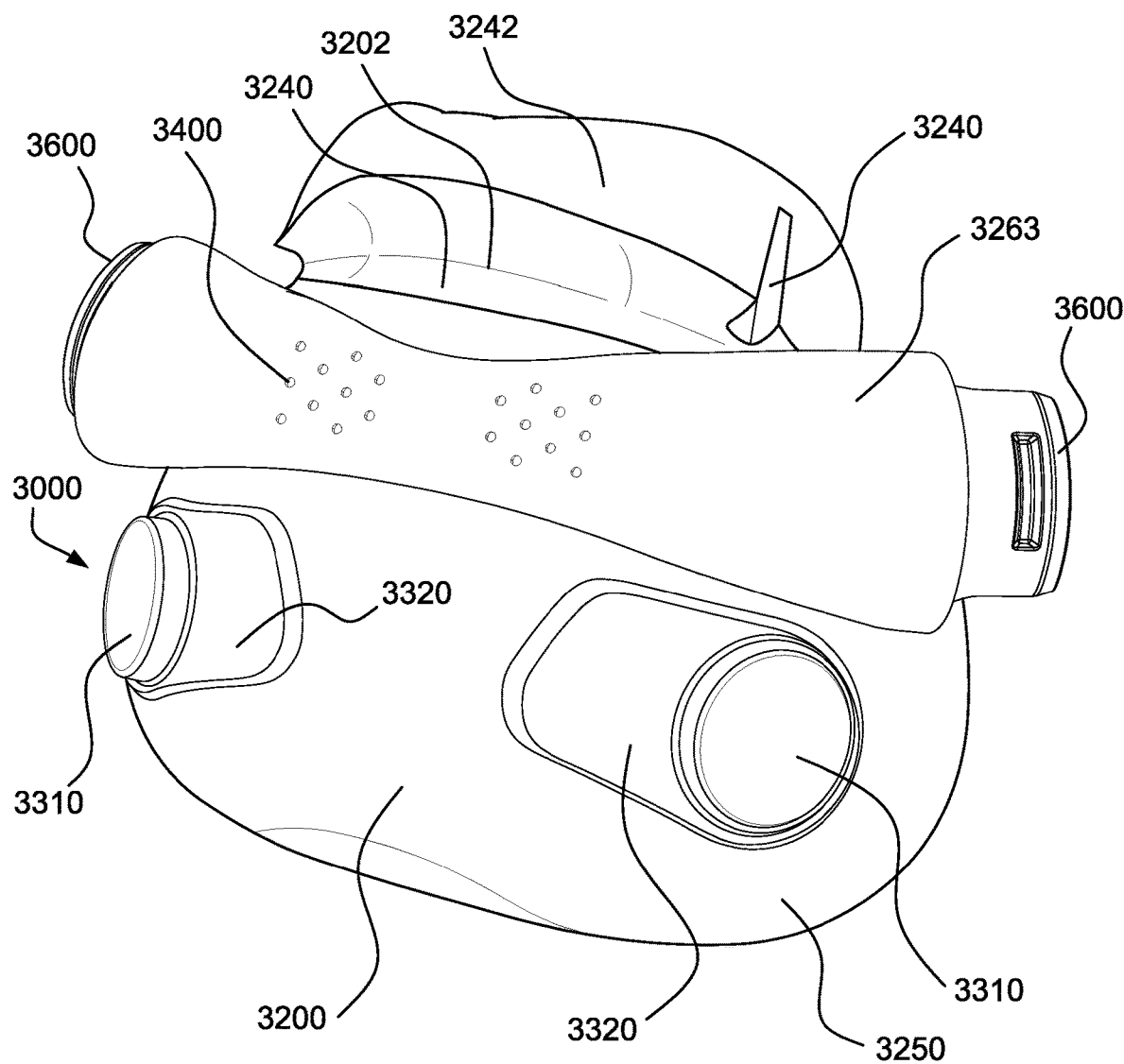
Figures 1, 21:
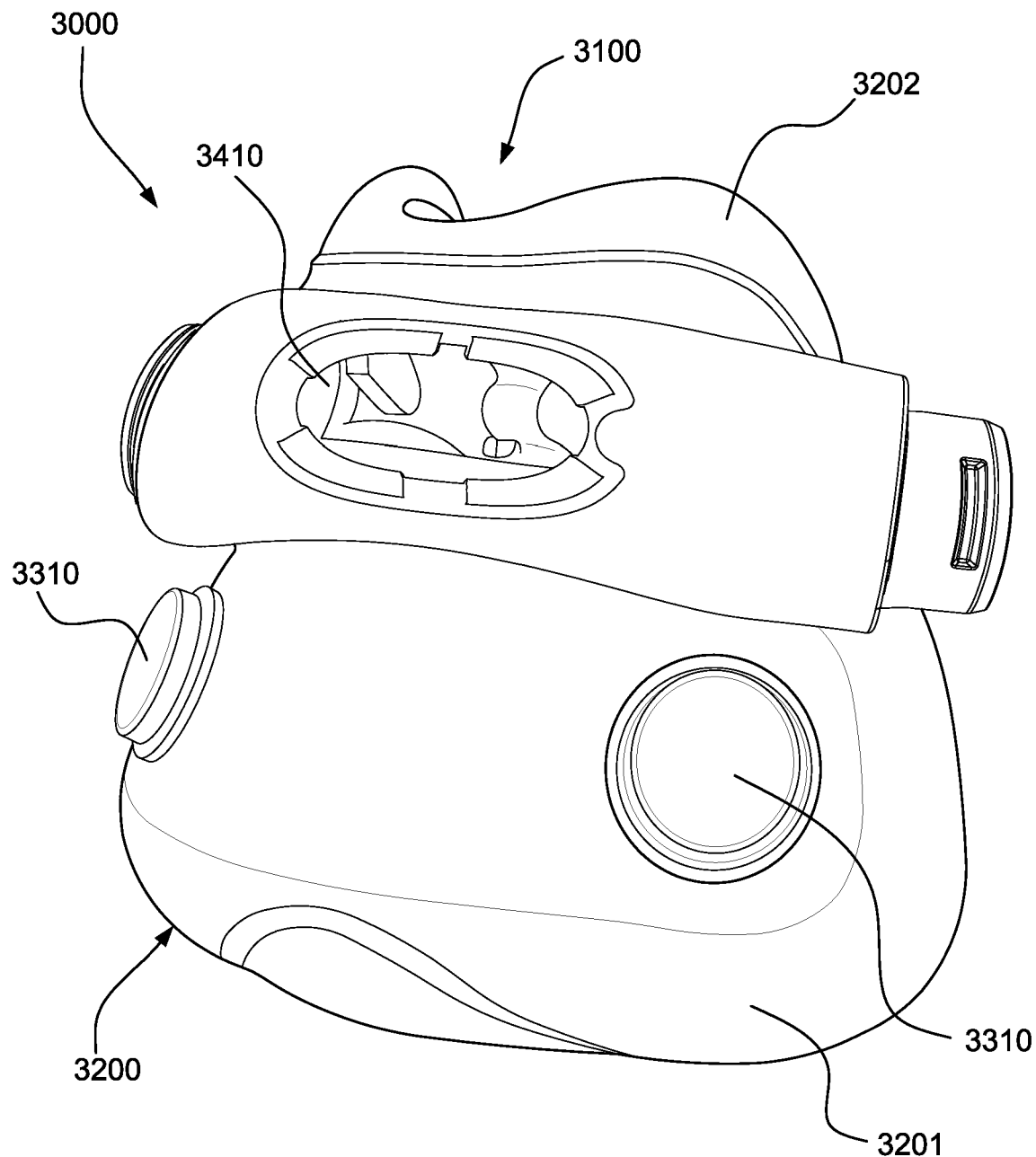

FIG. 21 is a front perspective view of a patient interface in accordance with another form of the technology.

FIG. 21-1 is a front perspective view of a patient interface in accordance with another form of the technology.

Figure 22:
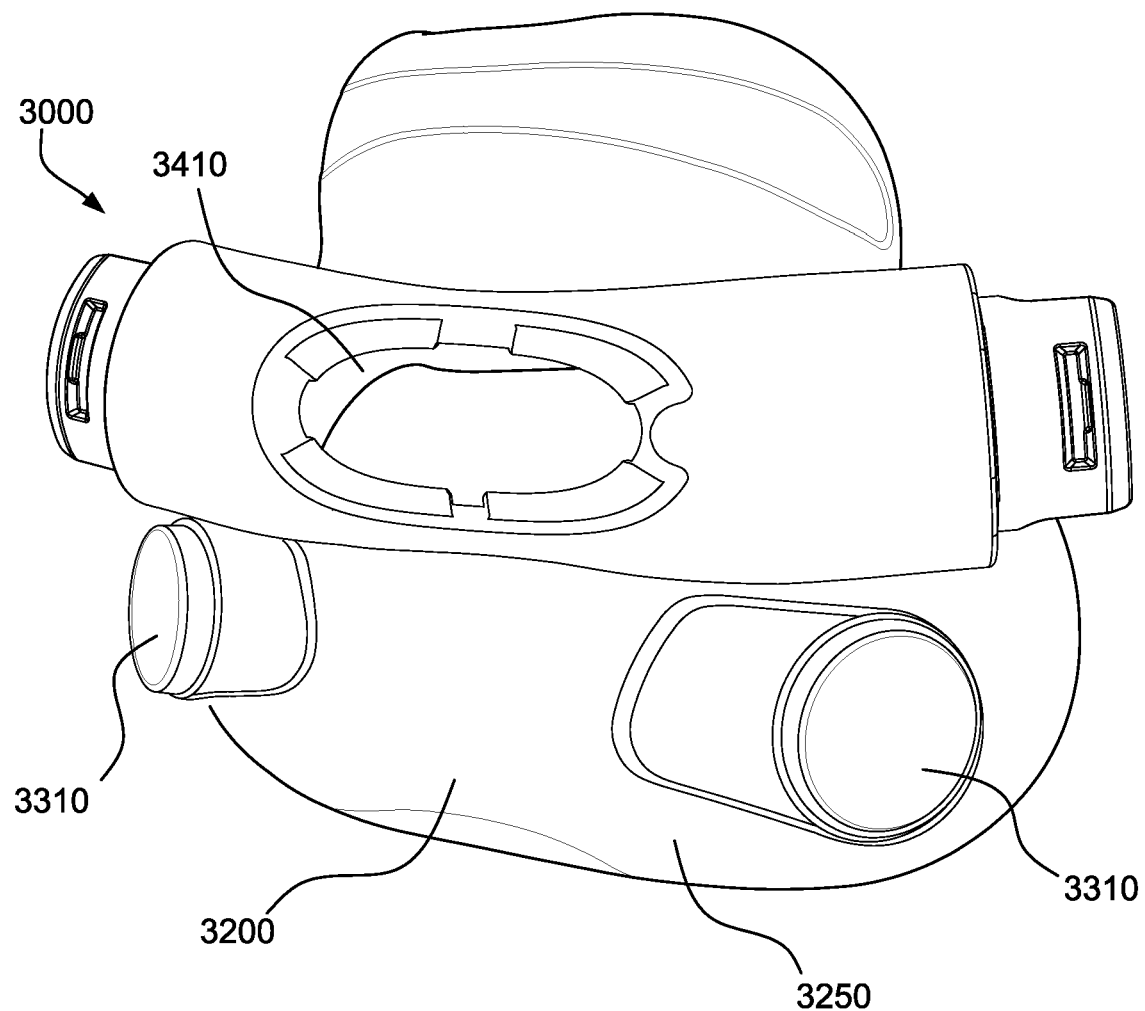

FIG. 22 is a front perspective view of a patient interface in accordance with yet another form of the technology, with a vent removed.

Figure 23:
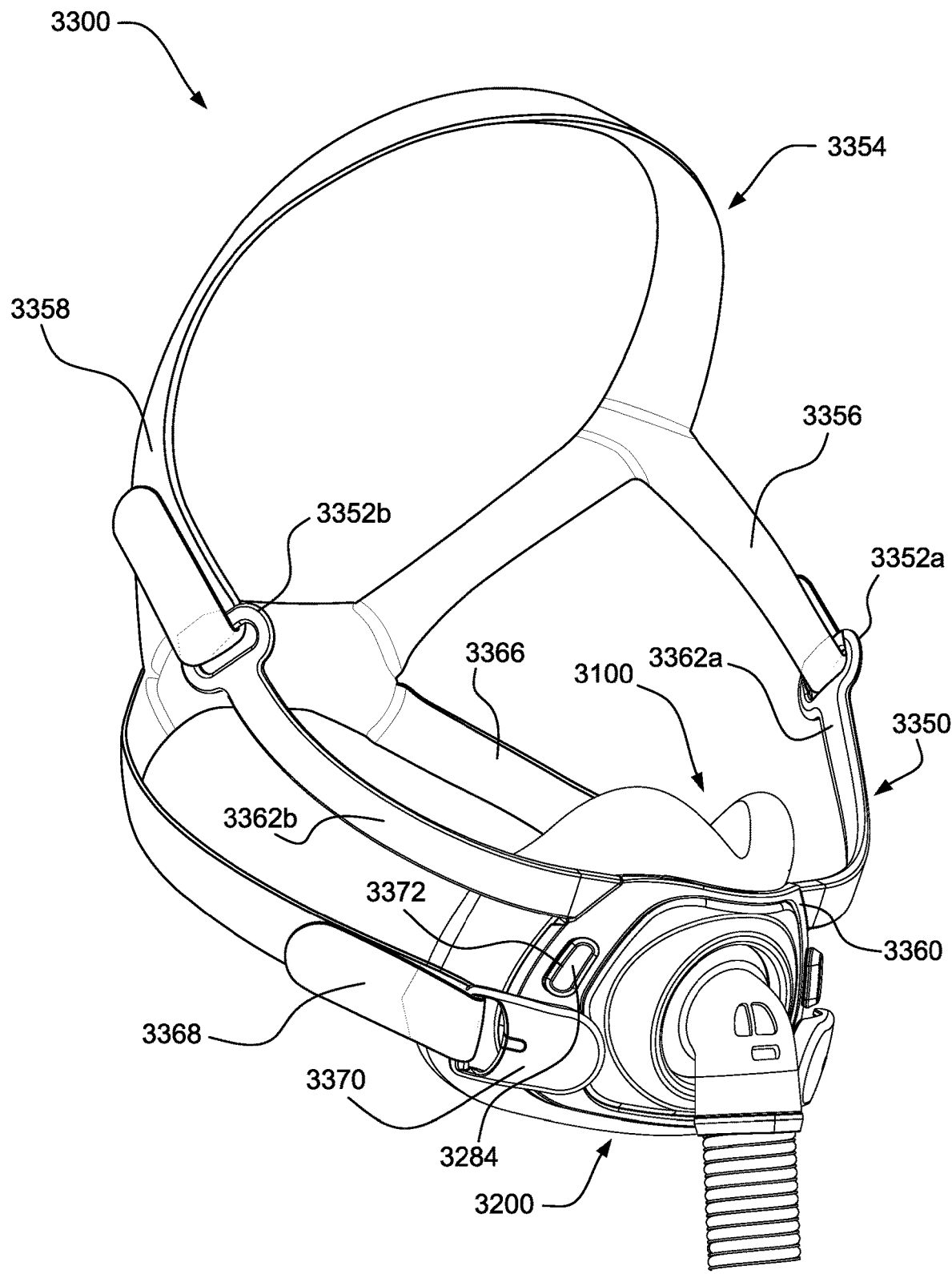

FIG. 23 is a front perspective view of a patient interface having a frame for connecting headgear straps to the plenum chamber.

Figure 24:
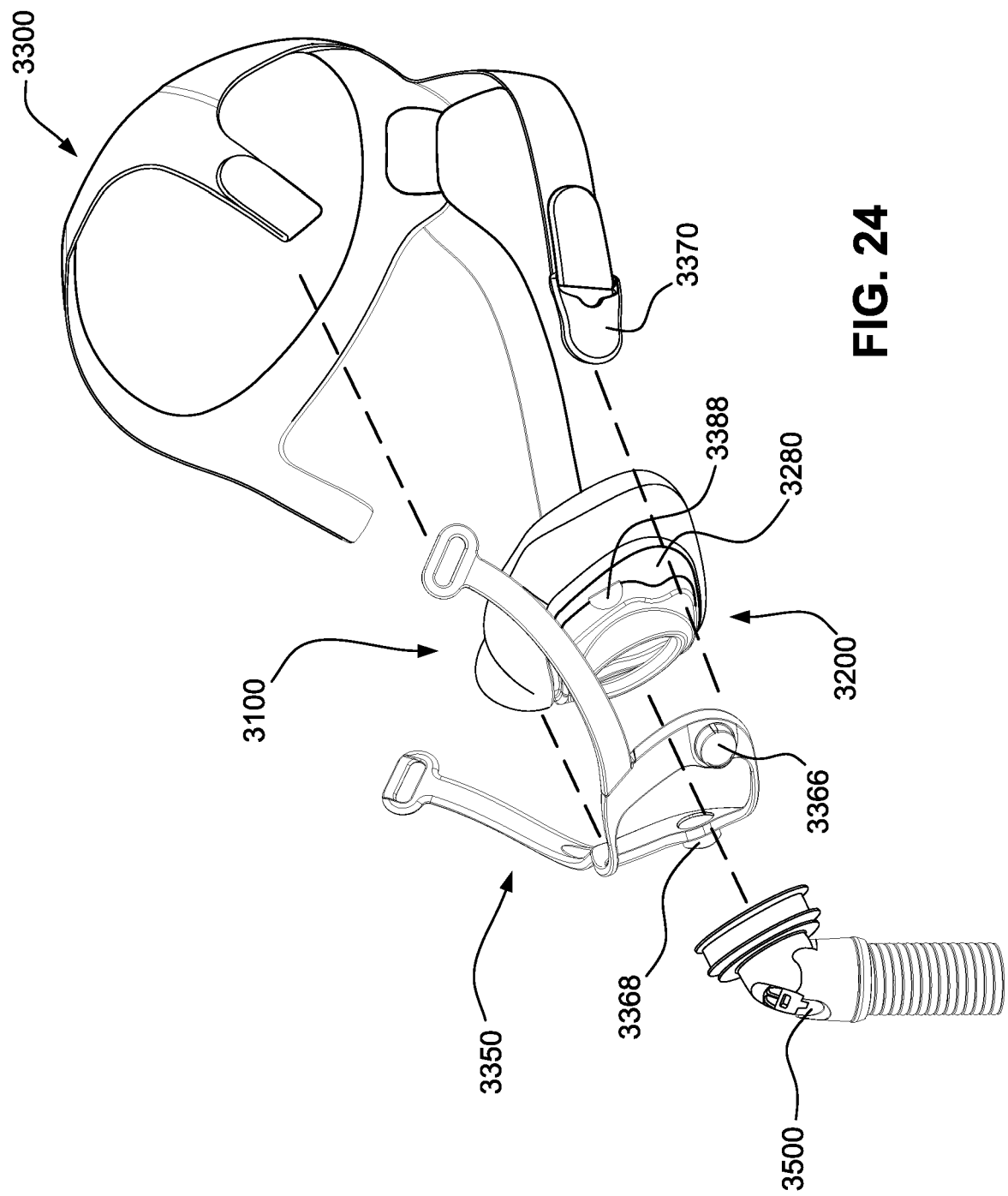

FIG. 24 is an exploded view of the patient interface of FIG. 23.

Figure 25:
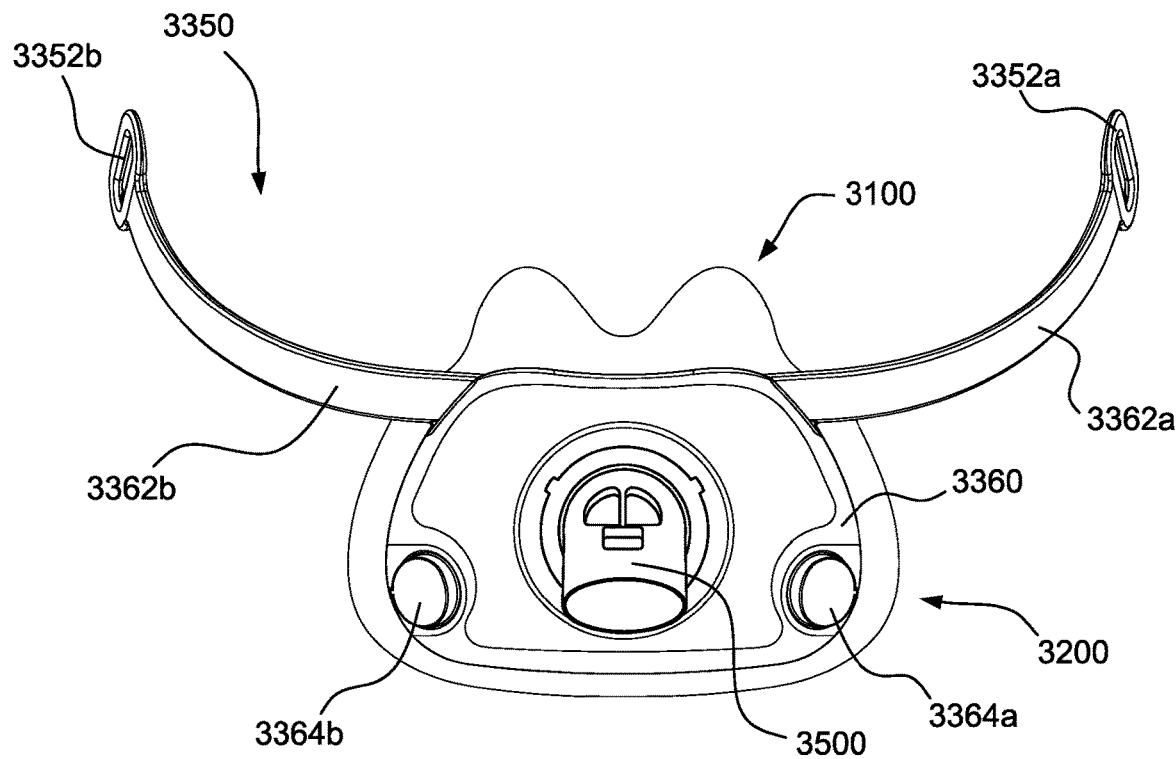

FIG. 25 is a front view of a frame and plenum chamber in accordance with one form of the technology.

Figure 26:
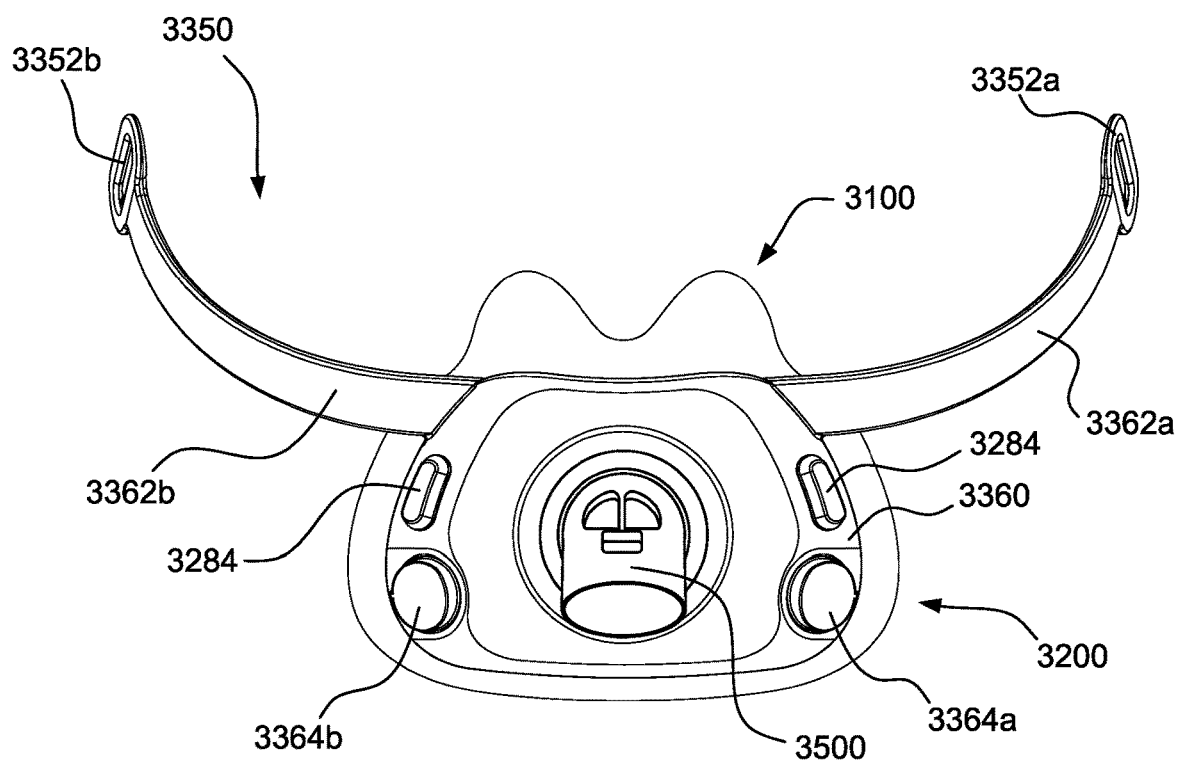
Figures 1, 26:
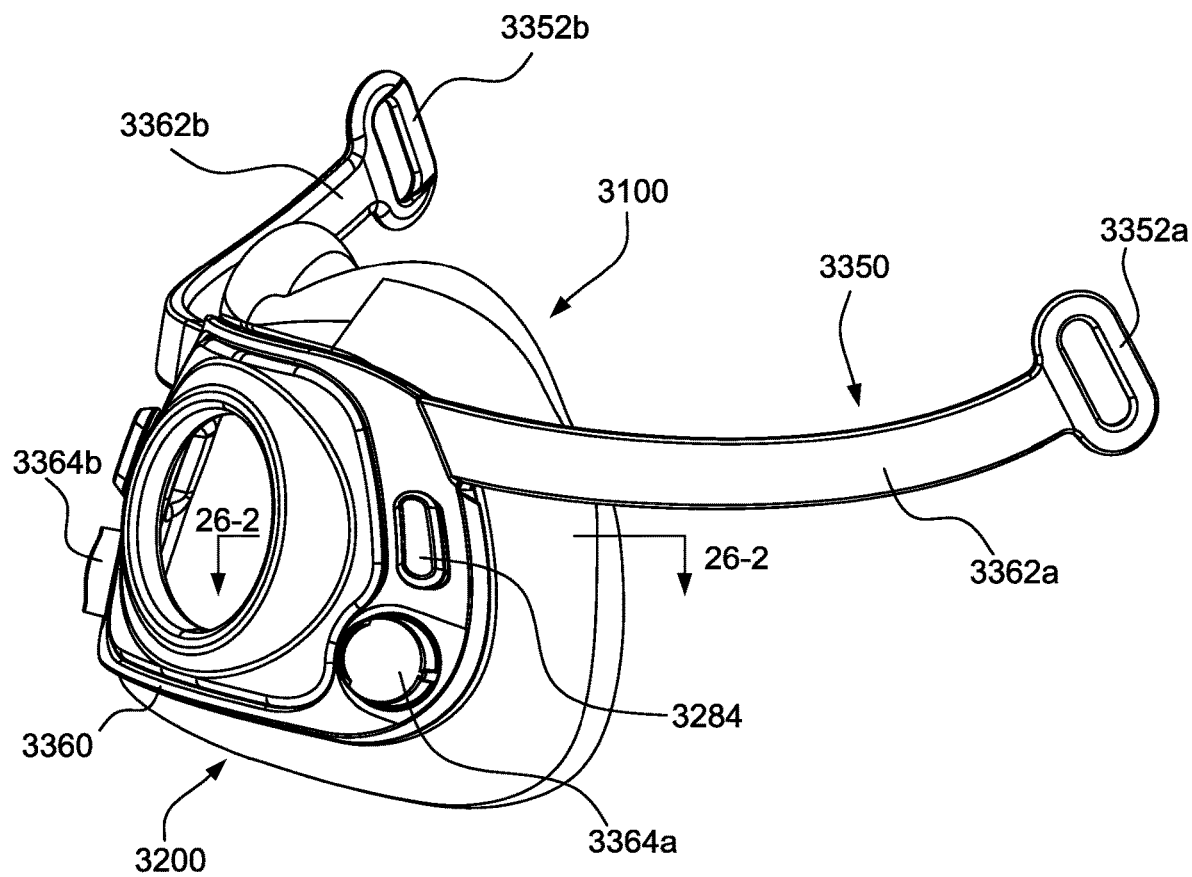
Figures 2, 26:
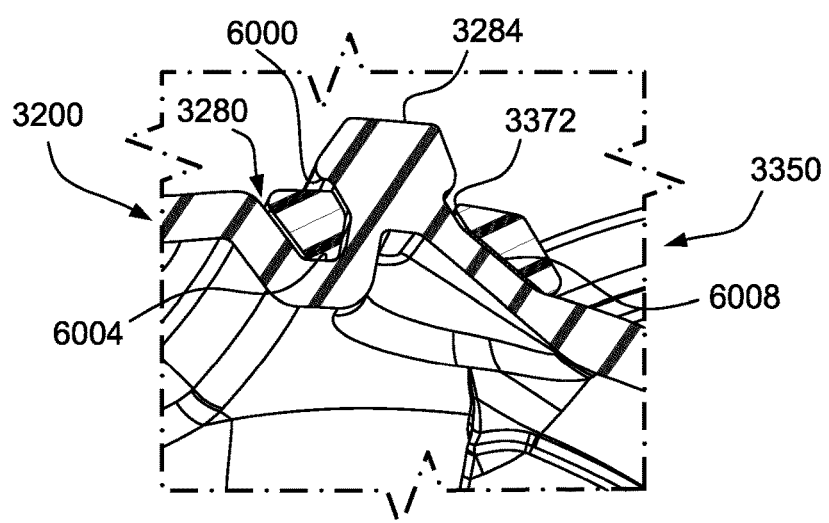

FIG. 26 is a front view of a frame and plenum chamber in accordance with another form of the technology.

FIG. 26-1 is a side perspective view of the frame and plenum chamber of FIG. 26.

FIG. 26-2 is a cross-sectional view of the frame and plenum chamber of FIG. 26-1, viewed along section 26-26.

Figures 3, 26:
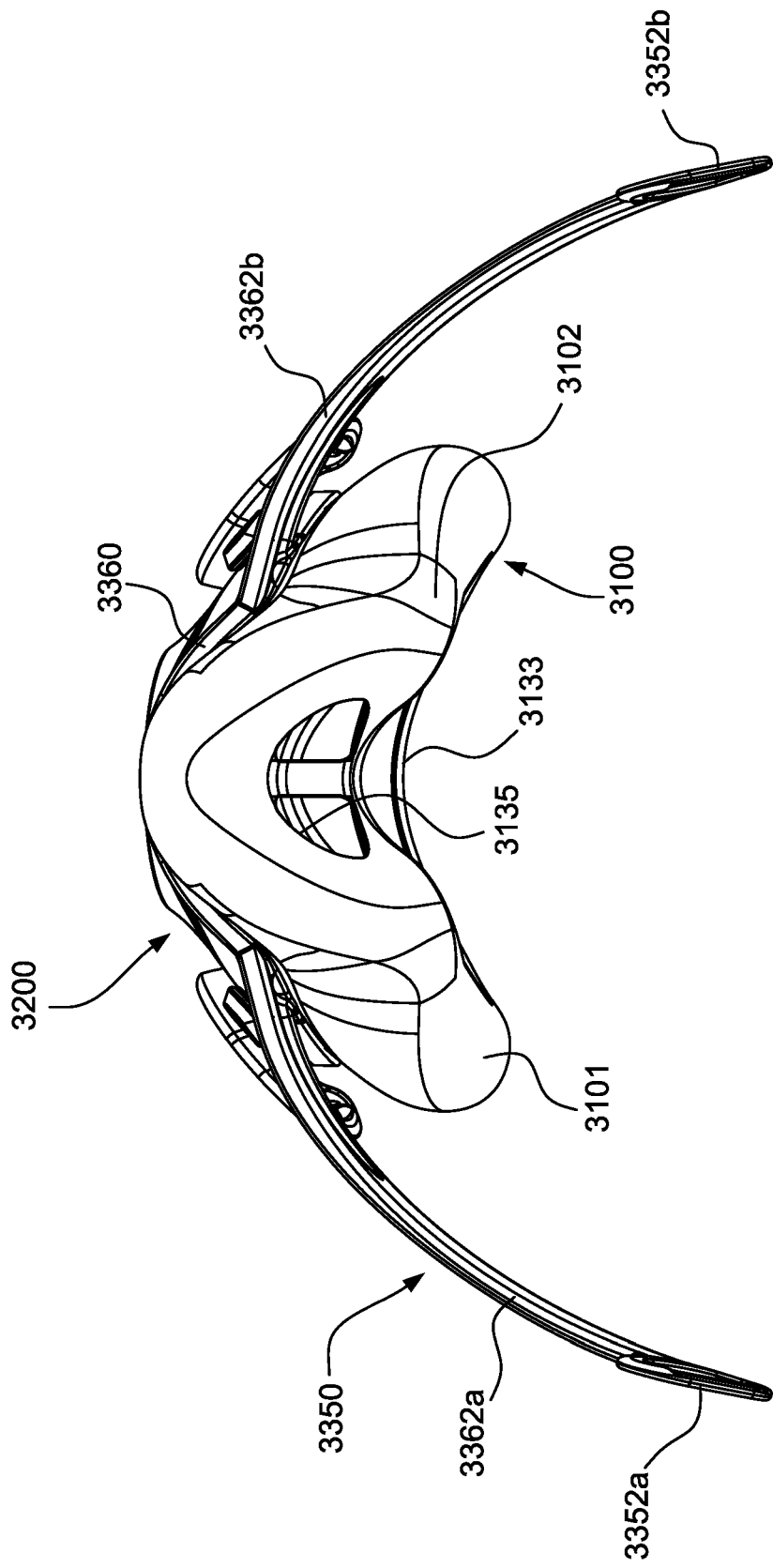

FIG. 26-3 is a top view of the frame and plenum chamber of FIG. 26.

Figures 4, 26:
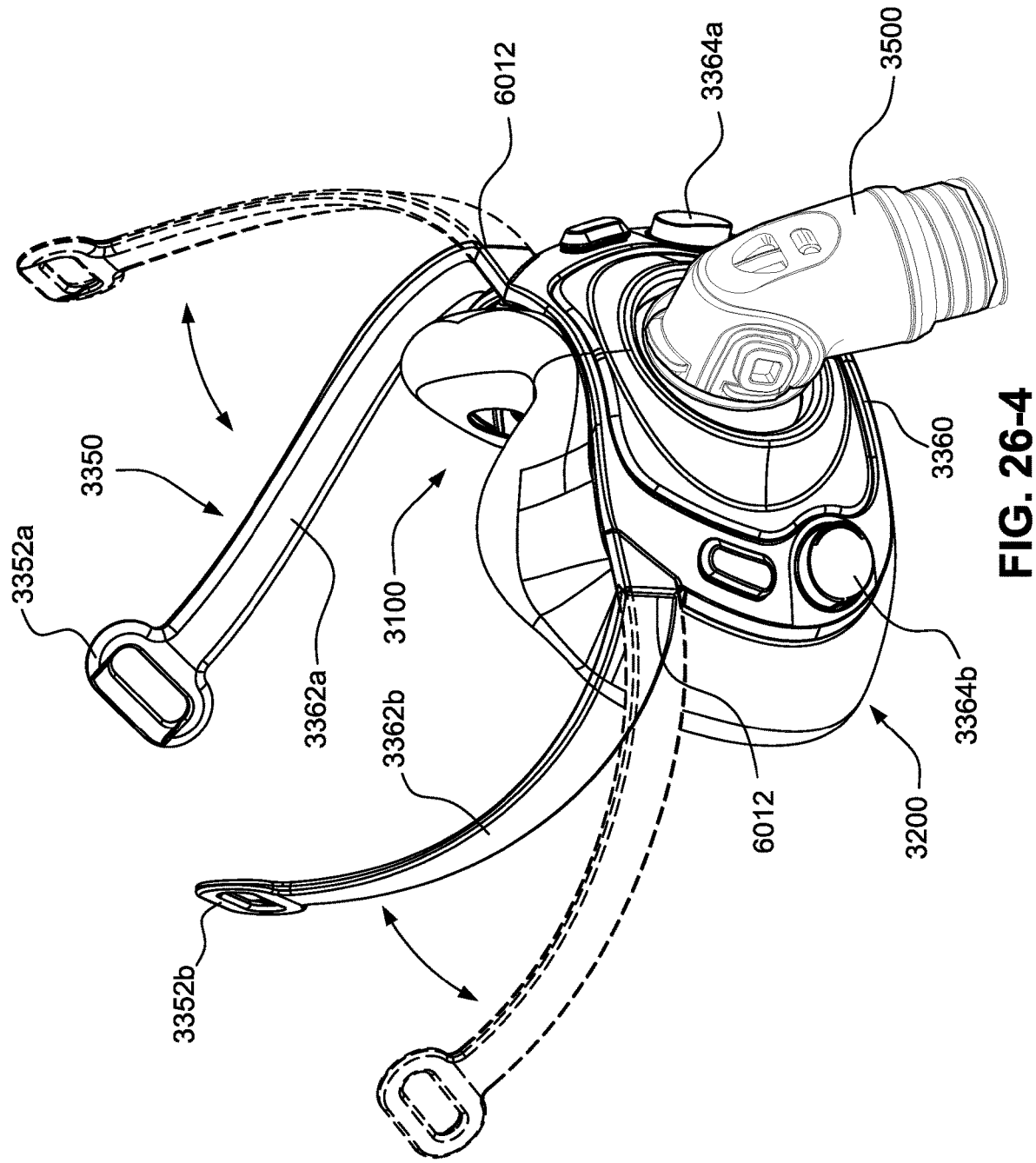

FIG. 26-4 is a perspective view of the frame and plenum chamber of FIG. 26, illustrating arms of the frame moveable between a first position and a second position.

Figures 5, 26:
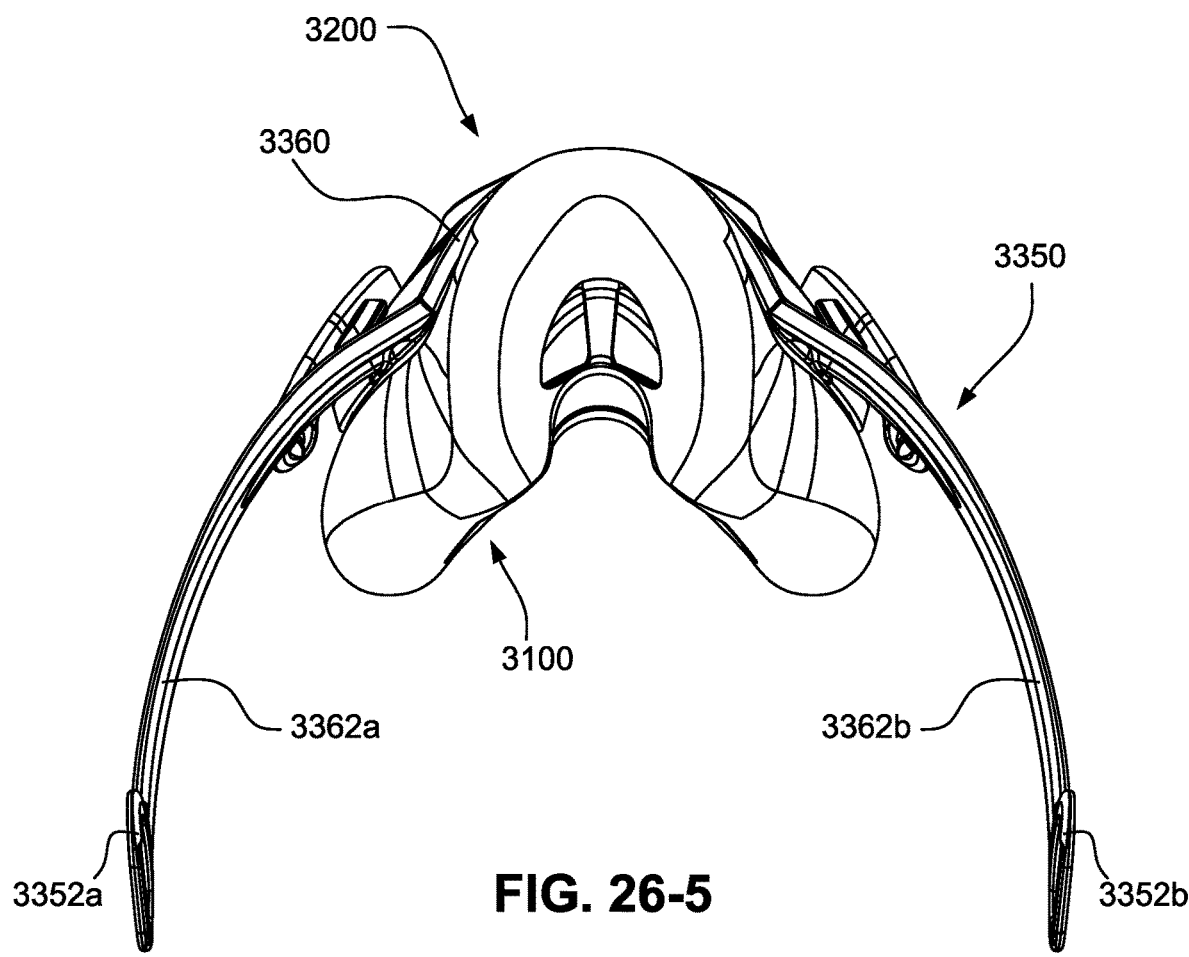

FIG. 26-5 is a rear perspective view of the frame and plenum chamber of FIG. 26-4, illustrating the flexion of the plenum chamber in the second position.

Figure 27:
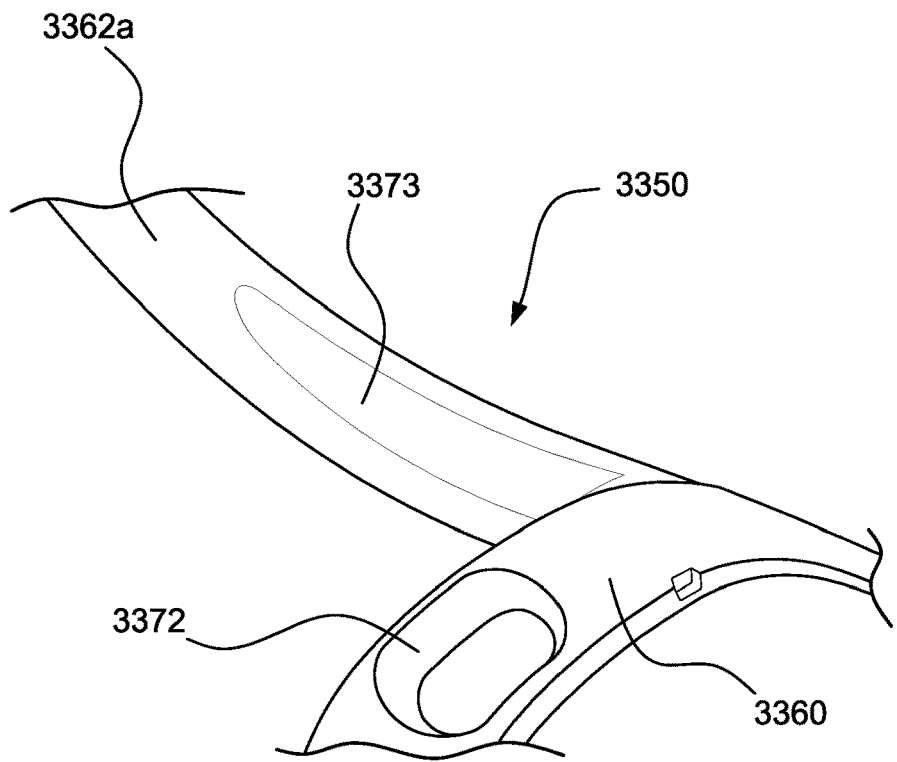
Figures 1, 27:
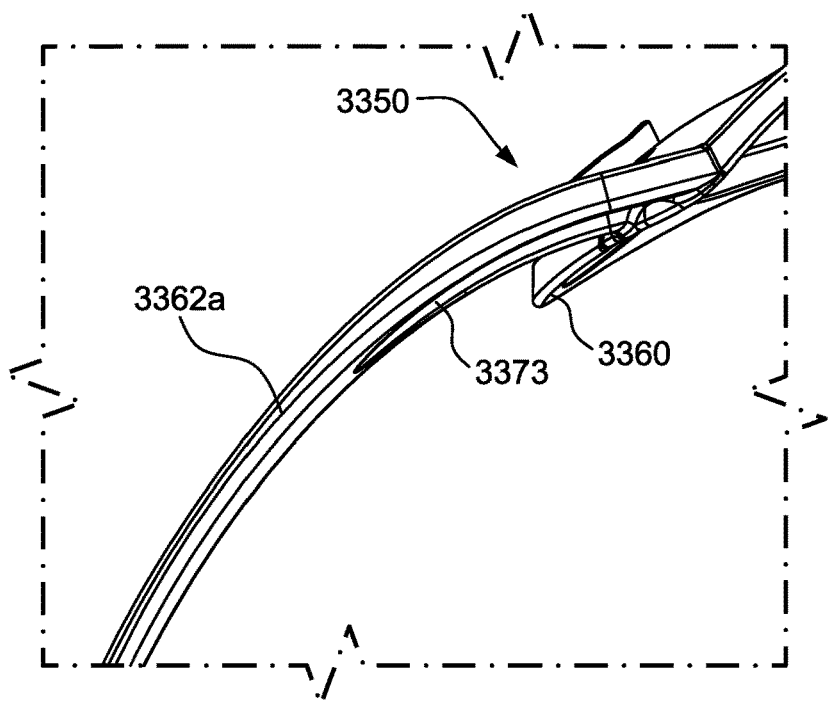
Figures 2, 27:
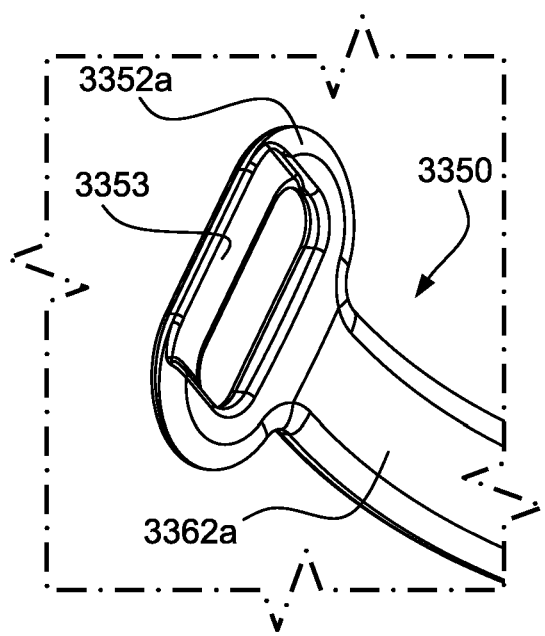
Figures 3, 27:
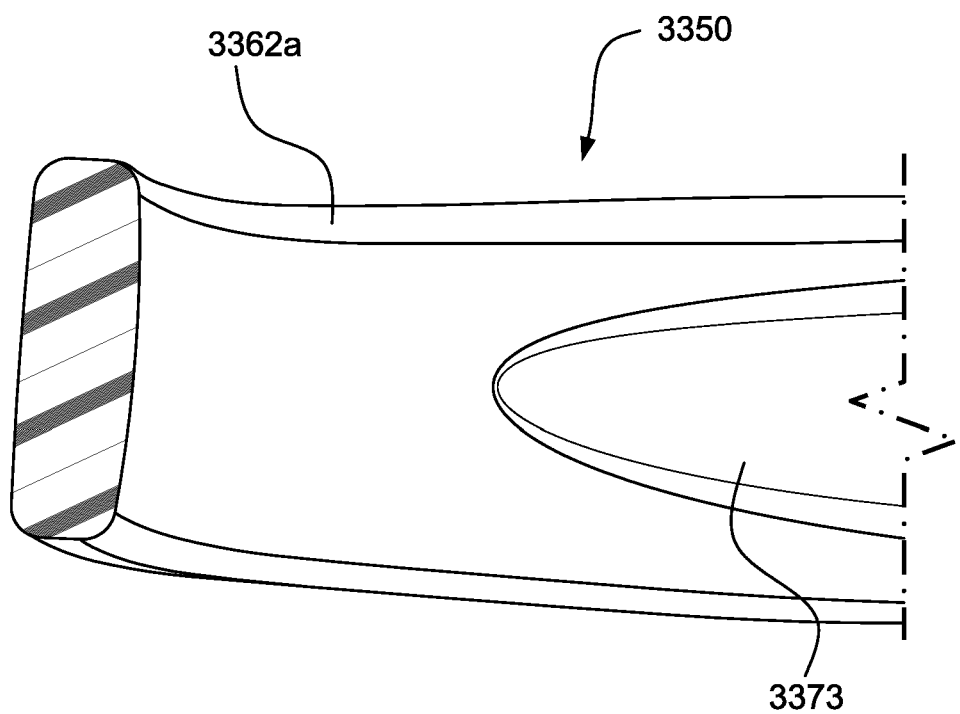

FIG. 27 is a rear view of the frame of FIG. 26, illustrating a tapered opening.

FIG. 27-1 is a top perspective view of the frame of FIG. 26, illustrating a decreasing thickness of an arm of the frame.

FIG. 27-2 is a perspective view of the frame of FIG. 26, illustrating a loop on a free end of the frame.

FIG. 27-3 is a partial perspective view showing a cross-sectional shape of an arm of the frame in FIG. 26.

Figure 28:
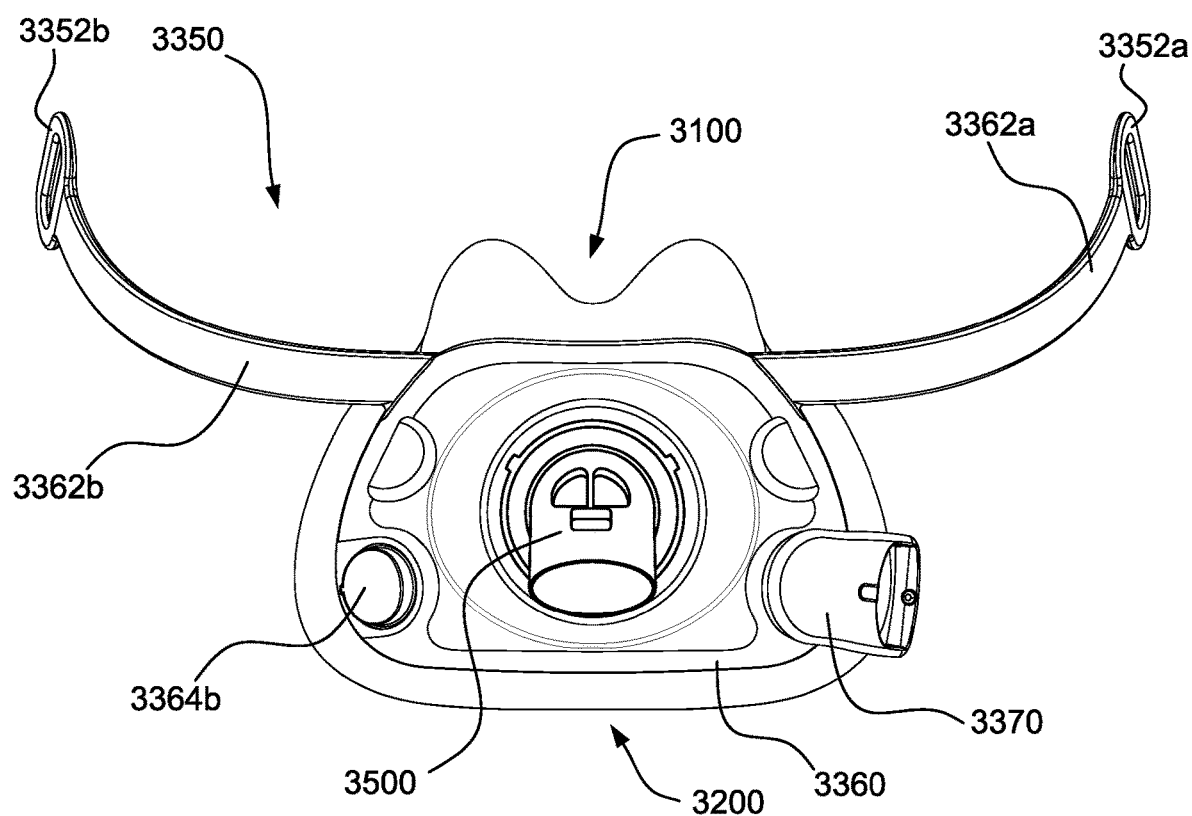
Figures 1, 28:
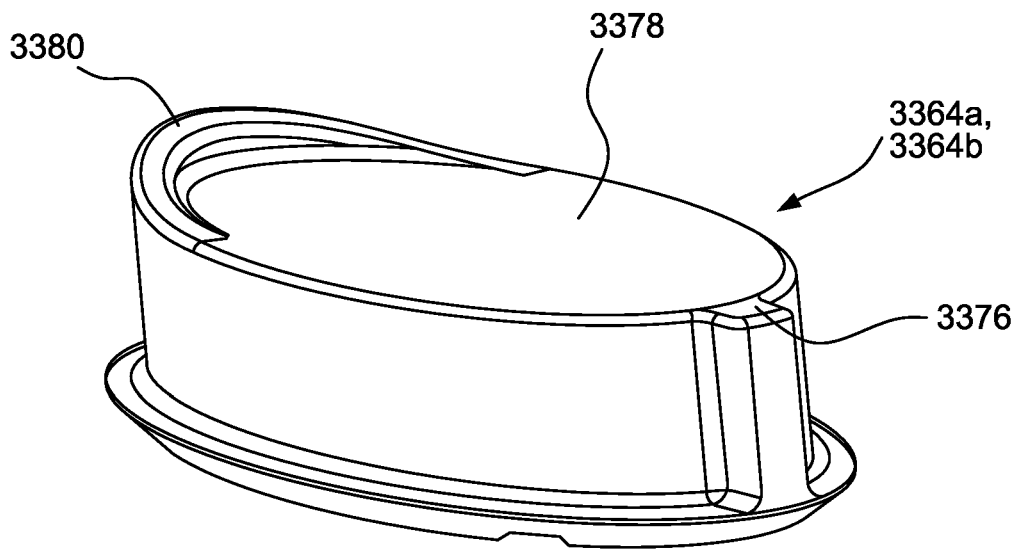
Figures 2, 28:
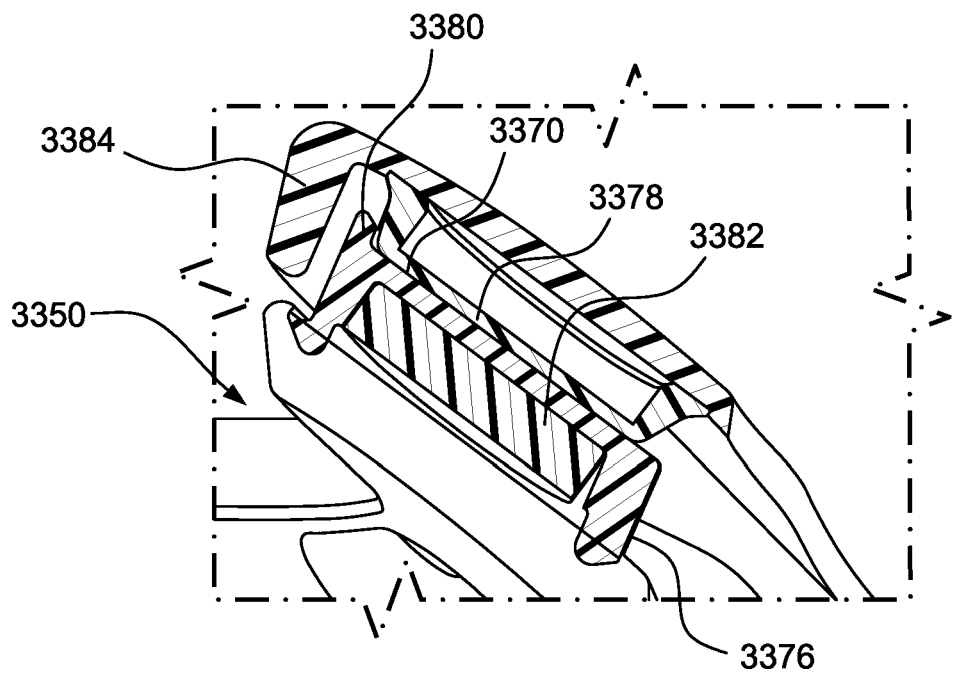

FIG. 28 is a front view of a frame and plenum chamber in accordance with yet another form of the technology.

FIG. 28-1 is a perspective view of a secondary connection point usable with the frame in one form of the technology.

FIG. 28-2 is a cross-sectional view of the frame and plenum chamber of FIG. 28, illustrating the connection between a magnet and a secondary connection point of FIG. 28-1.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

Where anatomical directional terms are used in describing aspects and examples of the present technology, such as "anterior", "posterior", "superior" and the like, the directions are to be read in the context of the present technology during use by the patient. For example, an anterior side of a patient interface refers to the side of the patient interface which is anterior with respect to the patient when the patient has donned the interface in the intended manner.

Where surfaces or portions are described as facing a direction, e.g. "superior facing", "anterior facing" and the like, unless the context clearly requires otherwise, the surfaces or portions are to be understood as at least partially facing in the particular direction. A portion may be "superior facing" if the portion generally faces a superior direction, even if it also partially faces another direction.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

In some examples of the present technology, the plenum chamber is at least partially formed by a shell 3250. In examples the shell 3250 or a portion of the shell 3250 may be somewhat flexible, as is discussed further below.

The patient interface in some examples of the technology is an oro-nasal patient interface, that is, the patient interface is configured to seal around both the patient's nasal airways and oral airway. In some examples the patient interface comprises separate seals around the each of the nasal airways and the oral airway.

In the examples shown in FIGS. 7-22 the seal forming structure at the nasal portion does not lie over a nose bridge region or nose ridge region of the patient's face and instead seals against inferior surfaces of the patient's nose.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

As is described in greater detail below, in certain forms of the invention the seal forming structure 3100 comprises a first seal forming structure 3101 connected to an oral portion 3201 of the plenum chamber and constructed and arranged to form seal with a region of the patient's face surrounding an entrance to the patient's mouth, and a second seal-forming structure 3102 connected to a nasal portion 3202 of the plenum chamber 3200 constructed and arranged to form a seal with a region of the patient's face surrounding an entrance to the patient's nose. The phrase "connected to" is used herein to refer to portions or components which are formed as a single piece as well as to portions or components which are formed separately and subsequently joined together. In some cases components may be connected by an intermediate component.

In certain forms, the first seal forming structure 3101 seals independently against the patient's face than the second seal forming structure 3102.

In certain forms, the first seal forming structure 3101 and the second seal forming structure 3102 cooperate to form a single common seal against the patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure 3100 includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use. Limiting the occurrences of buckling may limit creases from forming in the seal-forming structure 3100, which may lead to leaks and loss of the therapeutic pressure.

In one form, the seal-forming structure 3100 may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure 3100 comprises a tension portion. In use, the tension portion is held in tension, e.g. by adjacent regions of the sealing flange.

In one form, the seal-forming structure 3100 comprises a region having a tacky or adhesive surface.

In certain forms of the present technology, a seal-forming structure 3100 may comprise one or more of a pressure-assisted sealing flange, a compression sealing portion, a gasket sealing portion, a tension portion, and a portion having a tacky or adhesive surface.

5.3.1.2 Nasal Region

Referring next to FIGS. 7 to 18, in certain forms of the present technology, the second seal forming structure 3102 comprises a central portion 3110 configured to seal to surfaces of the patient's nose in use. The central portion may seal to an inferior periphery of the patient's nose (e.g. surrounding the patient's nares) and to the patient's lip superior. In examples a portion of the seal forming structure may engage the patient's septum. The second seal forming structure 3102 may further comprise lateral portions 3111 on lateral sides of the central portion 3110. In examples, the seal forming structure 3102 may be configured to contact the patient's face below the bridge of the nose or below the pronasale.

As best seen in FIGS. 10 and 16-19, posterior surfaces 3112 of the lateral portions 3111 slope forward in a superior/anterior direction from the boundary 3103 of the first and second seal forming structures 3101, 3102 such that in profile the posterior side of the nasal part of the mask slopes forward.

In embodiments provided with a ridge 3120 (as described further below), the posterior surfaces 3112 of the lateral portions 3111 may slope forward from the ridge 3120.

In some forms of the technology the posterior surfaces 3112 of the lateral portions 3111 form an angle with a mid-contact plane of the mask of between 20° and 90°. The mid-contact plane may be perpendicular to the sagittal plane, and may extend substantially along a length of the ridge 3120 and the chord 3210.

As shown in FIG. 19, in some embodiments the lateral portions 3111 are configured such that no part of the patient interface 3000 contacts the patient's alar crest point 1020 when in use.

Configuring the lateral portions 3111 to slope in this way results in a smaller portion of the nasal part of the interface 3000 extending over the sides of the ala than some similar interfaces of the prior art. In some forms of the technology this results in the portion of the ala which is in contact with the seal-forming structure 3100 being reduced relative to interfaces with lateral portions which slope backward, toward the patient's face, thereby reducing the proportion of the ala which can be deformed and occluded by the seal-forming structure 3100, for example when the patient sleeps on their side with the interface in contact with a pillow.

5.3.1.3 Boundary of Oral and Nasal Regions

With particular reference to FIGS. 7, 8 and 16-18, in one form of the technology the boundary between the first sealing forming structure 3101 and the second seal forming structure 3102 forms or comprises a corner or ridge 3120. In use, the corner or ridge 3120 may engage the patient's face above the lip superior and immediately below the nose.

In embodiments the corner or ridge 3120 forms a sharper angle than the equivalent portion or area of some oro-nasal masks of the prior art, for example those described in PCT application No. PCT/AU2019/050278.

The sharper angle reduces the likelihood of creases forming in the first and/or second seal forming structures 3101, 3102 on or adjacent the corner or ridge 3120 when the mask is donned and therapy is applied. Some oro-nasal patient interfaces which do not use such a structure may require a very thin, rounded formation in this area which may be less resistant to creasing. By contrast, the corner or ridge 3120 may be stiffer, and may hold its shape better, than such interfaces and may therefore seal better against the concavities and creases present around the patient's nose. This effect may be enhanced in embodiments which are provided with support portions, for example support portions 3260 as described herein, which resist or oppose compression of this region.

In some forms of the technology the radius of the corner or ridge 3120 may be less than 2 mm, for example around 1.75 mm. In one form of the technology the radius may vary from approximately 1.75 mm in the centre of the ridge to approximately 0.75 mm at the lateral portions.

The angle formed by the first and second sealing structures may be between 20 degrees and 90 degrees, for example 36 degrees.

In some forms of the technology, the corner or ridge 3120 may extend across substantially an entire boundary 3103 between the first seal forming structure 3101 and the second seal forming structure 3102. In embodiments the corner or ridge 3120 may engage the patient's face at least approximate the entrances to the nares, for example where the ala meets the face above the lip superior, as indicated by areas 1010 in FIG. 20.

5.3.1.4 Oral Region

As is described above, in one form the non-invasive patient interface 3000 comprises a first seal-forming structure 3101 that forms a seal in use around the patient's mouth. The first seal forming structure 3101 may form a seal on a chin-region of the patient's face.

In one form, the seal-forming structure includes a saddle-shaped region constructed to form a seal in use on a chin-region of the patient's face.

The seal forming structure 3100 comprises a lip inferior portion 3130 which forms a seal against the chin region of the patient and/or the lip inferior and/or supramenton of the patient. The lip inferior portion 3130 may be connected to (e.g. contiguous with) a lip superior portion 3131 via an oral hole peripheral portion 3132, as shown in FIG. 16.

The seal forming structure 3100 comprises a relatively low wall thickness (compared to other portions of the interface), for example less than 0.7 mm, at the oral hole peripheral portion 3132, the lip inferior portion 3130 of the seal forming structure which lies against the chin region, and at least the centre of the lip inferior portion 3130. The low wall thickness in these locations assists in achieving an effective, comfortable seal. The seal forming structure in these regions is able to readily conform to any complex geometry.

In some forms of the technology the oral hole 3133 is substantially trapezoidal rather than oval or elliptical, in order to more accurately correspond to a shape of the patient's nose. This shape of oral hole may allow the interface 3000 to be particularly compact, and not be substantially wider than a width of the patient's nares.

5.3.1.5 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

In some forms, the plenum chamber 3200 (or at least a portion of the plenum chamber 3200) and the seal-forming structure 3100 are formed from a single homogeneous piece of material (e.g., molded silicone). A combination of the seal-forming structure 3100 and the plenum chamber 3200 may be considered a cushion.

5.3.2.1 Angle of Nasal Portion is Adjustable

With particular reference to FIGS. 9, 10 and 16 to 18-2, in one form of the technology a first anterior wall portion 3240 of the nasal portion 3202 of the plenum chamber 3200 is more flexible than an immediately adjacent region of the oral portion 3201. The first anterior wall portion 3240 may be provided adjacent a boundary 3241 of the nasal and oral portions of the plenum chamber 3200. In embodiments the first anterior wall portion 3240 may be symmetrical about the mid-sagittal plane and may extend across at least 50% of the width of the nasal portion 3202 of the plenum chamber, for instance at least 80%. In some embodiments the first anterior wall portion 3240 may extend across substantially the entire width of the nasal portion 3202 of the plenum chamber.

In some forms of the technology a second anterior wall portion 3242 is less flexible than the immediately adjacent portions of the anterior wall. In some embodiments the second anterior wall portion 3242 is immediately adjacent the first anterior wall portion 3240 on an opposite side to the boundary 3241 of the nasal and oral portions of the plenum chamber. In embodiments the second anterior wall portion 3242 may be symmetrical about the mid-sagittal plane and may extend across at least 50% of the width of the nasal portion 3202 of the plenum chamber, for instance at least 80%. In some embodiments the second anterior wall portion 3242 may extend across substantially the entire width of the nasal portion 3202 of the plenum chamber.

The flexible first anterior wall portion 3240 may allow the patient contacting portions 3110 of the second seal forming structure 3102 to pivot or hinge about a region on the posterior side of the interface 3000. This may assist in allowing the interface to accommodate patients with a variety of angles between the bottom of the nose and the top lip (i.e. nasolabial angles).

In embodiments featuring a corner or ridge 3120 between the first and second seal forming structures 3101, 3102, such as have been described above, the patient contacting portions 3110 may pivot or hinge about an area at or adjacent the corner or ridge 3120. In embodiments provided with one or more support portions 3260 (described further below), the hinging or pivoting region may be immediately superior to the support portions 3260.

As shown in FIG. 9, the first anterior wall portion 3240 may have a superior boundary 3243 and an inferior boundary 3244. One or both of the superior and inferior boundaries 3243, 3244 may be curved, for example such that a central portion of the boundary is inferior to the lateral portions, as shown. The first anterior wall portion 3240 may be substantially the same height across its width (i.e., the superior and inferior boundaries may be substantially parallel) or the height may vary across the width, for example such that the height of a central portion of the first anterior wall portion 3240 is greater than the height of the lateral portions, as shown in the embodiment in FIG. 9. Varying the curvature of one or both of the boundaries 3243, 3244 and/or the height of the first anterior wall portion 3240 may change the stiffness of the first anterior wall portion 3240, that is, its resistance to collapsing or folding in response to forces on the patient-contacting portions 3110 of the second seal forming structure 3102.

Similarly, the second anterior wall portion 3242 may have a superior boundary 3247 and an inferior boundary 3248. In some forms of the technology the inferior boundary 3248 of the second anterior wall portion 3242 is the same as the superior boundary 3243 of the first anterior wall portion 3240. Both the superior and inferior boundaries 3247, 3248 of the second anterior wall portion 3242 may be curved, for example such that a central portion of the boundary is inferior to the lateral portions. The second anterior wall portion 3242 may be substantially the same height across its width (i.e., the superior and inferior boundaries may be substantially parallel) or the height may vary across the width, for example such that the height of a central portion of the second anterior wall portion 3242 is less than the height of the lateral portions.

In some forms of the technology other ways of configuring the first anterior wall portion 3240 to have a required stiffness may be used, in addition to or alternatively to curved boundaries. For example, the thickness of the first anterior wall portion 3240 may be selected to provide a required stiffness. In examples the first anterior wall portion 3240 may be thinner than the immediately adjacent portions of the plenum chamber wall. Additionally and/or alternatively, the first anterior wall portion 3240 may extend in a superior direction around a lateral edge of the second anterior wall portion 3242, as shown in FIG. 21, thereby providing a reduced stiffness/resistance to compression or collapse compared to embodiments in which the first anterior wall portion 3240 is not shaped this way.

The second anterior wall portion 3242 (e.g., the band 3270) may assist in preventing collapse of the nasal portion 3202, and may provide support for the patient-contacting portions 3110 of the second seal forming structure 3102, which are typically relatively thin. Insufficiently supported patient contacting portions may suffer from blowout of the sealing engagement with the patient's face. In one form the second anterior wall portion 3242 is thicker than the immediately adjacent portions of the plenum chamber wall. In certain forms the second anterior wall portion 3242 is provided as a thickened band of material 3270, as shown in FIGS. 16-19. The first and second anterior wall portions 3240, 3242 may be made from the same material, for example as part of an integrally moulded shell 3250.

In some forms, the first and second anterior wall portions 3240, 3242 may include different thicknesses. For example, the thickness of the second anterior wall portion 3242 may be greater than the thickness of the first anterior wall portion 3240, which may provide the increased stiffness in the second anterior wall portion 3242 (e.g., as compared to the first anterior wall portion 3240). Specifically, the second anterior wall portion 3242 may be a band 3270 that may extend into the cavity 3272 of the plenum chamber 3200. For example, the band 3270 may extend past the first anterior wall portion 3240, and extend toward a patient wearing the patient interface 3000. An exterior surface of the nasal portion 3202 may be substantially smooth, while an interior surface of the nasal portion (e.g., within the cavity 3272) may be stepped (or otherwise include a discontinuity).

As shown in FIGS. 16-1 and 16-2, the first anterior wall portion 3240 may act as a hinge and allow the nasal portion 3202 to bend. The first anterior wall portion 3240 may be the thinnest region of the nasal portion 3202, and therefore may be the most susceptible to a bending moment. The increased thickness of the band 3270 directs the bending moment away from the second anterior wall portion 3242, and toward the thinner first anterior wall portion 3240. A larger height of the band 3270 (i.e., a larger distance between the superior and inferior boundaries 3247, 3248) may also make the nasal portion 3202 stiffer and less capable of bending about the first anterior wall portion 3240. The first and second anterior wall portions 3240, 3242 may move in the anterior direction (e.g., away from the patient) as bending occurs.

As shown in FIGS. 18-1 and 18-2, the superior boundary 3243 of the first anterior wall portion 3240 is not the same as the inferior boundary 3248 of the second anterior wall portion 3242. Instead, the superior boundary 3243 is a least partially more superior than the inferior boundary 3248, and may be at least partially aligned with the superior boundary 3247 of the second anterior wall portion 3242. This allows the first anterior wall portion 3240 to be disposed at least partially alongside of the band 3270 (e.g., and surround the band 3270 on two or more sides). In other words, the first anterior wall portion 3240 may be disposed on at least one of the ends of the band 3270. This may provide the first anterior wall portion 3240 with greater flexibility so that the nasal portion 3202 is able to bend further (e.g., in the anterior direction).

As shown in FIG. 21-1, the nasal portion 3202 may also be formed without a hinge. In other words, a band may not be formed on the second anterior wall portion 3242, so that the first and second anterior wall portions 3240, 3242 have substantially uniform thicknesses. The nasal portion 3202 may still be able to bend even without band because it may be constructed from silicone, which permits some compliance in the nasal portion 3202 to accommodate different nasolabial angles.

5.3.2.2 Flexible Shell

In some forms of the technology the shell 3250 may be made from a rigid material such as polycarbonate. However, in other forms of the technology the shell 3250, or portions of the shell 3250, may be somewhat flexible. For example, in examples the shell 3250 may be formed from a material which has a Young's modulus of 0.4 GPa or lower, for example foam. In some forms of the technology the shell 3250 may be made from a material having Young's modulus of 0.1 GPa or lower, for example rubber. In other forms of the technology the shell 3250 may be made from a material having a Young's modulus of 0.7 MPa or less, for example between 0.7 MPa and 0.3 MPa. An example of such a material is silicone.

In examples, the shell 3250 and one or both of the first and second seal forming structures 3101, 3102 may be formed from the same material (e.g., silicone, textile, etc.).

In some forms of the technology (see e.g., FIGS. 23 to 28-2), the shell 3250 may be constructed substantially entirely from a flexible material, which may provide the shell 3250 with the greatest freedom of movement (i.e., substantially no rigid and/or thickened portions that limit bending). The shell 3250 may be sufficiently flexible that one or more components are added to provide a required stiffness in one or more areas or regions of the shell 3250 (e.g., a region that contacts the area 1010). For example, one or more of a vent module; a connection port; a headgear connector; a headgear connector connected to a rigidising arm and a rigidising member may be connected to the shell 3250 in such a way as to increase the stiffness of the plenum chamber 3200 in the area adjacent the component, for example as described further below. In some forms of the technology such components may be releasably connectable to the flexible shell 3250. Additionally or alternatively one more components may be permanently connected to the shell 3250, for example by bonding and/or overmolding. The rigidising member may also serve to increase the stiffness and/or support the shape of the seal forming structure 3100.

In some forms of the technology the shell 3250 may be generally flexible but may comprise stiffening portions having greater thickness than immediately adjacent portions of the shell 3250. Such stiffening portions may be configured as ribs or bands, for example extending laterally across the shell and/or extending in a superior-inferior direction, although many other configurations are possible. In some forms the shell may comprise a substantially rigid portion, for example manufactured from polycarbonate, as well as a somewhat flexible portion.

In some forms of the technology it may be preferable for a central portion 3251 of the anterior side of the oral portion 3201 of the plenum chamber to have a greater stiffness than the remainder of the plenum chamber 3200. In some forms of the technology the area of increased stiffness may be immediately inferior to the nasal portion 3202, as shown in FIG. 21 and described further below, and/or immediately superior to the oral portion 3201. In one form of the technology, a portion of, or the entirety of, the first anterior wall portion 3240 may be an area of increased stiffness, rather than an area of increased flexibility. Providing increased stiffness in one or more of these areas may provide shape stability and may limit the extent to which the shell 3250 deforms as a result of headgear forces. Excessive deformation may result in the second seal forming structure 3102 occluding the nares. Avoiding such deformation may be particularly advantageous to patients with relatively wide noses, and may be less important, or in some cases undesirable, for patients with narrow noses. In addition, the areas of increased stiffness described may assist in reducing torsional deformation of the interface which may otherwise result in one side of the second seal forming structure 3102 losing contact with the patient's nose, thereby creating a leak path.

As shown in FIGS. 21 and 21-1, in one form of the technology the shell 3250 may be provided with a rigid portion 3263, or at least a portion which is more rigid than the remainder of the shell, to which one or more connection ports 3600 are provided, e.g. moulded. In one form of the technology a rigid portion 3263 may be made from polycarbonate. This may provide more rigidity than a shell made exclusively of silicone. In one form the technology holes forming a vent 3400 are moulded into the rigid portion 3263. In some forms of the technology connectors 3310 for a positioning and stabilising structure are mounted on arms 3320 which provide some rigidity to the shell.

In one form of the technology the rigid portion 3263 extends laterally across the anterior of the plenum chamber near a superior boundary of the first anterior wall portion 3240, for example immediately below the second anterior wall portion 3242. The rigid portion 3263 may extend continuously between the connection ports 3600, and may provide an airflow path for the flow of pressurized air entering the plenum chamber 3200 through the connection ports 3600.

In some forms of the technology the connection ports 3600 may have a substantially elliptical shape in cross-section. The connection ports 3600 may be orientated such that a centreline of each port is substantially parallel to an exterior surface of the plenum chamber adjacent the port.

In some forms of the technology the rigid portion 3263 may protrude in an anterior direction relative to an adjacent face of the first anterior wall portion 3240, and may be shaped to increase resistance to bending.

In some forms of the technology (see e.g., FIG. 21), the connectors 3310 and arms 3320 are provided inferior of the connection ports 3600, toward the lateral edges of the plenum chamber 3200. The connectors 3310 may be provided at lateral ends of the arms 3320. The connectors 3310 may provide additional rigidity to the plenum chamber 3200 and/or the seal forming structure 3100.

In some forms of the technology (see e.g., FIG. 21-1), the connectors 3310 do not include arms 3320, and are instead connected directly to the plenum chamber 3200. This may make the plenum chamber 3200 more flexible than the plenum chamber 3200 of FIG. 21.

FIG. 22 shows a plenum chamber 3200 with a vent mounting aperture 3410 into which a suitable vent portion or module may be inserted. The vent portion may be made from a relatively stiff material to increase the stiffness of the plenum chamber. In some forms of the technology the vent mounting aperture 3410 may be substantially elliptical in shape, with the minor axis of the ellipse being substantially parallel to a sagittal plane.

In the embodiment shown in FIG. 22 the vent mounting aperture is provided toward a superior border of the oral portion 3201 of the plenum chamber 3200.

The embodiment shown in FIG. 22 is provided with connectors 3310 for a positioning and stabilising structure. The connectors 3310 may be mounted in relatively thicker regions of the shell 3250. In the embodiment shown the connectors 3310 are inferior of the vent mounting aperture 3410 and toward the lateral sides of the plenum chamber 3200. In some forms of the technology the connectors 3310 are substantially circular magnetic headgear connectors.

While inlet or connection ports are not shown in the drawings of the plenum chamber shown in FIGS. 7-19, those skilled in the art will appreciate that in practice one or more inlet ports will be provided, for example inlet ports 3600 as shown in FIGS. 21-22. The inlet ports 3600 allow connection of the interface to an air circuit 4170, as described further herein. In some forms of the technology one or more components of the air circuit 4170 may also act as components of a positioning and stabilising structure.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material, e.g. translucent silicone. The use of a translucent material can reduce the obtrusiveness of the patient interface, and help improve compliance with therapy.

In certain forms of the present technology, dedicated stiffening members or rigidising members (e.g., with no other function) may be included on the plenum chamber 3200. These members may be formed from a material more rigid than the plenum chamber 3200 (e.g., than the silicone). The dedicated stiffening members may be overmolded to the plenum chamber 3200 to provide more stiffness than the rigid portion 3263 of the shell 3250 or the arms 3320.

5.3.3 Support Portions

As best seen in FIGS. 12 and 14-18, in one form of the technology support portions 3260 are provided on opposite sides of the interface 3000 between the second seal forming structure 3102 and an anterior wall of the plenum chamber 3200. As shown in FIG. 12, in an example each support portion 3260 extends to a lateral edge of the interface.

The support portions 3260 do not act as undercushions and are instead configured to resist or hinder compression in the anterior-posterior direction. The support portions 3260 thereby support and/or stiffen portions of the second seal forming structure 3102 which engages the patient's lip superior. In particular, the support portions 3260 may support and/or stiffen regions of the second seal forming structure 3102 that may contact an area 1010 of the patient's face proximate the entrances to the nares where the ala meets the area above the lip superior, as shown in FIG. 20. In other words, the area 1010 may be directly inferior to each of the lower corners of the patient's nose.

The support portions 3260 assist in ensuring that creases do not form in the seal forming structure 3100. Creases in a seal forming structure may form as a result of a very flexible seal forming structure, with a large radius of curvature, conforming to a patient's face. The seal forming structure may fold over itself, or crease, as a result of being too flexible, and lead to leaks in the seal forming structure. Creasing may be particularly of concern where the seal forming structure seals against the area 1010 of the patient's face. The support portions 3260 may be particularly advantageous when the seal forming structure is configured to create a corner and/or ridge 3120 as described herein. The corner and/or ridge 3120 may be a sharper curve (e.g., a curve with a lower radius of curvature) as compared to seal forming structures without the support portions 3260. The support and/or stiffness added by the support portions 3260 decreases the ability of the second seal forming structure 3102 from conforming to the patient's face. In order to retain comfort for the patient, the corner and/or ridge 3120 is selected and/or sized to substantially match the geometry (e.g., contours) of the patient's face. For example, the seal forming structure 3100 for a particular patient may be selected from a variety of sizes in order to substantially conform to the nasal alar region (i.e., proximate to the area 1010). The sharper curvature permits the second seal forming structure 3102 to seal against the various crevices around the patient's nose with reduced likelihood that creases will form.

As seen in FIGS. 14-16 in particular, in one form of the technology the support portions 3260 are connected to the anterior side of the oral portion 3201 of the plenum chamber adjacent the boundary 3241 of the oral portion 3201 and the nasal portion 3202. In some embodiments the support portion 3260 may be curved when viewed in cross-section parallel to a sagittal plane (as shown in FIGS. 16-18) and/or when viewed in cross-section parallel to a frontal plane (as shown in FIGS. 14 and 15). The curvature may be positive or negative. In the illustrated example, the curvature may be negative (e.g., with respect to the patient's nose). In some examples, a lateral side wall portion 3245 of the plenum chamber 3200 may curve inwardly adjacent the boundary 3241 with the nasal portion 3202, and the support portion 3260 may be substantially contiguous with an adjacent lateral side wall portion 3245. As shown in FIG. 18, when viewed in cross-section parallel to a sagittal plane, at least a portion of the support portion 3260 may reduce in thickness between a first end 3261 adjacent the anterior wall of the plenum chamber 3200 and a second end 3262 adjacent the seal forming structure 3100. For example, the support portion 3260 may be thicker proximate to the first end 3261, which may assist in providing increased support and/or stiffness to the second seal forming structure 3102. In some examples, the support portion 3260 may vary between a thickness of 0.1 mm (e.g., proximate to the second end 3262), and a thickness of 3.5 mm (e.g., proximate to the first end 3261). In some examples, the support portion 3260 may vary between a thickness of 0.3 mm (e.g., proximate to the second end 3262), and a thickness of 3 mm (e.g., proximate to the first end 3261). In some examples, the support portion 3260 may vary between a thickness of 1.3 mm (e.g., proximate to the second end 3262), and a thickness of 2.5 mm (e.g., proximate to the first end 3261).

Support portions 3260 with different geometries may be used for different patients. For example, patient's that require more support and/or stiffness in the second seal forming structure 3102 may use a seal forming structure 3100 with a thicker (e.g., proximate to the first end 3261 and/or at any location along the length) and/or more curved (e.g., lower radius of curvature) support portion 3260. For example, patients that want a more flexible second seal forming structure 3102 may use a seal forming structure 3100 with a thinner (e.g., proximate to the first end 3261 and/or at any location along the length) and/or less curved (e.g., greater radius of curvature) support portion 3260.

As seen in particular in FIGS. 14 and 15, in one form of the technology the support portion 3260 is connected to the oral portion 3201 of the plenum chamber adjacent a boundary of a lateral side wall portion 3245 of the oral portion 3201 and a lateral side wall portion 3246 of the nasal portion 3202.

In some forms of the technology, the support portions 3260 are shaped to provide a substantially clear flow path from the oral portion 3201 of the plenum chamber to the nasal aperture(s) 3135 during inspiration. In some forms of the technology no part of either support portion 3260 is directly inferior to the nasal aperture(s) 3135.

5.3.4 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

FIGS. 21 and 22 show embodiments which are provided with connectors 3310, e.g. magnetic connectors, for connection to a positioning and stabilising structure.

5.3.4.1 Frame

As shown in FIGS. 23 to 28-2, a frame 3350 is coupled to the plenum chamber 3200 and assists in maintaining the therapeutically effective position of the seal-forming structure 3100. The plenum chambers 3200 illustrated in FIGS. 23 to 28-2 specifically illustrate an elbow 3500 connected in front of the patient's face, although the frame may be used with other styles of plenum chambers 3200 (e.g., plenum chambers 3200 of FIGS. 21-22 used with conduit headgear).

In some forms, the frame 3350 is constructed from a rigid or semi-rigid material, and provides support to the seal-forming structure 3100 and/or the plenum chamber 3200. For example, the frame 3350 may assist in maintaining the shape of the seal-forming structure 3100 and/or the plenum chamber 3200 in order to reduce leaks of pressurized air as a result of folding and/or creasing as the seal-forming structure 3100 engages the patient's face.

In some forms, the frame 3350 provides at least one connection point 3352, which may assist in indirectly connecting the headgear straps 3354 to the plenum chamber 3200 and/or seal-forming structure 3100. The connection point 3352 may be a loop (e.g., with a fully formed perimeter) that receives a portion of the headgear straps 3354. For example, a length of a left superior headgear strap 3356 may be threaded through a first loop 3352a, and pulled away from the plenum chamber 3200 in order to apply tension through the left superior headgear strap 3356. The left superior headgear strap 3356 may be folded against itself and retained in the selected length (e.g., using Velcro, magnets, adhesives, etc.) in order to maintain the applied tension. Similar steps may be performed regarding adjusting the tension in the right superior headgear strap 3358 in a second loop 3352b.

In some forms, each loop 3352a, 3352b may be oriented so that a force vector applied by the respective superior headgear strap 3356, 3358 is substantially perpendicular to a loop inner surface 3351, against which the superior headgear straps 3356, 3358 contact. As shown in FIG. 23, the right superior headgear strap 3358 engages the loop 3352b in substantially the center of the loop inner surface 3351. When the right superior headgear strap 3358 is tightened, the force vector is applied in a substantially straight direction, and not oblique relative to the loop inner surface 3351. This may improve the sealing of the seal-forming structure 3100, as the forces are directed along the arms 3362, and not oblique relative to the arms 3362, which may require the superior headgear straps 3356, 3358 to be further tightened to receive the same sealing effects (e.g., at the detriment to patient comfort), and/or may prevent the seal-forming structure 3100 from properly engaging the patient's face (e.g., leading to leaks).

As shown in FIG. 27-2, certain forms of the loops 3352a, 3352b may include an eyelet cut 3353, which may be formed on the patient side of the respective loop 3352a, 3352b (e.g., the side proximate to the patient's skin while in use). The eyelet cut 3353 may form a region of reduced thickness along the perimeter of the respective loop 3352a, 3352b. The eyelet cut 3353 may extend around a portion of the perimeter of the respective loop 3352a, 3352b (e.g., less than 360°). In the illustrated example, the respective headgear strap 3354 may contact the eyelet cut 3353 when received through the loop 3352a, 3352b. The reduced thickness of the eyelet cut 3353 may result in less material being used to manufacture the loops 3352a, 3352b, which may lead to lower manufacturing times and/or lower manufacturing costs. The eyelet cut 3353 may also (or instead of) lead to reduced skin marks, and improved patient comfort.

In one form, at least one of the loops 3352a, 3352b may not be completely formed around an outer perimeter. In other words, the loops 3352a, 3352b may be C-shaped and/or U-shaped. The left and/or right superior headgear straps 3356, 3358 may be individually folded against themselves, and then inserted through into the respective loop 3352a, 3352b. This may allow the patient to maintain the same length adjustment in the respective superior headgear strap 3356, 3358, when the seal-forming structure 3100 is being removed from the therapeutically effective position.

In some forms, the frame 3350 includes a central portion 3360 that is coupled to the plenum chamber 3200. The central portion 3360 may have an annular shape, and may have a profile that corresponds to the shape of the plenum chamber 3200 (e.g., approximating a positive domed curvature).

In one form, a single size of the central portion 3360 may be used with a variety of sizes of plenum chambers 3200 and/or seal-forming structures 3100. For example, the seal-forming structure 3100 may come in multiple sizes (e.g., small, medium, large, etc.) and/or shapes (e.g., narrow, wide, etc.) in order to better seal against patients with a variety of facial shapes. An engagement region of the central portion 3360 may remain substantially the same regardless of the size of the plenum chamber 3200 and/or seal-forming structure 3100. Thus, the central portion 3360 may be coupled to a variety of shaped and/or sized cushions, and provide substantially the same support.

In one form, the central portion 3360 may be removable coupled to the plenum chamber 3200. A patient may use the same frame 3350 with multiple plenum chambers 3200. This may be useful when the patient is first beginning the therapy, and is trying different sized plenum chambers 3200, in order to find an appropriate fit. Removing the frame 3350 may also be helpful when cleaning the patient interface 3000, as the different elements of the patient interface 3000 may be cleaned separately, to help ensure a more thorough clean.

In some forms, the frame 3350 includes arms 3362 that extend away from the central portion 3360. The loops 3352a, 3352b are formed at ends of the arms 3362. In use, the arms 3362 may extend at least partially in the posterior direction, which may position the loops 3352a, 3352b more posterior than the plenum chamber 3200 and/or the seal-forming structure 3100. The arms 3362 may also extend in the lateral direction (e.g., left or right respectively) so as to generally extend along contours of the patient's face.

In some forms, the arms 3362 engage a portion of the patient's face while the patient interface 3000 is worn by the patient. For example, the arms 3362 may contact the patient's cheeks. The arms 3362 may be shaped in order to correspond to the curvatures of a patient's face (e.g., extend in posterior and lateral directions).

In some forms, the arms 3362 may not substantially stretch as a result of the tension applied by the respective headgear strap 3356, 3358 via the respective loop 3352a, 3352b (e.g., the arms 3362 may be rigidizers and/or may be inextensible). Tension may be transferred along the arm 3362 to the plenum chamber 3200 and/or seal-forming structure 3100 in order to maintain the therapeutically effective pressure and limit leaks from occurring.

In one form, the arms 3362 are constructed from a material that is more flexible than the material used to construct the central portion 3360. The two materials may be molded together so that the frame 3350 is constructed in an integral, one-piece construction. The arms 3362 may have some rigidity in order to assist in maintaining their shape. However, the arms 3362 may be bendable so that a patient may adjust the shape in order to correspond to their facial structure. Allowing a patient to adjust the shape of the arms 3362 may increase the comfort experienced by the patient, which may increase patient compliance with the therapy. In this way, the arms 3362 may bend or flex relative to the central portion 3360 (e.g., because of a cantilevered configuration), but may be unable to stretch further in the posterior direction (e.g., because of its inextensibility). Additionally, the relatively flexible material used to construct each of the arms 3362 may assist in reducing facial markings, and increase patient comfort.

In one form, the arms 3362 and the central portion 3360 are constructed from the same material. This material provides enough flexibility in order to permit shape adjustment, and also provides enough rigidity in order to maintain the adjusted shape. The central portion 3360 may be more rigid than the arms 3362 as a result of being coupled to the plenum chamber 3200. In addition or instead of, the central portion 3360 may be thicker than the arms 3362, which may also cause an increased rigidity of the central portion 3360. Each arm 3362 is formed as a cantilevered shape, so that the ends proximate to the respective loop 3352a, 3352b are unsupported. Additionally, the thickness of the frame 3350 may decrease along the length of each arm 3362 in the direction of the respective loop 3352a, 3352b (see e.g., FIG. 27-1). This may provide each arm 3362 with the flexibility necessary to be bent and/or shaped in order to substantially correspond to a shape of the patient's face (e.g., cheek). Decreasing the width of each arm 3362 may also reduce cheek contact between the respective arm 3362 and the patient's cheek, which may improve patient comfort. Decreasing the width along the length of each arm 3362 may also allow for greater flexibility proximate each respective loop 3352a, 3352b.

In some forms, the fixed end of each arm 3362 may have a thickness of between approximately 2 mm and approximately 7 mm. In some forms, the fixed end of each arm 3362 may have a thickness of between approximately 2.5 mm and approximately 6 mm. In some forms, the fixed end of each arm 3362 may have a thickness of between approximately 3 mm and approximately 5 mm. In some forms, the fixed end of each arm 3362 may have a thickness of approximately 4 mm.

In some forms, the free end of each arm 3362 may have a thickness of between approximately 0 mm and approximately 4 mm. In some forms, the fixed end of each arm 3362 may have a thickness of between approximately 0.5 mm and approximately 3 mm. In some forms, the fixed end of each arm 3362 may have a thickness of between approximately 1 mm and approximately 2.5 mm. In some forms, the fixed end of each arm 3362 may have a thickness of approximately 2 mm.

As shown in FIG. 27-3, some forms of the cross-section of each arm 3362 may be substantially rectangular. Corners (e.g., one corner, two corners, four corners, etc.) of the substantially rectangular shape may be rounded. This may assist in improving patient comfort by reducing sharp surfaces that contact the patient's skin. Each arm 3362 may also have a height that is greater than its thickness. The height may be designed to comfortably distribute pressure across the patient's skin (e.g., by increasing the height), without obstructing the patient's peripheral vision, or otherwise causing the patient discomfort.

In some forms, the height of each arm 3362 may be between approximately 5 mm and approximately 15 mm. In some forms, the height of each arm 3362 may be between approximately 6.5 mm and approximately 13.5 mm. In some forms, the height of each arm 3362 may be between approximately 8 mm and approximately 12 mm. In some forms, the height of each arm 3362 may be between approximately 9.5 mm and approximately 10.5 mm. In some forms, the height of each arm 3362 may be approximately 10 mm.

As shown in FIGS. 26-4 and 26-5, certain forms of the frame 3350 may permit pivotable movement between each arm 3362 and the central portion 3360. The pivotable movement may be different than the bending movement described above in that the a pivot point 6012 may connect each arm 3362 to the central portion 3360, and allow the entire arm 3362 to move substantially the same angular distance. Each arm 3362 may also be able to bend, in addition to pivoting, as described above.

In one form, the pivot points 6012 are disposed in approximately the same position on either side of the frame 3350. In other words, each arm 3362 may be connected to the central portion 3360 at substantially the same height, and each arm 3362 may extend approximately the same length past the pivot point 6012. This may allow the patient to make mirrored adjustments to the arms 3362. The patient may then flex or bend each arm individually in order to make adjustments specific to one side.

In one form, each pivot point 6012 is a living hinge. In other words, the frame 3350 may be constructed from a substantially uniform material (or a transition between each arm 3362 and the central portion 3360 may be constructed from a substantially uniform material). The thickness at each hinge 6012 may be significantly less than the thicknesses of the arm 3362 and the central portion 3360 immediately adjacent to the hinge 6012. For example, the hinge 6012 may be formed as a groove on a surface of the frame 3350 that faces away from the patient while in use. Uniformly and integrally constructing the hinge 6012 out of substantially the same material as the arms 3362 and the central portion 3360 may assist in reducing manufacturing costs (e.g., as compared to including a hinge constructed of a different material).

Each arm 3362 may be pivotable about the respective hinge 6012 between a first position and a second position. The loops 3352a, 3352b may be spaced closer together in the second position than in the first position.

In one form, the first position may be a relaxed position, and the second position may be a biased position. The arms 3362 may move to the second position when an external force is applied, and may return to the first position when the external force is removed.

In one form, the arms 3362 may also be positioned in either the first positon or the second position without continued application of an external force. The arms 3362 may be moved into the second position so that the arms 3362 overlap one another (e.g., like eyeglasses). This may assist in providing a small footprint for packaging and/or storage.

In other forms (not shown), each arm 3362 may be separate from the central portion 3360, and may be coupled to the central portion 3360 with a rotational hinge (e.g., a pin joint). In still other forms, each arm 3362 may be coupled to the central portion 3360 by overmolding a flexible in between, which may allow for some pivotable movement.

In some forms, the frame 3350 further includes at least one secondary connection point 3364 that is spaced apart from the loops 3352a, 3352b. The secondary connection point(s) 3364 provides an additional connection location, which may further assist in indirectly connecting the headgear straps 3354 to the plenum chamber 3200 and/or seal-forming structure 3100.

In certain forms, the frame 3350 includes two secondary connection points 3364 (e.g., a left secondary connection point 3364a, and a right secondary connection point 3364b). The secondary connection points 3364a, 3364b may be inferior to the loops 3352a, 3352b while the patient interface 3000 is worn by the patient. The headgear straps 3354 may further include a left inferior headgear straps 3366 and a right inferior headgear strap 3368, each configured to couple to the respective secondary connection point 3364a, 3364b. The headgear 3354 as a whole may then be able to provide a force to the superior and inferior regions of the seal-forming structure 3100 and/or the plenum chamber 3200.

In certain forms, the secondary connection points 3364a, 3364b are formed directly on the central portion 3360. The secondary connection points 3364a, 3364b may be more anterior than the loops 3352a, 3352b while the patient interface 3000 is worn by the patient.

In certain forms, the secondary connection points 3364a, 3364b may be constructed from a single component, which may assist in reducing tooling and/or manufacturing costs.

In certain forms, the left and/or right inferior headgear straps 3366, 3368 are removably coupled to the respective secondary connection point 3364a, 3364b. The secondary connection points 3364a, 3364b may be magnetic, and a left and/or right inferior headgear straps 3366, 3368 may be threaded through a magnet 3370 with an opposite polarity as the secondary connection points 3364a, 3364b. The length of the left and/or right inferior headgear straps 3366, 3368 may be adjusted by folding the respective strap 3366, 3368 on itself (e.g., as done with the left and/or right superior headgear straps 3356, 3358). Each magnet 3370 may be removed from the respective secondary connection point 3364a, 3364b, without changing the length adjustment of the left and/or right inferior headgear straps 3366, 3368. A patient may be able to don and/or doff the patient interface 3000 while only removing the magnets 3370 from the respective secondary connection points 3364a, 3364b (e.g., without having to remove the left and/or right superior headgear straps 3356, 3358 from the respective loops 3352a, 3352b).

As shown in FIGS. 28-1 and 28-2, each secondary connection point 3364a, 3364b may be constructed in order to improve retention with the respective magnet 3370. An outer casing 3376 of each secondary connection point 3364a, 3364b may include a substantially planar (e.g., flat) surface 3378, and a lip 3380 extending from the planar surface 3378.

In the illustrated example, the outer casing 3376 may have a substantially elliptical shape, and the lip 3380 may extend proximate to a vertex of the planar surface 3378. The lip 3380 may also extend around only a portion of the planar surface 3378 (e.g., less than 360°). In some examples, the lip 3380 may extend less than 180° around the planar surface 3378 (e.g., the lip 3380 may not extend to either co-vertex of the substantially elliptical planar surface 3378).

As shown in FIG. 28-2, each secondary connection point 3364a, 3364b may be coupled to the frame 3350 so that the lip 3380 is disposed proximate to a center of the frame 3350. In other words, each secondary connection point 3364a, 3364b may be oriented so that the lip 3380 is disposed proximate to an elbow 3500 when the frame 3350 is coupled to the plenum chamber 3200.

The magnet 3370 includes a substantially planar surface that may engage the substantially planar surface 3378 of the outer casing 3376. While engaging the planar surface 3378, the magnet 3370 may be magnetically coupled to the magnetic element 3382 of the secondary connection point 3364a, 3364b. An overhang 3384 may be spaced apart from the magnet 3370. As illustrated, the overhang 3384 may be positioned on one side of the lip 3380 (e.g., an inner side) and the magnet 3370 may be positioned on the other side of the lip 3380 (e.g., an outer side). In use, the patient may adjust the length of a respective inferior headgear strap 3366, 3368. Tightening one of the inferior headgear straps 3366, 3368 may apply a force directed away from the center of the frame 3350 (e.g., in a laterally outward direction). This force may be greater than a magnetic force between the magnet 3370 and the magnetic element 3382, and may cause the magnet 3370 to move relative to the planar surface 3378.

The overhang 3384 may prevent the magnet 3370 from becoming disengaged from the magnetic material 3382 as a result of tightening the respective inferior headgear strap 3366, 3368. As the magnet 3370 begins to move, the overhang 3384 may contact the lip 3380, limiting further movement away from the center of the frame 3350. Engagement between the lip 3380 and the overhang 3384 therefore assist in reducing accidental disconnection of the magnet 3370 from the respective secondary connection point 3364a, 3364b when tightening the respective inferior headgear strap 3366, 3368, but does not limit the ability of the patient to move the magnet 3370 substantially perpendicular to the frame 3350 (e.g., in order to doff the positioning and stabilizing structure 3300).

As shown in FIG. 24, the engagement region of the plenum chamber 3200 may include a groove 3280. In the illustrated example, the groove 3280 may be included on the oral portion 3201 of the plenum chamber 3200, and may be radially outside of the central portion 3251. The central portion 3360 of the frame 3350 may be positioned within the groove 3280. The shape of the central portion 3360 may substantially correspond to the shape of the groove 3280, which may assist the patient in properly orienting the frame 3350 with respect to the plenum chamber 3200 (e.g., in examples where the frame 3350 is removably coupled to the plenum chamber 3200).

In some forms, the groove 3280 may have a completely formed perimeter with a substantially annular shape. The perimeter may have substantially the same length in any sized cushion.

In some forms, the groove 3280 is recessed relative to a remainder of the outer surface of the plenum chamber 3200. The recessed groove 3280 may not extend substantially into the plenum chamber 3200 and obstruct the patient's face. The groove 3280 may have substantially the same depth throughout its perimeter.

In some forms, a width of the groove 3280 may be less than a width of central portion 3360 of the frame 3350. The compliant nature of the cushion may allow the wider central portion 3360 to be received within the groove 3280. This may allow the central portion 3360 to couple to the groove 3280 via a press fit, friction fit, and/or snap-fit. The engagement between the groove 3280 and the central portion 3360 may assist in providing rigidity to the plenum chamber 3200 and/or the seal-forming structure 3100, because the rigidity of the frame 3350 (e.g., as compared to the plenum chamber 3200) may limit some flexibility of the plenum chamber 3200 alone.

In some forms, the cushion may be molded to the frame 3350 so that the groove 3280 may be created during a molding process. The material of the plenum chamber 3200 (e.g., silicone) may be molded at least partially around the central portion 3360 of the frame 3350, and may limit the central portion 3360 from being removed from the groove 3280.

As shown in FIG. 25, the frame 3350 may be constructed from multiple pieces (e.g., each constructed from a different material). For example, the central portion may be constructed from a first material (e.g., hard plastic). The arms 3362 may be coupled to the central portion 3360 (e.g., via glue, molding, etc.), and may be constructed from a second material (e.g., flexible plastic, foam, etc.) that is more flexible than the first material. A third material may be a magnetic material, and may be coupled to the central portion 3360 (e.g., via an adhesive). Once coupled together, the arms 3362 may be able to similarly move as in the integral, one-piece constructions described above.

As shown in FIGS. 26 and 27, the frame 3350 may be constructed from a single piece of material. For example, the frame 3350 may be constructed from a TPE material, like Hytrel. As described above, the material used in constructing the frame 3350 may provide both rigidity and flexibility to the frame 3350. The magnets 3370 may be overmolded (or otherwise coupled to) the central portion 3360.

In some forms, the central portion 3360 includes slots 3372, which may be formed on either lateral side of the central portion 3360. The slots 3372 may have a generally elongated shape (e.g., rectangular, elliptical, etc.), and may be completely formed within the boundary of the central portion 3360.

As shown in FIG. 27, some forms of the central portion 3360 may include a tapered slot 3372. Specifically, an opening to the slot 3372 may be wider proximate a posterior surface of the central portion 3360 (e.g., the surface in contact with the plenum chamber 3200). The opening to the slot 3372 may decrease uniformly toward the anterior surface of the central portion 3360.

FIG. 27 also illustrates that some forms of the arm 3362a (or arm 3362b) may include an indent or scallop 3373. The scallop 3373 may be formed on an inner surface of the arm 3362a, and may be positioned proximate to the patient's skin when the positioning and stabilizing structure 3300 is worn by the patient. The scallop 3373 reduces the thickness along a portion of the arm 3362a, and may decrease the likelihood of developing sink marks in the arm 3362a during a manufacturing (e.g., injection molding) process. The scallop 3373 may also result in less material being used to manufacture the arm 3362a, which may lead to lower manufacturing times and/or lower manufacturing costs.

Returning to FIGS. 26 to 26-2, the plenum chamber 3200 may include projections 3284 on the oral portion 3201. The projections may be elongated, and may have a similar shape to the slots 3372 (e.g., tapered). The projections 3284 may be disposed within the groove 3280 so that they cooperate with the frame 3350 during assembly.

As shown in FIG. 26-2, some forms of the projections 3284 may include an overhang 6000 that extends at least partially over the groove 3280. The overhang 6000 may be asymmetrically formed around the perimeter of the projection 3284. In other words, the overhang 6000 may extend further over the groove 3280 on one side than on the other side.

In some forms, the groove 3280 may also be asymmetrical. The groove 3280 may include an undercut 6004 on one side of the projection 3284, and an inclined surface 6008. The overhang 6000 may extend further over the undercut 6004 than over the inclined surface 6008. The length of the overhang 6000 extending over the undercut 6004 may limit the ability of the frame 3350 to be removed in a perpendicular direction from the plenum chamber 3200. The angle of the inclined surface 6008 may be directed toward the overhang 6000, and limit the ability of the frame 3350 to be removed in an oblique direction.

When the frame 3350 is being assembled to the plenum chamber 3200 (e.g., via a press fit, friction fit, snap-fit, etc.), the patient may align the projections 3284 with the slots 3372, so that the projections 3284 are received within the slots 3372 in use. The wider openings of the slots 3372 proximate to the posterior surface may assist the patient in aligning each projection 3284 within the respective slot 3372. The projections 3284 may be slightly wider than the anterior opening of each slot 3372, but are able to be received within the slot 3372 because of the flexible properties of the plenum chamber 3200 (e.g., being constructed from a resilient material like silicone). The projections 3284 may slightly deform as they enter the respective slot 3372 (e.g., as a result of the slot 3372 narrowing).

Once the projections 3284 are through the slot 3372, the projections 3284 may substantially return to their original shape. For example, the overhang 6000 may deform (e.g., elastically deform) as the slot 3372 receives the projection 3284, and may return to its initial position once the central portion 3360 is received within the groove 3280. The patient may experience this deformation as a tactile response, in order to more easily observe proper connection between the frame 3350 and the plenum chamber 3200. The overhangs 6000 of the projections 3284 may be wider than the anterior opening of the respective slot 3372 in a relaxed or initial position.

Additionally, the width of the undercut 6004 may be substantially the same as the central portion 3360 so that the frame 3350 is snuggly received within the groove 3280. The flexible material of the plenum chamber 3200 may allow the undercut 6004 to be slightly smaller than the central portion 3360, so that the undercut 6004 may flex and receive the frame 3350 via the press-fit, friction fit, snap-fit, etc.

Thus, the frame 3350 may not be easily removed from the plenum chamber 3200. The patient may have to apply a force to the frame 3350 in order to remove it from the groove 3280. This user applied force may allow the frame 3350 to be moved in either the perpendicular or oblique direction, and overcome the retention provided by the overhang 6000. For example, the patient may lift the frame 3350 from the region of the central portion 3360 that contacts the inclined surface 6008 in order to provide a force for disengaging the frame 3350 from the plenum chamber 3200.

This force may exceed a force produced by normal movements of the plenum chamber 3200 and/or seal forming structure 3100. In other words, the seal-forming structure 3100 and/or plenum chamber 3200 may move relative to the frame 3350 while the projections 3284 are received within the respective slot 3372. This may allow the seal-forming structure 3100 and/or the plenum chamber 3200 to flex and conform to a patient's face without coming loose from the frame 3350, and inadvertently causing the slots 3372 to disengage from the projections 3284.

In other forms, the plenum chamber 3200 may be molded to the frame 3350, and the projections 3284 may result from the molding process in order to permanently retain the position of the frame 3350 relative to the plenum chamber 3200.

As shown in FIG. 26-3, some forms of the frame 3350 may be oriented in order to reduce cheek contact while the connected frame 3350 and plenum chamber 3200 are worn by the patient. For example, the arms 3362a, 3362b may be oriented (e.g., curved) in order to substantially compliment at least a portion of the patient's face (e.g., their cheek). In some examples however, the entire length of each arm 3362 may not contact the patient's skin as a patient may feel it is uncomfortable to have a foreign object in contact with their face. Instead, a portion of each arm 3362 may be spaced apart from the patient's face so that a smaller surface area of the arm 3362 contacts the patient's face. While maintaining substantially the same curvature in each arm 3362, moving a contact point between each arm 3362 and the plenum chamber 3200 (e.g., via a manufacturing process) may change the total length of each arm 3362 that contacts the patient's face. For example, if each arm 3362 contacts the plenum chamber 3200 closer to the elbow 3500, a maximum gap between each arm 3362 and the patient's face is greater. This means that a greater portion of each arm 3362 will be spaced apart from the patient's face (e.g., as opposed to if each arm 3362 contacted the plenum chamber 3200 distal to the elbow 3500). Less contact between the each arm 3362 and the patient's face may improve patient comfort.

Additionally, each arm 3362 contacting the plenum chamber 3200 proximate to the elbow, and therefore distal to the posterior surface 3112, may produce less support at the lateral portions 3111 of the plenum chamber 3200 (e.g., because the rigid or semi-rigid arm engages less of the lateral portion 3111). The lateral portions 3111 may therefore have a greater degree of flexibility, and may be able to better conform to the shape of a patient's nose and create an effective seal.

As shown in FIGS. 26-4 and 26-5, some forms of the frame 3350 may include the hinges 6012 between each arm 3362 and the central portion 3360. The hinges 6012 may permit movement (e.g., pivotable movement) of the arms 3362 without affecting the connection between the frame 3350 and the plenum chamber 3200. In other words, pivoting either arm 3362 about the respective hinge 6012 may not cause the projection 3284 to disengage from the slot 3372.

In some forms, the patient may move the arms 3362 into the second position in order to provide a better fit. For example, the distance between the loops 3352a, 3352b in the first position may be larger than the size of an average patient's head. Accordingly, the patient may move the arms 3362 toward the second position in order to provide an appropriate fit (e.g., contact between the arms 3362 and the patient's head). The arms 3362 may be retained in the second position by adjustment of the superior headgear straps 3356, 3358 (i.e., the superior headgear straps 3356, 3358 may provide the external force).

Similarly to the arms 3362, the plenum chamber 3200 and/or the seal-forming structure 3100 may be larger than the size of the average patient's face. For example, the seal-forming structure 3100 may not snuggly engage the patient's mouth and/or nose. The plenum chamber 3200 and/or the seal-forming structure 3100 may also move toward a more compact position in order to better engage an individual patient's face.

As shown in FIG. 26-5, movement of the arms 3362 into the second position may directly cause the seal-forming structure 3100 and/or the plenum chamber 3200 to move to a more compact position. The arms 3362 may contact the plenum chamber 3200 along the second anterior wall portion 3242. The arms 3362 may also contact the second anterior wall portion 3242 proximate to a center of the plenum chamber 3200, and distal to the lateral portions 3111.

Pivoting movement of each arm 3362 about the hinge 6012 may provide an inwardly directed force to the plenum chamber 3200. This may reduce a distance between the lateral portions 3111 of the second seal-forming structure 3102, and snuggly position the second seal-forming structure 3102 against the patient's nose. Compressing the seal-forming structure 3100 and/or the plenum chamber 3200 may provide a better seal against the patient's face (e.g., by limiting the occurrence of leaks). Additionally, applying the inwardly directed force proximate to the center of the plenum chamber 3200 (e.g., as described with respect to FIG. 26-3) may limit creasing from forming in the seal-forming structure 3100 by limiting the total compression of the plenum chamber 3200.

As shown in FIG. 28, the frame 3350 may be shaped similarly to the frame in FIGS. 26 and 27. In other words, the frame 3350 may be constructed from a single material (e.g., with semi-rigid properties). The frame 3350 may be thicker proximate the central portion 3360, and thinner toward each respective loop 3352a, 3352b.

In some forms, the central portion 3360 of the frame 3350 may be substantially solid throughout, and may not include slots 3372, and the plenum chamber 3200 may not include projections 3284 within the groove 3280. Instead, the plenum chamber 3200 may include protrusions 3288 disposed radially inside of the groove 3280. The protrusions 3288 may be raised from the rest of the anterior surface of the plenum chamber 3200. The protrusions 3288 may also extend at least partially in a radially outward direction. In other words, the protrusions 3288 may extend at least partially over the groove 3280 (e.g., the protrusions 3388 are spaced apart from the groove 3280).

While assembling a removable frame 3350 to the plenum chamber 3200, a patient may be required to position the frame 3350 so that it extends into the groove 3280, and underneath of the protrusions 3288. Once the central portion 3260 is positioned, the protrusions 3288 may assist in retaining the central portion 3360 in place. To decouple the frame 3350 from the plenum chamber 3200, the patient may push on at least one of the protrusions 3288 (e.g., in a lateral direction toward the other protrusion 3288) so that the protrusion no longer extends over the groove 3280. In other forms, the plenum chamber 3200 may be molded to the frame 3350, the protrusions 3288 may prevent the central portion 3360 from being removed.

In some forms, the frame 3350 of any of the examples described above may be substantially flush with the outer surface of the plenum chamber 3200 when positioned within the groove 3280. The depth of the groove 3280 substantially corresponds to a thickness of the central portion 3360. Similarly, the shape of the central portion may substantially approximate the shape of the cushion as described above. The resulting assembly may have a substantially uniform surface. This assists in maintaining a low profile look of the patient interface 3000, because the frame 3350 is not projecting in front of the cushion where it may obstruct the patient's line of sight.

5.3.5 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

While no vent structures are shown in FIGS. 7-18, embodiments of the technology shown in FIGS. 7-18 may be provided with a suitable vent structure, for example in the plenum chamber (one example of which is shown in FIG. 21).

5.3.6 Decoupling Structure(s)

In one form the patient interface 3000 includes at least one decoupling structure 3500, for example, a swivel or a ball and socket. In some examples, the decoupling structure may be an elbow 3500 that is connected (e.g., removably connected, permanently connected, etc.) to the plenum chamber 3200 (e.g., a plenum chamber inlet port).

As shown in FIGS. 23-28, the central portion 3360 of the frame 3350 has an annular shape, so that a central region of the oral portion 3201 of the plenum chamber 3200 is not covered by the frame 3350. In some examples, the oral portion 3201 includes an opening for receiving the elbow 3500. The opening may be significantly wider than the opening for receiving the elbow 3500, so that the frame 3350 is completely spaced apart from the opening. In other words, there is a length between the inner edge of the central portion 3360 and the opening for receiving the elbow 3500. The arms 3362a, 3362b and the secondary connection portions 3342a, 3342b are each spaced apart from the opening and the elbow 3500, so that the headgear straps 3358 do not interfere with movement (e.g., rotation) of the elbow.

While not explicitly shown in the drawings of the plenum chamber shown in FIGS. 7-19, those skilled in the art will appreciate that in practice an elbow 3500 may be provided (e.g., as illustrated in FIG. 23), and allow connection of the interface to an air circuit 4170.

5.3.7 Connection Port

Connection port 3600 allows for connection (e.g., a removable connection via a snap-fit, a permanent connection, etc.) to the air circuit 4170. The patient interface 3000 may include two connection ports 3600, one on either side of the plenum chamber 3200. Conduits may connect to the connection ports 3600 in order to convey pressurized breathable gas to the patient. In some forms, the conduits may be conduit headgear, and may contact the patient's head. The conduits may extend toward the crown of the patient's head, where the decoupling structure 3500 is located.

5.3.8 Forehead Support

In one form, the patient interface 3000 includes a forehead support 3700.

5.3.9 Anti-Asphyxia Valve

In one form, the patient interface 3000 includes an anti-asphyxia valve.

5.3.10 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

5.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10$cmH_2O$, or at least 20 $cmH_2O$.

5.4.1.1 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules.

In other forms of the present technology, some portion or all of the algorithms 4300 may be implemented by a controller of an external device such as the local external device 4288 or the remote external device 4286. In such forms, data representing the input signals and/or intermediate algorithm outputs necessary for the portion of the algorithms 4300 to be executed at the external device may be communicated to the external device via the local external communication network 4284 or the remote external communication network 4282. In such forms, the portion of the algorithms 4300 to be executed at the external device may be expressed as computer programs stored in a non-transitory computer readable storage medium accessible to the controller of the external device. Such programs configure the controller of the external device to execute the portion of the algorithms 4300.

In such forms, the therapy parameters generated by the external device via the therapy engine module 4320 (if such forms part of the portion of the algorithms 4300 executed by the external device) may be communicated to the central controller 4230 to be passed to the therapy control module 4330.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Supplementary Gas Delivery

In one form of the present technology, supplementary gas, e.g. oxygen, 4180 is delivered to one or more points in the pneumatic path, such as upstream of the pneumatic block 4020, to the air circuit 4170, and/or to the patient interface 3000.

5.6 Humidifier

5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.7 Breathing Waveforms

FIG. 6 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Respiratory Therapy Modes

Various respiratory therapy modes may be implemented by the disclosed respiratory therapy system including CPAP therapy and bi-level therapy.

5.9 Glossary

For the purposes of the present technology disclosure, in certain forms of the present technology, one or more of the following definitions may apply. In other forms of the present technology, alternative definitions may apply.

5.9.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g\text{-}f/cm^2$ and hectopascal. 1 $cmH_2O$ is equal to 1 $g\text{-}f/cm^2$ and is approximately 0.98 hectopascal (1 hectopascal=100 Pa=100 $N/m^2$=1 millibar 0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.9.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.9.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component. A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.9.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.9.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired interface pressure which the ventilator will attempt to achieve at a given time.

End expiratory pressure (EEP): Desired interface pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired interface pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

5.9.4 Anatomy
5.9.4.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius): A point on the face between the mouth and supramenton, lying in the median sagittal plane.

Lip, upper (labrale superius): A point on the face between the mouth and nose, lying in the median sagittal plane.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.9.4.2 Anatomy of the Skull Frontal bone: The frontal bone includes a large vertical portion, the squama *frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.9.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.9.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having some bending, tensile and compressive stiffness. For example, a curved structural wall of a mask may be a shell. In some forms a shell or portions of a shell, may not be rigid. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.9.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.9.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.9.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical-topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.9.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.9.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.10 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.11 Reference Signs List

| | |
|---|---|
| patient | 1000 |
| area proximate ala | 1010 |
| alar crest | 1020 |
| bed partner | 1100 |
| seal forming structure | 3100 |
| first seal forming structure | 3101 |
| second seal forming structure | 3102 |
| boundary | 3103 |
| central portion | 3110 |
| lateral portion | 3111 |
| posterior surfaces of lateral portion | 3112 |
| ridge | 3120 |
| lip inferior portion | 3130 |
| lip superior portion | 3131 |
| peripheral portion | 3132 |
| oral hole | 3133 |
| nasal aperture(s) | 3135 |
| plenum chamber | 3200 |
| oral portion of plenum chamber | 3201 |
| nasal portion or plenum, chamber | 3202 |
| chord | 3210 |
| superior point | 3220 |
| inferior point | 3230 |
| first anterior wall portion | 3240 |
| boundary of oral and nasal portion | 3241 |
| second anterior wall portion | 3242 |
| first anterior wall portion superior boundary | 3243 |
| first anterior wall portion inferior boundary | 3244 |
| lateral side wall portion | 3245 |
| lateral side wall portion | 3246 |
| second anterior wall portion superior boundary | 3247 |
| second anterior wall portion inferior boundary | 3248 |
| shell | 3250 |
| central portion | 3251 |
| support portions | 3260 |
| first end of support portion | 3261 |

-continued

| | |
|---|---|
| second end of support portion | 3262 |
| rigid portion | 3263 |
| band | 3270 |
| cavity | 3272 |
| groove | 3280 |
| projection | 3284 |
| protrusion | 3288 |
| positioning and stabilising structure | 3300 |
| connectors | 3310 |
| arms | 3320 |
| frame | 3350 |
| loop inner surface | 3351 |
| connection point | 3352 |
| first loop | 3352a |
| second loop | 3352b |
| eyelet cut | 3353 |
| headgear straps | 3354 |
| left superior headgear strap | 3356 |
| right superior headgear strap | 3358 |
| central portion | 3360 |
| arm | 3362 |
| secondary connection point | 3364 |
| left secondary connection point | 3364a |
| right secondary connection point | 3364b |
| left inferior strap | 3366 |
| right inferior strap | 3368 |
| magnet | 3370 |
| slot | 3372 |
| scallop | 3373 |
| outer casing | 3376 |
| planar surface | 3378 |
| lip | 3380 |
| magnetic member | 3382 |
| overhang | 3384 |
| vent | 3400 |
| vent mounting aperture | 3410 |
| connection port | 3600 |
| forehead support | 3700 |
| RPT device | 4000 |
| external housing | 4010 |
| upper portion | 4012 |
| lower portion | 4014 |
| panel | 4015 |
| chassis | 4016 |
| handle | 4018 |
| pneumatic block | 4020 |
| air filter | 4110 |
| inlet air filter | 4112 |
| muffler | 4120 |
| outlet muffler | 4124 |
| pressure generator | 4140 |
| blower | 4142 |
| motor | 4144 |
| anti-spillback valve | 4160 |
| air circuit | 4170 |
| supplementary gas | 4180 |
| electrical components | 4200 |
| PCBA | 4202 |
| electrical power supply | 4210 |
| input device | 4220 |
| transducers | 4270 |
| humidifier | 5000 |
| humidifier inlet | 5002 |
| humidifier outlet | 5004 |
| humidifier base | 5006 |
| humidifier reservoir | 5110 |
| conductive portion | 5120 |
| reservoir dock | 5130 |
| locking lever | 5135 |
| water level indicator | 5150 |
| heating element | 5240 |
| overhang | 6000 |
| undercut | 6004 |
| inclined surface | 6008 |
| pivot point | 6012 |

The invention claimed is:

1. A patient interface comprising:
a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient;
a first seal-forming structure constructed and arranged to form a seal with a region of the patient's face surrounding an entrance to the patient's mouth such that the flow of air at said therapeutic pressure is delivered to the mouth, the first seal-forming structure constructed and arranged to maintain said therapeutic pressure in the plenum chamber throughout the patient's respiratory cycle in use;
a second seal-forming structure constructed and arranged to form a seal with a region of the patient's face surrounding an entrance to the patient's nose such that the flow of air at said therapeutic pressure is delivered to the nose, the second seal-forming structure constructed and arranged to maintain said therapeutic pressure in the plenum chamber throughout the patient's respiratory cycle in use;
the plenum chamber comprising silicone and having an anterior wall formed of the silicone, the plenum chamber inlet port being an opening formed in the silicone of the anterior wall, the opening being adapted to directly receive a fluid connector; and
a vent structure to allow a continuous flow of gases exhaled by the patient from an interior of the plenum chamber to vent to ambient, said vent structure being sized and shaped to maintain the therapeutic pressure in the plenum chamber in use;
the patent interface further comprising:
a pair of support portions disposed within the plenum chamber and provided on opposite sides of the interface, the pair of support portions contact and extend from the second seal forming structure and to the anterior wall of the plenum chamber, wherein the pair of support portions are configured to oppose compression in an anterior-posterior direction.

2. The patient interface of claim 1, wherein the support portions are connected to portions of the second seal forming structure which seal, in use, against the patient's lip superior.

3. The patient interface of claim 1, wherein the support portions are connected to portions of the second seal forming structure which, in use, seal to the patient's lip superior, directly inferior to the lower corners of the patient's nose.

4. The patient interface of claim 1, wherein the support portions are curved when viewed in cross-section parallel to a sagittal plane.

5. The patient interface of claim 1, wherein the support portions are curved when viewed in cross-section parallel to a frontal plane.

6. The patient interface of claim 1, wherein the plenum chamber comprises an oral portion and a nasal portion.

7. The patient interface of claim 6, wherein each support portion is connected to the oral portion of the plenum chamber adjacent a boundary of a lateral side wall portion of the oral portion and a lateral side wall portion of the nasal portion.

8. The patient interface of claim 7, wherein the lateral side wall portions of the plenum chamber curve inwardly adjacent the boundary with the nasal portion, wherein each support portion is substantially contiguous with an adjacent lateral side wall portion.

9. The patient interface of claim 6, wherein each support portion is connected to the oral portion of the plenum chamber adjacent a boundary of an anterior wall portion of the oral portion and an anterior wall portion of the nasal portion.

10. The patient interface of claim 1, wherein the second seal-forming structure comprises at least one nasal aperture configured to deliver a flow of air at said therapeutic pressure to an entrance to the patient's nares, wherein, in use no part of either support portion is directly inferior to the or each nasal aperture.

11. The patient interface of claim 1, wherein the interface further comprises a positioning and stabilizing structure configured to generate a force to hold the seal forming structure in a therapeutically effective position on the patient's head.

12. The patient interface of claim 1, wherein the plenum chamber is at least partially formed by a shell and the vent structure is provided to the shell.

13. The patient interface of claim 1, wherein the support portions are connected to the second seal forming structure and are connected to the anterior wall of the plenum chamber.

14. The patient interface of claim 1, wherein a boundary between the first seal-forming structure and the second seal-forming structure comprises a ridge, and wherein each of the support portions extends from the ridge in an anterior direction.

15. The patient interface of claim 14, wherein the ridge is configured to engage the patient's face proximate the entrances to the patient's nares, where the ala meets the face above the lip superior, and each of the support portions has an approximate width that is limited to a width of the corner of the patient's nose.

16. The patient interface of claim 1, further comprising an elbow that includes the fluid connector, the elbow being adapted to connect to an air delivery tube to deliver the flow of air into the plenum chamber.

17. A patient interface comprising:
a plenum chamber pressurisable to a therapeutic pressure of at least 6 cmH2O above ambient air pressure, the plenum chamber including an oral portion and a nasal portion, said plenum chamber further including a plenum chamber inlet port sized and structured to receive a flow of air at the therapeutic pressure for breathing by a patient;
a first seal-forming structure in the oral portion of the plenum chamber and being connected to an oral portion of the plenum chamber, the first seal-forming structure constructed and arranged to form a seal with a region of the patient's face surrounding an entrance to the patient's mouth such that the flow of air at said therapeutic pressure is delivered to the mouth, the first seal-forming structure constructed and arranged to maintain said therapeutic pressure in the plenum chamber throughout the patient's respiratory cycle in use;
a second seal-forming structure in the nasal portion of the plenum chamber and being connected to a nasal portion of the plenum chamber, the second seal-forming structure constructed and arranged to form a seal with a region of the patient's face surrounding an entrance to the patient's nose such that the flow of air at said therapeutic pressure is delivered to the nose, the second seal-forming structure constructed and arranged to maintain said therapeutic pressure in the plenum chamber throughout the patient's respiratory cycle in use; and
a vent structure to allow a continuous flow of gases exhaled by the patient from an interior of the plenum chamber to vent to ambient, said vent structure being sized and shaped to maintain the therapeutic pressure in the plenum chamber in use;
the plenum chamber comprising silicone and having an anterior wall formed of the silicone, the plenum chamber inlet port being an opening formed in the silicone of the anterior wall, the opening being adapted to directly receive a fluid connector;
wherein:
posterior surfaces of lateral portions of the second seal forming structure slope in a superior-anterior direction from a boundary of the first and second seal forming structures;
the patent interface is configured such that no part contacts the patient's alar crest point, in use, and
the patient interface includes a pair of support portions disposed within the plenum chamber and provided on opposite sides of the interface, the pair of support portions contact and extend from the second seal forming structure and to the anterior wall of the plenum chamber, wherein the pair of support portions are configured to oppose compression only in an anterior-posterior direction.

18. The patient interface of claim 17, wherein the slope of each lateral portion forms an angle of between 20 degrees and 90 degrees with a mid-contact plane of the interface.

19. The patient interface of claim 17, wherein the interface is configured to prevent occlusion of the patient's nares.

20. The patient interface of claim 17, further comprising an elbow that includes the fluid connector, the elbow being adapted to connect to an air delivery tube to deliver the flow of air into the plenum chamber.

21. The patient interface of claim 17, wherein a boundary between the first seal-forming structure and the second seal-forming structure comprises a ridge, and wherein each of the support portions extends from the ridge in an anterior direction.

22. The patient interface of claim 21, wherein the ridge is configured to engage the patient's face proximate the entrances to the patient's nares, where the ala meets the face above the lip superior, and each of the support portions has an approximate width that is limited to a width of the corner of the patient's nose.

23. A patient interface comprising:
a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient;
a first seal-forming structure connected to an oral portion of the plenum chamber, the first seal-forming structure constructed and arranged to form a seal with a region of the patient's face surrounding an entrance to the patient's mouth such that the flow of air at said therapeutic pressure is delivered to the mouth, the first seal-forming structure constructed and arranged to maintain said therapeutic pressure in the plenum chamber throughout the patient's respiratory cycle in use;
a second seal-forming structure connected to a nasal portion of the plenum chamber, the second seal-forming structure constructed and arranged to form a seal with a region of the patient's face surrounding an entrance to the patient's nose such that the flow of air at said therapeutic pressure is delivered to the nose, the second seal-forming structure constructed and arranged to maintain said therapeutic pressure in the plenum chamber throughout the patient's respiratory cycle in use; and a vent structure to allow a continuous flow of gases exhaled by the patient from an interior of the plenum chamber to vent to ambient, said vent structure being sized and shaped to maintain the therapeutic pressure in the plenum chamber in use;

wherein;
- a boundary between the first seal-forming structure and the second seal-forming structure comprises a ridge;
- a pair of support portions extends from the ridge in an anterior direction, the ridge being configured to engage the patient's face proximate the entrances to the patient's nares, where the ala meets the face above the lip superior, each of the support portions having an approximate width that is limited to a width of the corner of the patient's nose; and the patent interface is configured such that no part contacts the patient's alar crest point, in use.

24. The patient interface of claim 23, wherein the ridge has a radius of curvature of less than 2 mm.

25. The patient interface of claim 23, wherein the ridge extends across substantially an entire boundary between the first seal-forming structure and the second seal-forming structure.

26. The patient interface of claim 23, wherein, in use, the ridge engages a patient's face proximate entrances to the nares where the ala meets the face above the lip superior.

27. The patient interface of claim 23, wherein the ridge resists creases forming in the first and/or second seal forming structure adjacent the ridge.

28. The patient interface of claim 23, wherein, in use, the plenum chamber is at least partially formed by a shell and the vent structure is provided to the shell.

* * * * *